United States Patent
Ano et al.

(10) Patent No.: US 10,434,133 B2
(45) Date of Patent: Oct. 8, 2019

(54) INFLAMMATION-SUPPRESSING COMPOSITION INCLUDING PEPTIDE

(71) Applicant: KIRIN KABUSHIKI KAISHA, Tokyo (JP)

(72) Inventors: Yasuhisa Ano, Tokyo (JP); Masahiro Kita, Tokyo (JP)

(73) Assignee: KIRIN HOLDINGS KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/576,908

(22) PCT Filed: May 26, 2016

(86) PCT No.: PCT/JP2016/065627
§ 371 (c)(1),
(2) Date: Nov. 27, 2017

(87) PCT Pub. No.: WO2016/190395
PCT Pub. Date: Dec. 1, 2016

(65) Prior Publication Data
US 2018/0214505 A1  Aug. 2, 2018

(30) Foreign Application Priority Data

May 27, 2015 (JP) ................. 2015-107924
Apr. 28, 2016 (JP) ................. 2016-091950

(51) Int. Cl.
*A61K 38/05* (2006.01)
*A23L 33/18* (2016.01)
*A61P 25/28* (2006.01)
*A61P 29/00* (2006.01)

(52) U.S. Cl.
CPC .............. *A61K 38/05* (2013.01); *A23L 33/18* (2016.08); *A61P 25/28* (2018.01); *A61P 29/00* (2018.01)

(58) Field of Classification Search
CPC ................. A61K 38/05; A61P 25/28
See application file for complete search history.

(56) References Cited

U.S. PATENT DOCUMENTS

2012/0070392 A1*  3/2012  Lee ............ A61K 38/05
424/59

FOREIGN PATENT DOCUMENTS

| EP | 1 297 830 A1 | 4/2003 |
|---|---|---|
| JP | 2004-261119 A | 9/2004 |
| JP | 2007-509169 A | 4/2007 |
| JP | 2007-254313 A | 10/2007 |
| JP | 2008-092912 A | 4/2008 |
| JP | 2009-221135 A | 10/2009 |
| JP | 2010-539069 A | 12/2010 |
| JP | 2012-158563 A | 8/2012 |
| JP | 2012-522043 A | 9/2012 |
| JP | 2014-509594 A | 4/2014 |
| KR | 10-2014-0045688 A | 4/2014 |
| WO | 2009/033775 A2 | 3/2009 |
| WO | 2013/129220 A1 | 9/2013 |

OTHER PUBLICATIONS

Torres-Fuentes (Identification and characterization of antioxidant peptides from chickpea protein hydrolysates, Food Chemistry 2015, 180: 194-202) (Year: 2015).*
Streit (Microglia and neuroinflammation: a pathological perspective, Journal of Neuroinflammation 2004, 1:14). (Year: 2004).*
Schiavone (Severe Life Stress and Oxidative Stress in the Brain: From Animal Models to Human Pathology, Antioxidants and Redox Signaling 2013, 18:1475) (Year: 2013).*
Takafumi Mizushige et al., "Research for novel neuromodulatory peptide release from rice protein", The Tojuro Iljlma Foundation for Food Science and Technology Nenpo, 2014, pp. 57-61, vol. 29.
Christina Torres-Fuentes et al., "Identification and characterization of antioxidant peptides from chickpea protein hydrolysates", Food Chemistry, Feb. 2015, pp. 194-202, vol. 180.
T. Vezenkov et al., "Galanthamine based hybrid molecules with potential acetylcholinesterase, butyrylcholinesterase and β-secretase, inhibition activity", Journal of Peptide Science, 2010, 1 page, vol. 16.
Michael P. Kurnellas et al., "Amyloid Fibrils Composed of Hexameric Peptides Attenuate Neuroinflammation", NIH Public Access, 2013, 20 pages, vol. 5, No. 179.
Seung-Jae Lee et al., "Purification and characterisation of an antioxidative peptide from enzymatic hydrolysates of duck processing by-products", Food Chemistry, 2010, pp. 216-220, vol. 123.
Barbara S. Berlett et al., "Designing antioxidant peptides", NIH Public Access, Mar. 2014, pp. 80-86, vol. 19, No. 2.
Yoichi Nakamura et al., "Identification of a Peptide Sequence in Albumin that Potentiates Superoxide Production by Microglia", Journal of Neurochemistry, 2000, pp. 2309-2315, vol. 75, No. 6.
Masaya Yasui et al., "A Chronic Fatigue Syndrome Model Demonstrates Mechanical Allodynia and Muscular Hyperalgesia via Spinal Microglial Activation", Wiley Periodicals, Inc., 2014, 11 pages.

(Continued)

*Primary Examiner* — Karlheinz R. Skowronek
*Assistant Examiner* — Khalid Kader
(74) *Attorney, Agent, or Firm* — Sughrue Mion, PLLC

(57) ABSTRACT

An oligopeptide having a good anti-inflammation effect on microglia has been found, and based on this finding, a composition to be used for suppressing the inflammation of microglia is provided. Inflammation suppression action of a dipeptide has been comprehensively analyzed using the proinflammatory cytokine production of microglia as an indicator. As a result, it has been revealed that an oligopeptide including the sequence LH, DV or MH has a good inflammation suppression effect. The composition containing any of these oligopeptides can provide a composition having the effect of suppressing the excessive inflammatory action of microglia.

16 Claims, 10 Drawing Sheets
Specification includes a Sequence Listing.

(56) References Cited

OTHER PUBLICATIONS

Yvonne Couch et al., "Microglial activation, increased TNF and SERT expression in the prefrontal cortex define stress-altered behavior in mice susceptible to anhedonia", Brain, Behavior, and Immunity, 2013, pp. 139-146, vol. 29.

Yelena Y. Grinberg et al., "Insulin-like growth factor-1 abrogates microglial oxidative stress and TNF-α responses to spreading depression", Journal of Neurochemistry, 2013, pp. 662-672, vol. 126 (5).

Kiarash Riazi et al., "Microglial activation and TNFα production mediate altered CNS excitability following peripheral inflammation", PNAS, Nov. 4, 2008, pp. 17151-17156, vol. 105 (44).

Temugin Berta et al., "Extracellular caspase-6 drives murine inflammatory pain via microglial TNF-α secretion", The Journal of Clinical Investigation, Mar. 2014, pp. 1173-1186, vol. 124, No. 3.

Akira Monji, Psychiat. Neurol. Jap., 2012, pp. 124-133, vol. 114, No. 2.

Yasuhito Nakatomi et al., "Neuroinflammation in Patients with Chronic Fatigue Syndrome/Myalgic Encephalomyelitis: An $^{11}$C-(R)-PK11195 PET Study", J. Nucl. Med., 2014, pp. 945-950, vol. 55.

International Search Report for PCT/JP2016/065627 dated Jun. 28, 2016 [PCT/ISA/210].

\* cited by examiner

FIG.3

| Group | Treatment | Number of days from the day test started | | | | | | |
|---|---|---|---|---|---|---|---|---|
| | | 1 | 2 | 3 | 4 | 5 | 6 | 7 (Sample collection day) |
| LH 0 mg group (4 mice) | LH-containing diet | | | | | | | |
| | LPS administered | | | | | | | ↓ |
| LH 10 mg group (3 mice) | LH (10 mg/kg body weight)-containing diet | ↓ | ↓ | ↓ | ↓ | ↓ | ↓ | |
| | LPS administered | | | | | | | ↓ |
| LH 50 mg group (5 mice) | LH (50 mg/kg body weight)-containing diet | ↓ | ↓ | ↓ | ↓ | ↓ | ↓ | |
| | LPS administered | | | | | | | ↓ |
| LPS non-administered group (3 mice) | LH-containing diet | | | | | | | |
| | LPS administered | | | | | | | ↓ |

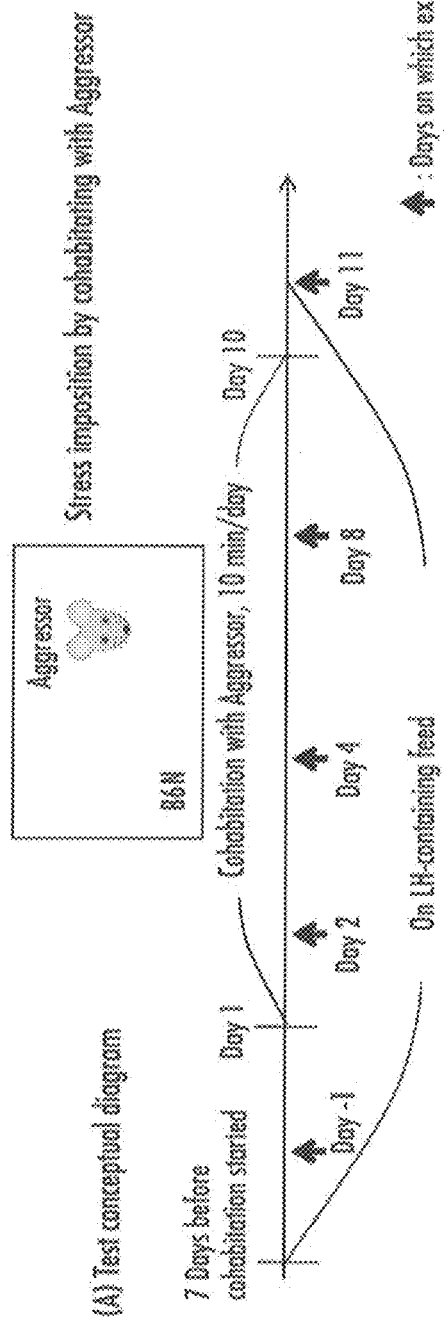
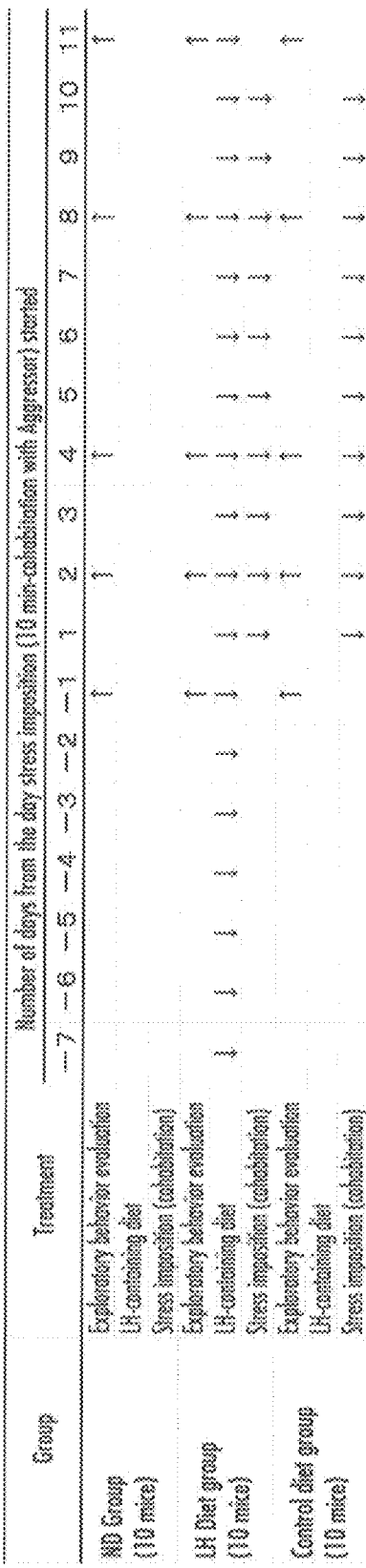
FIG. 5A
FIG. 5B

FIG.5C
(C) Test device for exploratory behavior evaluation
(C-1; Plan view)  Aggressor
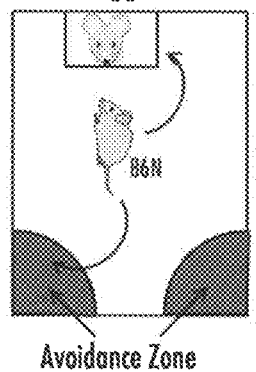
Avoidance Zone
(C-2; Cubic view)
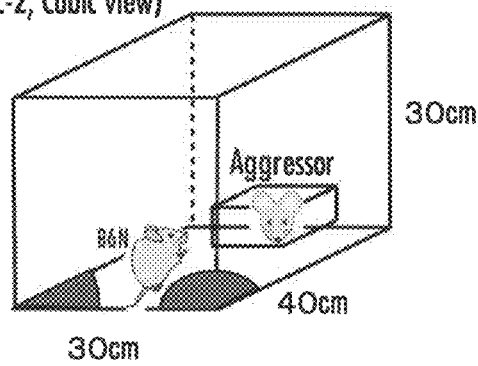

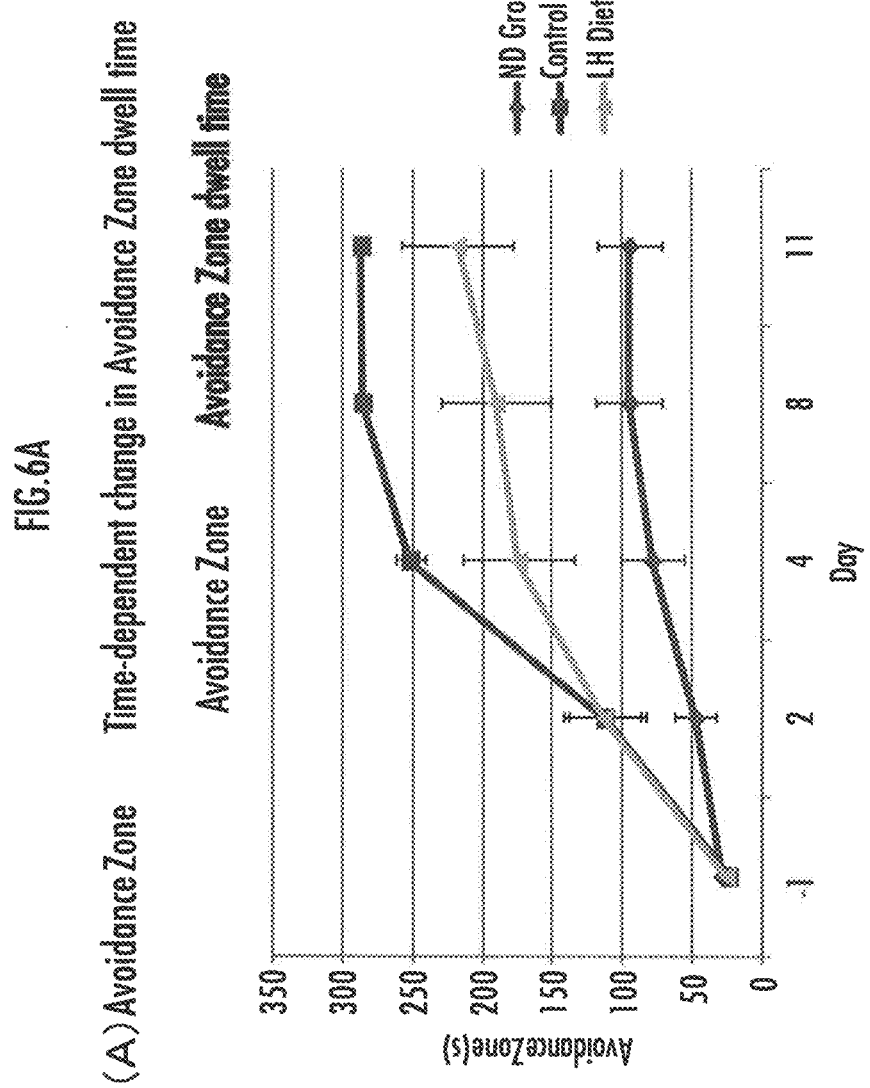

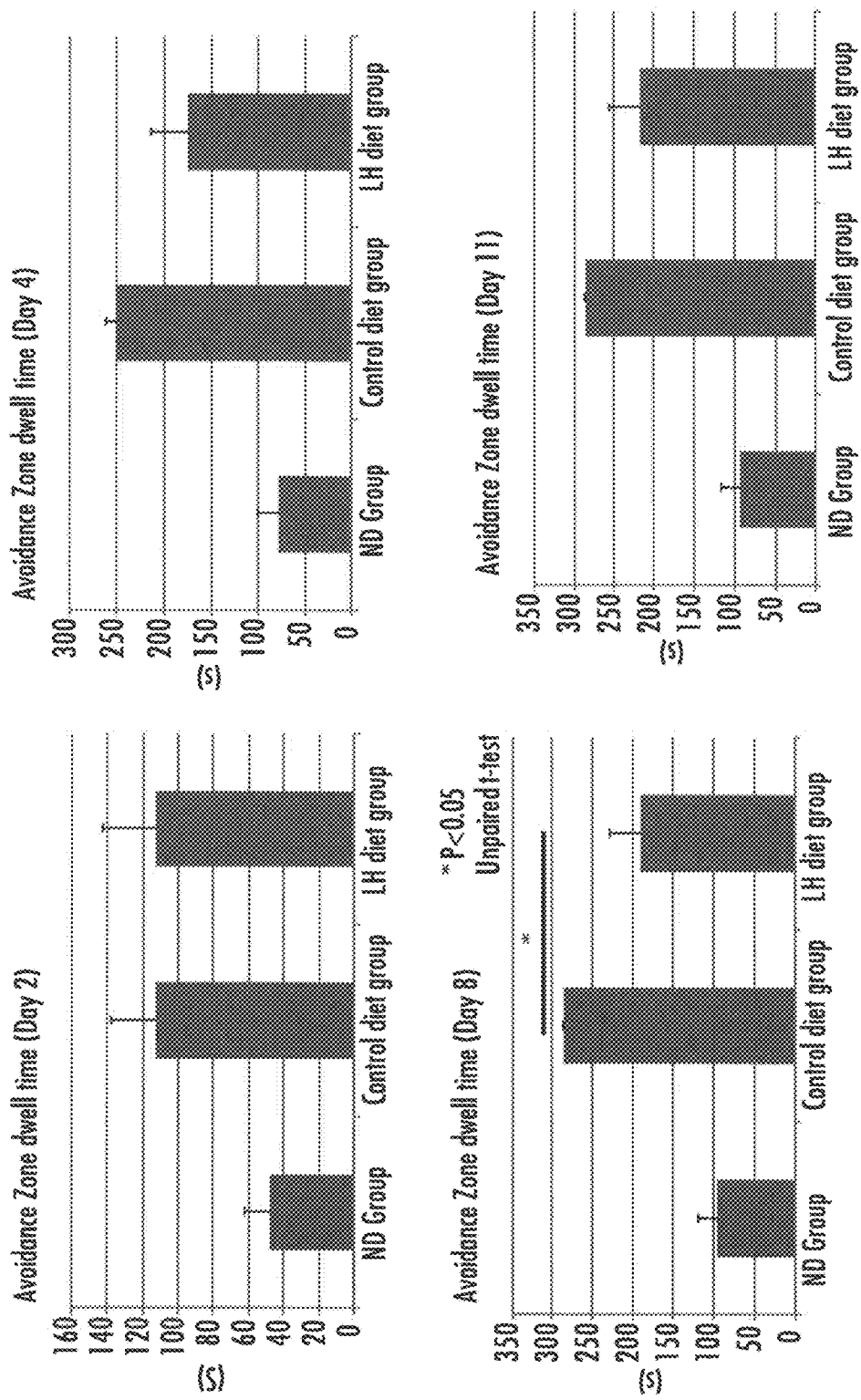

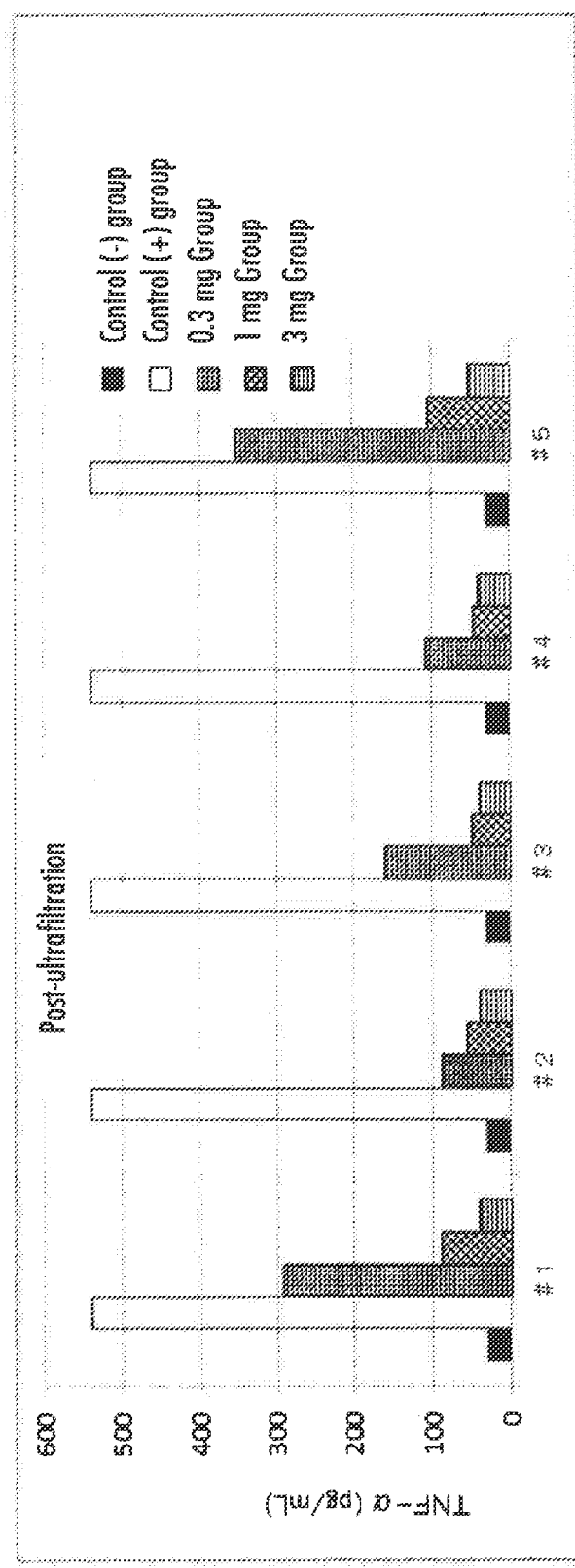

SEQUENCE LISTING

```
<160> NUMBER OF SEQ ID NOS: 46

<210> SEQ ID NO 1
<211> LENGTH: 214
<212> TYPE: PRT
<213> ORGANISM: Bos taurus

<400> SEQUENCE: 1

Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
            20                  25                  30

Glu Asn Leu Leu Arg Phe Phe Val Ala Pro Phe Pro Glu Val Phe Gly
        35                  40                  45

Lys Glu Lys Val Asn Glu Leu Ser Lys Asp Ile Gly Ser Glu Ser Thr
50                  55                  60

Glu Asp Gln Ala Met Glu Asp Ile Lys Gln Met Glu Ala Glu Ser Ile
65                  70                  75                  80

Ser Ser Ser Glu Glu Ile Val Pro Asn Ser Val Glu Gln Lys His Ile
                85                  90                  95

Gln Lys Glu Asp Val Pro Ser Glu Arg Tyr Leu Gly Tyr Leu Glu Gln
            100                 105                 110

Leu Leu Arg Leu Lys Lys Tyr Lys Val Pro Gln Leu Glu Ile Val Pro
        115                 120                 125

Asn Ser Ala Glu Glu Arg Leu His Ser Met Lys Glu Gly Ile His Ala
130                 135                 140

Gln Gln Lys Glu Pro Met Ile Gly Val Asn Gln Glu Leu Ala Tyr Phe
145                 150                 155                 160

Tyr Pro Glu Leu Phe Arg Gln Phe Tyr Gln Leu Asp Ala Tyr Pro Ser
                165                 170                 175

Gly Ala Trp Tyr Tyr Val Pro Leu Gly Thr Gln Tyr Thr Asp Ala Pro
            180                 185                 190

Ser Phe Ser Asp Ile Pro Asn Pro Ile Gly Ser Glu Asn Ser Glu Lys
        195                 200                 205
```

```
Thr Thr Met Pro Leu Trp
        210

<210> SEQ ID NO 2
<211> LENGTH: 224
<212> TYPE: PRT
<213> ORGANISM: Bos taurus

<400> SEQUENCE: 2

Met Lys Val Leu Ile Leu Ala Cys Leu Val Ala Leu Ala Leu Ala Arg
1               5                   10                  15

Glu Leu Glu Glu Leu Asn Val Pro Gly Glu Ile Val Glu Ser Leu Ser
            20                  25                  30

Ser Ser Glu Glu Ser Ile Thr Arg Ile Asn Lys Lys Ile Glu Lys Phe
        35                  40                  45

Gln Ser Glu Glu Gln Gln Gln Thr Glu Asp Glu Leu Gln Asp Lys Ile
    50                  55                  60

His Pro Phe Ala Gln Thr Gln Ser Leu Val Tyr Pro Phe Pro Gly Pro
65                  70                  75                  80

Ile Pro Asn Ser Leu Pro Gln Asn Ile Pro Pro Leu Thr Gln Thr Pro
                85                  90                  95

Val Val Val Pro Pro Phe Leu Gln Pro Glu Val Met Gly Val Ser Lys
            100                 105                 110

Val Lys Glu Ala Met Ala Pro Lys His Lys Glu Met Pro Phe Pro Lys
        115                 120                 125

Tyr Pro Val Glu Pro Phe Thr Glu Ser Gln Ser Leu Thr Leu Thr Asp
    130                 135                 140

Val Glu Asn Leu His Leu Pro Leu Pro Leu Leu Gln Ser Trp Met His
145                 150                 155                 160

Gln Pro His Gln Pro Leu Pro Pro Thr Val Met Phe Pro Pro Gln Ser
                165                 170                 175

Val Leu Ser Leu Ser Gln Ser Lys Val Leu Pro Val Pro Gln Lys Ala
            180                 185                 190

Val Pro Tyr Pro Gln Arg Asp Met Pro Ile Gln Ala Phe Leu Leu Tyr
        195                 200                 205

Gln Glu Pro Val Leu Gly Pro Val Arg Gly Pro Phe Pro Ile Ile Val
    210                 215                 220

<210> SEQ ID NO 3
<211> LENGTH: 190
<212> TYPE: PRT
<213> ORGANISM: Bos taurus

<400> SEQUENCE: 3

Met Met Lys Ser Phe Phe Leu Val Val Thr Ile Leu Ala Leu Thr Leu
1               5                   10                  15

Pro Phe Leu Gly Ala Gln Glu Gln Asn Gln Glu Gln Pro Ile Arg Cys
            20                  25                  30

Glu Lys Asp Glu Arg Phe Phe Ser Asp Lys Ile Ala Lys Tyr Ile Pro
        35                  40                  45

Ile Gln Tyr Val Leu Ser Arg Tyr Pro Ser Tyr Gly Leu Asn Tyr Tyr
    50                  55                  60

Gln Gln Lys Pro Val Ala Leu Ile Asn Asn Gln Phe Leu Pro Tyr Pro
65                  70                  75                  80

Tyr Tyr Ala Lys Pro Ala Ala Val Arg Ser Pro Ala Gln Ile Leu Gln
                85                  90                  95
```

Trp Gln Val Leu Ser Asn Thr Val Pro Ala Lys Ser Cys Gln Ala Gln
              100                 105                 110

Pro Thr Thr Met Ala Arg His Pro His Pro His Leu Ser Phe Met Ala
              115                 120                 125

Ile Pro Pro Lys Lys Asn Gln Asp Lys Thr Glu Ile Pro Thr Ile Asn
130                 135                 140

Thr Ile Ala Ser Gly Glu Pro Thr Ser Thr Pro Thr Thr Glu Ala Val
145                 150                 155                 160

Glu Ser Thr Val Ala Thr Leu Glu Asp Ser Pro Glu Val Ile Glu Ser
                    165                 170                 175

Pro Pro Glu Ile Asn Thr Val Gln Val Thr Ser Thr Ala Val
                180                 185                 190

<210> SEQ ID NO 4
<211> LENGTH: 178
<212> TYPE: PRT
<213> ORGANISM: Bos taurus

<400> SEQUENCE: 4

Met Lys Cys Leu Leu Leu Ala Leu Ala Leu Thr Cys Gly Ala Gln Ala
1               5                   10                  15

Leu Ile Val Thr Gln Thr Met Lys Gly Leu Asp Ile Gln Lys Val Ala
                20                  25                  30

Gly Thr Trp Tyr Ser Leu Ala Met Ala Ala Ser Asp Ile Ser Leu Leu
            35                  40                  45

Asp Ala Gln Ser Ala Pro Leu Arg Val Tyr Val Glu Glu Leu Lys Pro
        50                  55                  60

Thr Pro Glu Gly Asp Leu Glu Ile Leu Leu Gln Lys Trp Glu Asn Gly
65                  70                  75                  80

Glu Cys Ala Gln Lys Lys Ile Ile Ala Glu Lys Thr Lys Ile Pro Ala
                85                  90                  95

Val Phe Lys Ile Asp Ala Leu Asn Glu Asn Lys Val Leu Val Leu Asp
                100                 105                 110

Thr Asp Tyr Lys Lys Tyr Leu Leu Phe Cys Met Glu Asn Ser Ala Glu
            115                 120                 125

Pro Glu Gln Ser Leu Ala Cys Gln Cys Leu Val Arg Thr Pro Glu Val
        130                 135                 140

Asp Asp Glu Ala Leu Glu Lys Phe Asp Lys Ala Leu Lys Ala Leu Pro
145                 150                 155                 160

Met His Ile Arg Leu Ser Phe Asn Pro Thr Gln Leu Glu Glu Gln Cys
                165                 170                 175

His Ile

<210> SEQ ID NO 5
<211> LENGTH: 142
<212> TYPE: PRT
<213> ORGANISM: Bos taurus

<400> SEQUENCE: 5

Met Met Ser Phe Val Ser Leu Leu Leu Val Gly Ile Leu Phe His Ala
1               5                   10                  15

Thr Gln Ala Glu Gln Leu Thr Lys Cys Glu Val Phe Arg Glu Leu Lys
                20                  25                  30

Asp Leu Lys Gly Tyr Gly Gly Val Ser Leu Pro Glu Trp Val Cys Thr
            35                  40                  45

```
Ala Phe His Thr Ser Gly Tyr Asp Thr Gln Ala Ile Val Gln Asn Asn
 50                  55                  60

Asp Ser Thr Glu Tyr Gly Leu Phe Gln Ile Asn Asn Lys Ile Trp Cys
 65                  70                  75                  80

Lys Asp Asp Gln Asn Pro His Ser Ser Asn Ile Cys Asn Ile Ser Cys
                 85                  90                  95

Asp Lys Phe Leu Asp Asp Leu Thr Asp Asp Ile Met Cys Val Lys
             100                 105                 110

Lys Ile Leu Asp Lys Val Gly Ile Asn Tyr Trp Leu Ala His Lys Ala
             115                 120                 125

Leu Cys Ser Glu Lys Leu Asp Gln Trp Leu Cys Glu Lys Leu
 130                 135                 140
```

<210> SEQ ID NO 6
<211> LENGTH: 711
<212> TYPE: PRT
<213> ORGANISM: Bos taurus

<400> SEQUENCE: 6

```
Trp Val Cys Leu Gln Leu Pro Val Phe Leu Ala Ser Val Thr Leu Phe
 1               5                  10                  15

Glu Val Ala Ala Ser Asp Thr Ile Ala Gln Ala Ala Ser Thr Thr Thr
                 20                  25                  30

Ile Ser Asp Ala Val Ser Lys Val Lys Ile Gln Val Asn Lys Ala Phe
             35                  40                  45

Leu Asp Ser Arg Thr Arg Leu Lys Thr Thr Leu Ser Ser Glu Ala Pro
 50                  55                  60

Thr Thr Gln Gln Leu Ser Glu Tyr Phe Lys His Ala Lys Gly Arg Thr
 65                  70                  75                  80

Arg Thr Ala Ile Arg Asn Gly Gln Val Trp Glu Glu Ser Leu Lys Arg
                 85                  90                  95

Leu Arg Arg Asp Thr Thr Leu Thr Asn Val Thr Asp Pro Ser Leu Asp
             100                 105                 110

Leu Thr Ala Leu Ser Trp Glu Val Gly Cys Gly Ala Pro Val Pro Leu
             115                 120                 125

Val Lys Cys Asp Glu Asn Ser Pro Tyr Arg Thr Ile Thr Gly Asp Cys
 130                 135                 140

Asn Asn Arg Arg Ser Pro Ala Leu Gly Ala Ala Asn Arg Ala Leu Ala
145                 150                 155                 160

Arg Trp Leu Pro Ala Glu Tyr Glu Asp Gly Leu Ala Leu Pro Phe Gly
                 165                 170                 175

Trp Thr Gln Arg Lys Thr Arg Asn Gly Phe Arg Val Pro Leu Ala Arg
             180                 185                 190

Glu Val Ser Asn Lys Ile Val Gly Tyr Leu Asp Glu Gly Val Leu
             195                 200                 205

Asp Gln Asn Arg Ser Leu Leu Phe Met Gln Trp Gly Gln Ile Val Asp
 210                 215                 220

His Asp Leu Asp Phe Ala Pro Glu Thr Glu Leu Gly Ser Asn Glu His
225                 230                 235                 240

Ser Lys Thr Gln Cys Glu Glu Tyr Cys Ile Gln Gly Asp Asn Cys Phe
                 245                 250                 255

Pro Ile Met Phe Pro Lys Asn Asp Pro Lys Leu Lys Thr Gln Gly Lys
             260                 265                 270

Cys Met Pro Phe Phe Arg Ala Gly Phe Val Cys Pro Thr Pro Pro Tyr
             275                 280                 285
```

```
Gln Ser Leu Ala Arg Glu Gln Ile Asn Ala Val Thr Ser Phe Leu Asp
    290                 295                 300

Ala Ser Leu Val Tyr Gly Ser Glu Pro Ser Leu Ala Ser Arg Leu Arg
305                 310                 315                 320

Asn Leu Ser Ser Pro Leu Gly Leu Met Ala Val Asn Gln Glu Ala Trp
                325                 330                 335

Asp His Gly Leu Ala Tyr Leu Pro Phe Asn Asn Lys Lys Pro Ser Pro
            340                 345                 350

Cys Glu Phe Ile Asn Thr Thr Ala Arg Val Pro Cys Phe Leu Ala Gly
        355                 360                 365

Asp Phe Arg Ala Ser Glu Gln Ile Leu Leu Ala Thr Ala His Thr Leu
    370                 375                 380

Leu Leu Arg Glu His Asn Arg Leu Ala Arg Glu Leu Lys Lys Leu Asn
385                 390                 395                 400

Pro His Trp Asn Gly Glu Lys Leu Tyr Gln Glu Ala Arg Lys Ile Leu
                405                 410                 415

Gly Ala Phe Ile Gln Ile Ile Thr Phe Arg Asp Tyr Leu Pro Ile Val
            420                 425                 430

Leu Gly Ser Glu Met Gln Lys Trp Ile Pro Pro Tyr Gln Gly Tyr Asn
        435                 440                 445

Asn Ser Val Asp Pro Arg Ile Ser Asn Val Phe Thr Phe Ala Phe Arg
    450                 455                 460

Phe Gly His Met Glu Val Pro Ser Thr Val Ser Arg Leu Asp Glu Asn
465                 470                 475                 480

Tyr Gln Pro Trp Gly Pro Glu Ala Glu Leu Pro Leu His Thr Leu Phe
                485                 490                 495

Phe Asn Thr Trp Arg Ile Ile Lys Asp Gly Gly Ile Asp Pro Leu Val
            500                 505                 510

Arg Gly Leu Leu Ala Lys Lys Ser Lys Leu Met Asn Gln Asp Lys Met
        515                 520                 525

Val Thr Ser Glu Leu Arg Asn Lys Leu Phe Gln Pro Thr His Lys Ile
    530                 535                 540

His Gly Phe Asp Leu Ala Ala Ile Asn Leu Gln Arg Cys Arg Asp His
545                 550                 555                 560

Gly Met Pro Gly Tyr Asn Ser Trp Arg Gly Phe Cys Gly Leu Ser Gln
                565                 570                 575

Pro Lys Thr Leu Lys Gly Leu Gln Thr Val Leu Lys Asn Lys Ile Leu
            580                 585                 590

Ala Lys Lys Leu Met Asp Leu Tyr Lys Thr Pro Asp Asn Ile Asp Ile
        595                 600                 605

Trp Ile Gly Gly Asn Ala Glu Pro Met Val Glu Arg Gly Arg Val Gly
    610                 615                 620

Pro Leu Leu Ala Cys Leu Leu Gly Arg Gln Phe Gln Gln Ile Arg Asp
625                 630                 635                 640

Gly Asp Arg Phe Trp Trp Glu Asn Pro Gly Val Phe Thr Glu Lys Gln
                645                 650                 655

Arg Asp Ser Leu Gln Lys Val Ser Phe Ser Arg Leu Ile Cys Asp Asn
            660                 665                 670

Thr His Ile Thr Lys Val Pro Leu His Ala Phe Gln Ala Asn Asn Tyr
        675                 680                 685

Pro His Asp Phe Val Asp Cys Ser Thr Val Asp Lys Leu Asp Leu Ser
    690                 695                 700
```

```
Pro Trp Ala Ser Arg Glu Asn
705                 710

<210> SEQ ID NO 7
<211> LENGTH: 708
<212> TYPE: PRT
<213> ORGANISM: Bos taurus

<400> SEQUENCE: 7

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
            20                  25                  30

Pro Glu Trp Phe Lys Cys Arg Arg Trp Gln Trp Arg Met Lys Lys Leu
        35                  40                  45

Gly Ala Pro Ser Ile Thr Cys Val Arg Ala Phe Ala Leu Glu Cys
    50                  55                  60

Ile Arg Ala Ile Ala Glu Lys Lys Ala Asp Ala Val Thr Leu Asp Gly
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
        115                 120                 125

Gln Gly Arg Lys Ser Cys His Thr Gly Leu Gly Arg Ser Ala Gly Trp
    130                 135                 140

Val Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
        195                 200                 205

Phe Gly Tyr Ser Gly Ala Phe Lys Cys Leu Gln Asp Gly Ala Gly Asp
    210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
                245                 250                 255

Pro Val Asp Ala Phe Lys Glu Cys His Leu Ala Gln Val Pro Ser His
            260                 265                 270

Ala Val Val Ala Arg Ser Val Asp Gly Lys Glu Asp Leu Ile Trp Lys
        275                 280                 285

Leu Leu Ser Lys Ala Gln Glu Lys Phe Gly Lys Asn Lys Ser Arg Ser
    290                 295                 300

Phe Gln Leu Phe Gly Ser Pro Gly Gln Arg Asp Leu Leu Phe Lys
305                 310                 315                 320

Asp Ser Ala Leu Gly Phe Leu Arg Ile Pro Ser Lys Val Asp Ser Ala
                325                 330                 335

Leu Tyr Leu Gly Ser Arg Tyr Leu Thr Thr Leu Lys Asn Leu Arg Glu
            340                 345                 350

Thr Ala Glu Glu Val Lys Ala Arg Tyr Thr Arg Val Val Trp Cys Ala
        355                 360                 365
```

Val Gly Pro Glu Glu Gln Lys Lys Cys Gln Gln Trp Ser Gln Gln Ser
        370                 375                 380

Gly Gln Asn Val Thr Cys Ala Thr Ala Ser Thr Thr Asp Asp Cys Ile
385                 390                 395                 400

Val Leu Val Leu Lys Gly Glu Ala Asp Ala Leu Asn Leu Asp Gly Gly
                405                 410                 415

Tyr Ile Tyr Thr Ala Gly Lys Cys Gly Leu Val Pro Val Leu Ala Glu
                420                 425                 430

Asn Arg Lys Thr Ser Lys Tyr Ser Leu Asp Cys Val Leu Arg Pro
        435                 440                 445

Thr Glu Gly Tyr Leu Ala Val Ala Val Val Lys Lys Ala Asn Glu Gly
        450                 455                 460

Leu Thr Trp Asn Ser Leu Lys Asp Lys Ser Cys His Thr Ala Val
465                 470                 475                 480

Asp Arg Thr Ala Gly Trp Asn Ile Pro Met Gly Leu Ile Val Asn Gln
                485                 490                 495

Thr Gly Ser Cys Ala Phe Asp Glu Phe Phe Ser Gln Ser Cys Ala Pro
                500                 505                 510

Gly Arg Asp Pro Lys Ser Arg Leu Cys Ala Leu Cys Ala Gly Asp Asp
        515                 520                 525

Gln Gly Leu Asp Lys Cys Val Pro Asn Ser Lys Glu Lys Tyr Tyr Gly
        530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Thr
                565                 570                 575

Ala Asp Trp Ala Lys Asn Leu Asn Arg Glu Asp Phe Arg Leu Leu Cys
        580                 585                 590

Leu Asp Gly Thr Arg Lys Pro Val Thr Glu Ala Gln Ser Cys His Leu
        595                 600                 605

Ala Val Ala Pro Asn His Ala Val Val Ser Arg Ser Asp Arg Ala Ala
        610                 615                 620

His Val Lys Gln Val Leu Leu His Gln Gln Ala Leu Phe Gly Lys Asn
625                 630                 635                 640

Gly Lys Asn Cys Pro Asp Lys Phe Cys Leu Phe Lys Ser Glu Thr Lys
                645                 650                 655

Asn Leu Leu Phe Asn Asp Asn Thr Glu Cys Leu Ala Lys Leu Gly Gly
                660                 665                 670

Arg Pro Thr Tyr Glu Glu Tyr Leu Gly Thr Glu Tyr Val Thr Ala Ile
        675                 680                 685

Ala Asn Leu Lys Lys Cys Ser Thr Ser Pro Leu Leu Glu Ala Cys Ala
        690                 695                 700

Phe Leu Thr Arg
705

<210> SEQ ID NO 8
<211> LENGTH: 164
<212> TYPE: PRT
<213> ORGANISM: Bos taurus

<400> SEQUENCE: 8

Met Asn Pro Leu Trp Thr Leu Leu Phe Val Leu Ser Ala Pro Arg Gly
1               5                   10                  15

Val Leu Ser Gln Val Gln Leu Arg Glu Ser Gly Pro Ser Leu Val Lys

```
                        20                  25                  30
Pro Ser Gln Thr Leu Ser Leu Thr Cys Thr Val Ser Gly Phe Ser Leu
                35                  40                  45
Ser Ser Tyr Ala Val Gly Trp Val Arg Gln Ala Pro Gly Lys Ala Leu
        50                  55                  60
Glu Trp Val Gly Gly Ile Asp Gly Gly Ser Thr Tyr Tyr Asn Pro
65                  70                  75                  80
Ala Leu Lys Ser Arg Leu Ser Ile Thr Lys Asp Asn Ser Lys Ser Gln
                85                  90                  95
Val Ser Leu Ser Val Ser Ser Val Thr Pro Glu Asp Thr Ala Thr Tyr
                100                 105                 110
Tyr Cys Ala Lys Cys Val Gly Tyr Ala Gly Ser Arg Ser Gly Cys Tyr
                115                 120                 125
Tyr Leu Arg Gly Gly Tyr Gly Pro His Val Asp Ala Trp Gly Gln Gly
                130                 135                 140
Leu Leu Val Thr Val Ser Ser Ala Ser Thr Thr Ala Pro Lys Val Tyr
145                 150                 155                 160
Pro Leu Ser Ser

<210> SEQ ID NO 9
<211> LENGTH: 101
<212> TYPE: PRT
<213> ORGANISM: Bos taurus

<400> SEQUENCE: 9

Gln Ser Gly Leu Thr Gln Pro Ser Ser Val Ser Gly Asn Leu Gly Gln
1               5                   10                  15
Thr Val Ile Thr Ser Cys Ala Gly Thr Ser Ser Tyr Val Gly Ser Tyr
                20                  25                  30
Asn Gly Val Gly Trp Tyr Gln Gln Leu Pro Gly Ser Ala Pro Lys Thr
                35                  40                  45
Leu Ile Tyr Asn Val Ser Lys Arg Pro Ser Gly Ile Pro Asp Arg Phe
        50                  55                  60
Ser Gly Ser Lys Ser Gly Asn Thr Ala Thr Leu Thr Val Ser Gly Leu
65                  70                  75                  80
Gln Ala Glu Asp Glu Ala Asp Tyr Tyr Cys Ser Ser Tyr Lys Ser Gly
                85                  90                  95
Gly Ser Val His Ser
                100

<210> SEQ ID NO 10
<211> LENGTH: 607
<212> TYPE: PRT
<213> ORGANISM: Bos taurus

<400> SEQUENCE: 10

Met Lys Trp Val Thr Phe Ile Ser Leu Leu Leu Leu Phe Ser Ser Ala
1               5                   10                  15
Tyr Ser Arg Gly Val Phe Arg Arg Asp Thr His Lys Ser Glu Ile Ala
                20                  25                  30
His Arg Phe Lys Asp Leu Gly Glu Glu His Phe Lys Gly Leu Val Leu
                35                  40                  45
Ile Ala Phe Ser Gln Tyr Leu Gln Gln Cys Pro Phe Asp Glu His Val
        50                  55                  60
Lys Leu Val Asn Glu Leu Thr Glu Phe Ala Lys Thr Cys Val Ala Asp
65                  70                  75                  80
```

```
Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
                100                 105                 110

Asp Cys Cys Glu Lys Gln Glu Pro Glu Arg Asn Glu Cys Phe Leu Ser
                115                 120                 125

His Lys Asp Asp Ser Pro Asp Leu Pro Lys Leu Lys Pro Asp Pro Asn
            130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
                180                 185                 190

Gln Ala Glu Asp Lys Gly Ala Cys Leu Leu Pro Lys Ile Glu Thr Met
                195                 200                 205

Arg Glu Lys Val Leu Ala Ser Ser Ala Arg Gln Arg Leu Arg Cys Ala
            210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                245                 250                 255

Leu Val Thr Asp Leu Thr Lys Val His Lys Glu Cys Cys His Gly Asp
                260                 265                 270

Leu Leu Glu Cys Ala Asp Asp Arg Ala Asp Leu Ala Lys Tyr Ile Cys
            275                 280                 285

Asp Asn Gln Asp Thr Ile Ser Ser Lys Leu Lys Glu Cys Cys Asp Lys
            290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
                325                 330                 335

Asp Val Cys Lys Asn Tyr Gln Glu Ala Lys Asp Ala Phe Leu Gly Ser
                340                 345                 350

Phe Leu Tyr Glu Tyr Ser Arg Arg His Pro Glu Tyr Ala Val Ser Val
                355                 360                 365

Leu Leu Arg Leu Ala Lys Glu Tyr Glu Ala Thr Leu Glu Glu Cys Cys
            370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
                405                 410                 415

Gln Phe Glu Lys Leu Gly Glu Tyr Gly Phe Gln Asn Ala Leu Ile Val
                420                 425                 430

Arg Tyr Thr Arg Lys Val Pro Gln Val Ser Thr Pro Thr Leu Val Glu
            435                 440                 445

Val Ser Arg Ser Leu Gly Lys Val Gly Thr Arg Cys Cys Thr Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495
```

```
Thr Lys Cys Cys Thr Glu Ser Leu Val Asn Arg Arg Pro Cys Phe Ser
            500                 505                 510

Ala Leu Thr Pro Asp Glu Thr Tyr Val Pro Lys Ala Phe Asp Glu Lys
        515                 520                 525

Leu Phe Thr Phe His Ala Asp Ile Cys Thr Leu Pro Asp Thr Glu Lys
        530                 535                 540

Gln Ile Lys Lys Gln Thr Ala Leu Val Glu Leu Leu Lys His Lys Pro
545                 550                 555                 560

Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
            580                 585                 590

Val Glu Gly Pro Lys Leu Val Val Ser Thr Gln Thr Ala Leu Ala
        595                 600                 605

<210> SEQ ID NO 11
<211> LENGTH: 563
<212> TYPE: PRT
<213> ORGANISM: Glycine max

<400> SEQUENCE: 11

Met Gly Lys Pro Phe Thr Leu Ser Leu Ser Ser Cys Leu Leu Leu
1                5                  10                  15

Leu Ser Ser Ala Cys Phe Ala Ile Ser Ser Ser Lys Leu Asn Glu Cys
                20                  25                  30

Gln Leu Asn Asn Leu Asn Ala Leu Glu Pro Asp His Arg Val Glu Ser
            35                  40                  45

Glu Gly Gly Leu Ile Gln Thr Trp Asn Ser Gln His Pro Glu Leu Lys
 50                  55                  60

Cys Ala Gly Val Thr Val Ser Lys Leu Thr Leu Asn Arg Asn Gly Leu
 65                  70                  75                  80

His Leu Pro Ser Tyr Ser Pro Tyr Pro Arg Met Ile Ile Ile Ala Gln
                85                  90                  95

Gly Lys Gly Ala Leu Gly Val Ala Ile Pro Gly Cys Pro Glu Thr Phe
            100                 105                 110

Glu Glu Pro Gln Glu Gln Ser Asn Arg Arg Gly Ser Arg Ser Gln Lys
        115                 120                 125

Gln Gln Leu Gln Asp Ser His Gln Lys Ile Arg His Phe Asn Glu Gly
    130                 135                 140

Asp Val Leu Val Ile Pro Pro Gly Val Pro Tyr Trp Thr Tyr Asn Thr
145                 150                 155                 160

Gly Asp Glu Pro Val Val Ala Ile Ser Leu Leu Asp Thr Ser Asn Phe
                165                 170                 175

Asn Asn Gln Leu Asp Gln Thr Pro Arg Val Phe Tyr Leu Ala Gly Asn
            180                 185                 190

Pro Asp Ile Glu Tyr Pro Glu Thr Met Gln Gln Gln Gln Gln Gln Lys
        195                 200                 205

Ser His Gly Gly Arg Lys Gln Gly Gln His Gln Glu Glu Glu Glu
    210                 215                 220

Glu Gly Gly Ser Val Leu Ser Gly Phe Ser Lys His Phe Leu Ala Gln
225                 230                 235                 240

Ser Phe Asn Thr Asn Glu Asp Ile Ala Glu Lys Leu Gln Ser Pro Asp
                245                 250                 255

Asp Glu Arg Lys Gln Ile Val Thr Val Glu Gly Gly Leu Ser Val Ile
            260                 265                 270
```

```
Ser Pro Lys Trp Gln Glu Gln Asp Glu Asp Glu Asp Glu
        275                 280                 285

Asp Asp Glu Asp Glu Gln Ile Pro Ser His Pro Arg Arg Pro Ser
        290                 295                 300

His Gly Lys Arg Glu Gln Asp Glu Asp Glu Asp Glu Asp Lys
305                 310                 315                 320

Pro Arg Pro Ser Arg Pro Ser Gln Gly Lys Arg Glu Gln Asp Gln
                325                 330                 335

Gln Asp Glu Asp Glu Asp Glu Asp Gln Pro Arg Lys Ser Arg
        340                 345                 350

Glu Trp Arg Ser Lys Thr Gln Pro Arg Arg Pro Arg Gln Glu Glu
        355                 360                 365

Pro Arg Glu Arg Gly Cys Glu Thr Arg Asn Gly Val Glu Glu Asn Ile
370                 375                 380

Cys Thr Leu Lys Leu His Glu Asn Ile Ala Arg Pro Ser Arg Ala Asp
385                 390                 395                 400

Phe Tyr Asn Pro Lys Ala Gly Arg Ile Ser Thr Leu Asn Ser Leu Thr
                405                 410                 415

Leu Pro Ala Leu Arg Gln Phe Gln Leu Ser Ala Gln Tyr Val Val Leu
        420                 425                 430

Tyr Lys Asn Gly Ile Tyr Ser Pro His Trp Asn Leu Asn Ala Asn Ser
        435                 440                 445

Val Ile Tyr Val Thr Arg Gly Gln Gly Lys Val Arg Val Asn Cys
        450                 455                 460

Gln Gly Asn Ala Val Phe Asp Gly Glu Leu Arg Arg Gly Gln Leu Leu
465                 470                 475                 480

Val Val Pro Gln Asn Phe Val Val Ala Glu Gln Ala Gly Glu Gln Gly
                485                 490                 495

Phe Glu Tyr Ile Val Phe Lys Thr His His Asn Ala Val Thr Ser Tyr
                500                 505                 510

Leu Lys Asp Val Phe Arg Ala Ile Pro Ser Glu Val Leu Ala His Ser
        515                 520                 525

Tyr Asn Leu Arg Gln Ser Gln Val Ser Glu Leu Lys Tyr Glu Gly Asn
        530                 535                 540

Trp Gly Pro Leu Val Asn Pro Glu Ser Gln Gln Gly Ser Pro Arg Val
545                 550                 555                 560

Lys Val Ala

<210> SEQ ID NO 12
<211> LENGTH: 639
<212> TYPE: PRT
<213> ORGANISM: Glycine max

<400> SEQUENCE: 12

Met Met Arg Ala Arg Phe Pro Leu Leu Leu Leu Gly Val Val Phe Leu
1               5                   10                  15

Ala Ser Val Ser Val Ser Phe Gly Ile Ala Tyr Trp Glu Lys Gln Asn
                20                  25                  30

Pro Ser His Asn Lys Cys Leu Arg Ser Cys Asn Ser Glu Lys Asp Ser
            35                  40                  45

Tyr Arg Asn Gln Ala Cys His Ala Arg Cys Asn Leu Leu Lys Val Glu
        50                  55                  60

Glu Glu Glu Glu Cys Glu Glu Gly Gln Ile Pro Arg Pro Arg Pro Gln
65                  70                  75                  80
```

```
His Pro Glu Arg Glu Arg Gln Gln His Gly Glu Lys Glu Glu Asp Glu
                85                  90                  95
Gly Glu Gln Pro Arg Pro Phe Pro Phe Pro Arg Pro Arg Gln Pro His
            100                 105                 110
Gln Glu Glu Glu His Glu Gln Lys Glu His Glu Trp His Arg Lys
        115                 120                 125
Glu Glu Lys His Gly Gly Lys Gly Ser Glu Glu Glu Gln Asp Glu Arg
    130                 135                 140
Glu His Pro Arg Pro His Gln Pro His Gln Lys Glu Glu Lys His
145                 150                 155                 160
Glu Trp Gln His Lys Gln Glu Lys His Gln Gly Lys Glu Ser Glu Glu
                165                 170                 175
Glu Glu Glu Asp Gln Asp Glu Asp Glu Glu Gln Asp Lys Glu Ser Gln
            180                 185                 190
Glu Ser Glu Gly Ser Glu Ser Gln Arg Glu Pro Arg Arg His Lys Asn
        195                 200                 205
Lys Asn Pro Phe His Phe Asn Ser Lys Arg Phe Gln Thr Leu Phe Lys
    210                 215                 220
Asn Gln Tyr Gly His Val Arg Val Leu Gln Arg Phe Asn Lys Arg Ser
225                 230                 235                 240
Gln Gln Leu Gln Asn Leu Arg Asp Tyr Arg Ile Leu Glu Phe Asn Ser
                245                 250                 255
Lys Pro Asn Thr Leu Leu Pro His His Ala Asp Ala Asp Tyr Leu
            260                 265                 270
Ile Val Ile Leu Asn Gly Thr Ala Ile Leu Thr Leu Val Asn Asn Asp
        275                 280                 285
Asp Arg Asp Ser Tyr Asn Leu Gln Ser Gly Asp Ala Leu Arg Val Pro
    290                 295                 300
Ala Gly Thr Thr Phe Tyr Val Val Asn Pro Asp Asn Asp Glu Asn Leu
305                 310                 315                 320
Arg Met Ile Ala Gly Thr Thr Phe Tyr Val Val Asn Pro Asp Asn Asp
                325                 330                 335
Glu Asn Leu Arg Met Ile Thr Leu Ala Ile Pro Val Asn Lys Pro Gly
            340                 345                 350
Arg Phe Glu Ser Phe Phe Leu Ser Ser Thr Gln Ala Gln Gln Ser Tyr
        355                 360                 365
Leu Gln Gly Phe Ser Lys Asn Ile Leu Glu Ala Ser Tyr Asp Thr Lys
    370                 375                 380
Phe Glu Glu Ile Asn Lys Val Leu Phe Gly Arg Glu Glu Gly Gln Gln
385                 390                 395                 400
Gln Gly Glu Glu Arg Leu Gln Glu Ser Val Ile Val Glu Ile Ser Lys
                405                 410                 415
Lys Gln Ile Arg Glu Leu Ser Lys His Ala Lys Ser Ser Arg Lys
            420                 425                 430
Thr Ile Ser Ser Glu Asp Lys Pro Phe Asn Leu Gly Ser Arg Asp Pro
        435                 440                 445
Ile Tyr Ser Asn Lys Leu Gly Lys Leu Phe Glu Ile Thr Gln Arg Asn
    450                 455                 460
Pro Gln Leu Arg Asp Leu Asp Val Phe Leu Ser Val Asp Met Asn
465                 470                 475                 480
Glu Gly Ala Leu Phe Leu Pro His Phe Asn Ser Lys Ala Ile Val Val
                485                 490                 495
```

-continued

```
Leu Val Ile Asn Glu Gly Glu Ala Asn Ile Glu Leu Val Gly Ile Lys
                500                 505                 510

Glu Gln Gln Arg Gln Gln Glu Gln Pro Leu Glu Val Arg
        515                 520                 525

Lys Tyr Arg Ala Glu Leu Ser Glu Gln Asp Ile Phe Val Ile Pro Ala
        530                 535                 540

Gly Tyr Pro Val Met Val Asn Ala Thr Ser Asp Leu Asn Phe Phe Ala
545                 550                 555                 560

Phe Gly Ile Asn Ala Glu Asn Asn Gln Arg Asn Phe Leu Ala Gly Ser
                565                 570                 575

Lys Asp Asn Val Ile Ser Gln Ile Pro Ser Gln Val Gln Glu Leu Ala
                580                 585                 590

Phe Pro Arg Ser Ala Lys Asp Ile Glu Asn Leu Ile Lys Ser Gln Ser
        595                 600                 605

Glu Ser Tyr Phe Val Asp Ala Gln Pro Gln Gln Lys Glu Glu Gly Asn
        610                 615                 620

Lys Gly Arg Lys Gly Pro Leu Ser Ser Ile Leu Arg Ala Phe Tyr
625                 630                 635

<210> SEQ ID NO 13
<211> LENGTH: 623
<212> TYPE: PRT
<213> ORGANISM: Glycine max

<400> SEQUENCE: 13

Met Arg Ala Arg Phe Pro Leu Leu Leu Leu Gly Val Val Phe Leu Ala
1               5                   10                  15

Ser Val Ser Val Ser Phe Gly Ile Ala Tyr Trp Glu Lys Gln Asn Pro
                20                  25                  30

Lys His Asn Lys Cys Leu Gln Ser Cys Asn Ser Glu Arg Asp Ser Tyr
            35                  40                  45

Arg Asn Gln Ala Cys His Ala Arg Cys Asn Leu Leu Lys Val Glu Lys
    50                  55                  60

Glu Glu Glu Cys Glu Glu Gly Glu Ile Pro Arg Pro Arg Pro Arg Pro
65                  70                  75                  80

Gln His Pro Glu Arg Glu Pro Gln Pro Gly Lys Glu Glu Asp
                85                  90                  95

Glu Asp Glu Gln Pro Arg Pro Ile Pro Phe Pro Arg Pro Arg Gln Pro
            100                 105                 110

Arg Gln Glu Glu Glu His Glu Gln Arg Glu Glu Gln Glu Trp Pro Arg
        115                 120                 125

Lys Glu Glu Lys Arg Gly Glu Lys Gly Ser Glu Glu Glu Gln Asp Gly
        130                 135                 140

Arg Glu His Pro Arg Pro His Gln Pro His Asp Glu Asp Glu Glu Gln
145                 150                 155                 160

Asp Glu Arg Gln Phe Pro Phe Pro Arg Pro Pro His Gln Lys Glu Ser
                165                 170                 175

Glu Glu Arg Lys Gln Glu Glu Asp Glu Asp Glu Gln Gln Arg Glu
            180                 185                 190

Ser Glu Glu Ser Glu Ser Ser Glu Ser Gln Arg Glu Leu Arg Arg His
        195                 200                 205

Lys Asn Lys Asn Pro Phe His Phe Gly Ser Asn Arg Phe Glu Thr Leu
        210                 215                 220

Phe Lys Asn Gln Tyr Gly Arg Ile Arg Val Leu Gln Arg Phe Asn Gln
225                 230                 235                 240
```

Arg Ser Pro Gln Leu Gln Asn Leu Arg Asp Tyr Arg Ile Leu Glu Phe
            245                 250                 255

Asn Ser Lys Pro Asn Thr Leu Leu Pro Asn His Ala Asp Ala Asp
            260                 265                 270

Tyr Leu Ile Ala Ile Leu Asn Gly Thr Ala Ile Leu Ser Leu Val Asn
            275                 280                 285

Asn Asp Asp Arg Asp Ser Tyr Arg Leu Gln Ser Gly Asp Ala Leu Arg
290                 295                 300

Val Pro Ser Gly Thr Thr Tyr Tyr Val Val Asn Pro Asp Asn Asn Glu
305                 310                 315                 320

Asn Leu Arg Leu Ile Thr Leu Ala Ile Pro Val Asn Lys Pro Gly Arg
            325                 330                 335

Phe Glu Ser Phe Phe Leu Ser Ser Thr Glu Ala Gln Gln Ser Tyr Leu
            340                 345                 350

Gln Gly Phe Ser Arg Asn Ile Leu Glu Ala Ser Tyr Asp Thr Lys Phe
            355                 360                 365

Glu Glu Ile Asn Lys Val Leu Phe Ser Arg Glu Gly Gln Gln Gln
            370                 375                 380

Gly Glu Gln Arg Leu Gln Glu Ser Val Ile Val Glu Ile Ser Lys Glu
385                 390                 395                 400

Gln Ile Arg Ala Leu Ser Lys Arg Ala Lys Ser Ser Ser Arg Lys Thr
            405                 410                 415

Ile Ser Ser Glu Asp Lys Pro Phe Asn Leu Arg Ser Arg Asp Pro Ile
            420                 425                 430

Tyr Ser Asn Lys Leu Gly Lys Phe Phe Glu Ile Thr Pro Glu Lys Asn
            435                 440                 445

Pro Gln Leu Arg Asp Leu Asp Ile Phe Leu Ser Ile Val Asp Met Asn
            450                 455                 460

Glu Gly Ala Leu Leu Leu Pro His Phe Asn Ser Lys Ala Ile Val Ile
465                 470                 475                 480

Leu Val Ile Asn Glu Gly Asp Ala Asn Ile Glu Leu Val Gly Leu Lys
            485                 490                 495

Glu Gln Gln Gln Glu Gln Gln Glu Glu Gln Pro Leu Glu Val Arg
            500                 505                 510

Lys Tyr Arg Ala Glu Leu Ser Glu Gln Asp Ile Phe Val Ile Pro Ala
            515                 520                 525

Gly Tyr Pro Val Val Val Asn Ala Thr Ser Asn Leu Asn Phe Phe Ala
            530                 535                 540

Ile Gly Ile Asn Ala Glu Asn Asn Gln Arg Asn Phe Leu Ala Gly Ser
545                 550                 555                 560

Gln Asp Asn Val Ile Ser Gln Ile Pro Ser Gln Val Gln Glu Leu Ala
            565                 570                 575

Phe Leu Gly Ser Ala Gln Ala Val Glu Lys Leu Leu Lys Asn Gln Arg
            580                 585                 590

Glu Ser Tyr Phe Val Asp Ala Gln Pro Lys Lys Lys Glu Glu Gly Asn
            595                 600                 605

Lys Gly Arg Lys Gly Pro Leu Ser Ser Ile Leu Arg Ala Phe Tyr
610                 615                 620

<210> SEQ ID NO 14
<211> LENGTH: 439
<212> TYPE: PRT
<213> ORGANISM: Glycine max

<400> SEQUENCE: 14

```
Met Met Arg Val Arg Phe Pro Leu Leu Val Leu Leu Gly Thr Val Phe
1               5                   10                  15

Leu Ala Ser Val Cys Val Ser Leu Lys Val Arg Glu Asp Glu Asn Asn
            20                  25                  30

Pro Phe Tyr Phe Arg Ser Ser Asn Ser Phe Gln Thr Leu Phe Glu Asn
        35                  40                  45

Gln Asn Val Arg Ile Arg Leu Leu Gln Arg Phe Asn Lys Arg Ser Pro
    50                  55                  60

Gln Leu Glu Asn Leu Arg Asp Tyr Arg Ile Val Gln Phe Gln Ser Lys
65                  70                  75                  80

Pro Asn Thr Ile Leu Leu Pro His His Ala Asp Ala Asp Phe Leu Leu
                85                  90                  95

Phe Val Leu Ser Gly Arg Ala Ile Leu Thr Leu Val Asn Asn Asp Asp
            100                 105                 110

Arg Asp Ser Tyr Asn Leu His Pro Gly Asp Ala Gln Arg Ile Pro Ala
        115                 120                 125

Gly Thr Thr Tyr Tyr Leu Val Asn Pro His Asp His Gln Asn Leu Lys
    130                 135                 140

Ile Ile Lys Leu Ala Ile Pro Val Asn Lys Pro Gly Arg Tyr Asp Asp
145                 150                 155                 160

Phe Phe Leu Ser Ser Thr Gln Ala Gln Gln Ser Tyr Leu Gln Gly Phe
                165                 170                 175

Ser His Asn Ile Leu Glu Thr Ser Phe His Ser Glu Phe Glu Glu Ile
            180                 185                 190

Asn Arg Val Leu Phe Gly Glu Glu Glu Gln Arg Gln Gln Glu Gly
        195                 200                 205

Val Ile Val Glu Leu Ser Lys Glu Gln Ile Arg Gln Leu Ser Arg Arg
    210                 215                 220

Ala Lys Ser Ser Arg Lys Thr Ile Ser Ser Glu Asp Glu Pro Phe
225                 230                 235                 240

Asn Leu Arg Ser Arg Asn Pro Ile Tyr Ser Asn Asn Phe Gly Lys Phe
                245                 250                 255

Phe Glu Ile Thr Pro Glu Lys Asn Pro Gln Leu Arg Asp Leu Asp Ile
            260                 265                 270

Phe Leu Ser Ser Val Asp Ile Asn Glu Gly Ala Leu Leu Leu Pro His
        275                 280                 285

Phe Asn Ser Lys Ala Ile Val Ile Leu Val Ile Asn Glu Gly Asp Ala
    290                 295                 300

Asn Ile Glu Leu Val Gly Ile Lys Glu Gln Gln Gln Lys Gln Lys Gln
305                 310                 315                 320

Glu Glu Glu Pro Leu Glu Val Gln Arg Tyr Arg Ala Glu Leu Ser Glu
                325                 330                 335

Asp Asp Val Phe Val Ile Pro Ala Ala Tyr Pro Phe Val Val Asn Ala
            340                 345                 350

Thr Ser Asn Leu Asn Phe Leu Ala Phe Gly Ile Asn Ala Glu Asn Asn
        355                 360                 365

Gln Arg Asn Phe Leu Ala Gly Glu Lys Asp Asn Val Val Arg Gln Ile
    370                 375                 380

Glu Arg Gln Val Gln Glu Leu Ala Phe Pro Gly Ser Ala Gln Asp Val
385                 390                 395                 400

Glu Arg Leu Leu Lys Lys Gln Arg Glu Ser Tyr Phe Val Asp Ala Gln
                405                 410                 415
```

```
Pro Gln Gln Lys Glu Glu Gly Ser Lys Gly Arg Lys Gly Pro Phe Pro
            420                 425                 430

Ser Ile Leu Gly Ala Leu Tyr
            435

<210> SEQ ID NO 15
<211> LENGTH: 288
<212> TYPE: PRT
<213> ORGANISM: Triticum sp.

<400> SEQUENCE: 15

Met Lys Thr Phe Leu Ile Leu Ala Leu Leu Ala Ile Val Ala Thr Thr
1               5                   10                  15

Ala Thr Thr Ala Val Arg Val Pro Val Pro Gln Leu Gln Pro Gln Asn
            20                  25                  30

Pro Ser Gln Gln Gln Pro Gln Glu Gln Val Pro Leu Val Gln Gln Gln
        35                  40                  45

Gln Phe Leu Gly Gln Gln Gln Pro Phe Pro Pro Gln Gln Pro Tyr Pro
    50                  55                  60

Gln Pro Gln Pro Phe Pro Ser Gln Gln Pro Tyr Leu Gln Leu Gln Pro
65                  70                  75                  80

Phe Pro Gln Pro Gln Leu Pro Tyr Ser Gln Pro Gln Pro Phe Arg Pro
                85                  90                  95

Gln Gln Pro Tyr Pro Gln Pro Gln Pro Gln Tyr Ser Gln Pro Gln Gln
            100                 105                 110

Pro Ile Ser Gln Gln Gln Gln Gln Gln Gln Gln Gln Gln Gln Gln Gln
        115                 120                 125

Gln Gln Gln Gln Gln Gln Ile Leu Gln Gln Ile Leu Gln Gln Gln
    130                 135                 140

Leu Ile Pro Cys Met Asp Val Val Leu Gln Gln His Asn Ile Ala His
145                 150                 155                 160

Gly Arg Ser Gln Val Leu Gln Gln Ser Thr Tyr Gln Leu Leu Gln Glu
                165                 170                 175

Leu Cys Cys Gln His Leu Trp Gln Ile Pro Glu Gln Ser Gln Cys Gln
            180                 185                 190

Ala Ile His Lys Val Val His Ala Ile Ile Leu His Gln Gln Gln Lys
        195                 200                 205

Gln Gln Gln Gln Pro Ser Ser Gln Val Ser Phe Gln Gln Pro Leu Gln
    210                 215                 220

Gln Tyr Pro Leu Gly Gln Gly Ser Phe Arg Pro Ser Gln Gln Asn Pro
225                 230                 235                 240

Gln Ala Gln Gly Ser Val Gln Pro Gln Gln Leu Pro Gln Phe Glu Glu
                245                 250                 255

Ile Arg Asn Leu Ala Leu Gln Thr Leu Pro Ala Met Cys Asn Val Tyr
            260                 265                 270

Ile Pro Pro Tyr Cys Thr Ile Thr Pro Phe Gly Ile Phe Gly Thr Asn
        275                 280                 285

<210> SEQ ID NO 16
<211> LENGTH: 302
<212> TYPE: PRT
<213> ORGANISM: Triticum sp.

<400> SEQUENCE: 16

Met Lys Thr Leu Leu Ile Leu Thr Ile Leu Ala Met Ala Thr Thr Ile
1               5                   10                  15
```

```
Ala Thr Ala Asn Met Gln Val Asp Pro Ser Gly Gln Val Gln Trp Pro
             20                  25                  30

Gln Gln Gln Pro Phe Pro Gln Pro Gln Gln Pro Phe Cys Gln Gln Pro
         35                  40                  45

Gln Arg Thr Ile Pro Gln Pro His Gln Thr Phe His His Gln Pro Gln
     50                  55                  60

Gln Thr Phe Pro Gln Pro Gln Gln Thr Tyr Pro His Gln Pro Gln Gln
 65                  70                  75                  80

Gln Phe Pro Gln Thr Gln Gln Pro Gln Gln Pro Phe Pro Gln Pro Gln
                 85                  90                  95

Gln Thr Phe Pro Gln Gln Pro Gln Leu Pro Phe Pro Gln Pro Gln Gln
                100                 105                 110

Gln Pro Phe Pro Gln Pro Gln Pro Gln Gln Pro Phe Pro Gln Ser
             115                 120                 125

Gln Gln Pro Gln Gln Pro Phe Pro Gln Pro Gln Gln Gln Phe Pro Gln
         130                 135                 140

Pro Gln Gln Pro Gln Gln Ser Phe Pro Gln Gln Gln Pro Ala Ile
145                 150                 155                 160

Gln Ser Phe Leu Gln Gln Met Asn Pro Cys Lys Asn Phe Leu Leu
                165                 170                 175

Gln Gln Cys Asn His Val Ser Leu Val Ser Ser Leu Val Ser Ile Ile
            180                 185                 190

Leu Pro Arg Ser Asp Cys Gln Val Met Gln Gln Cys Cys Gln Gln
        195                 200                 205

Leu Ala Gln Ile Pro Gln Gln Leu Gln Cys Ala Ala Ile His Ser Val
    210                 215                 220

Ala His Ser Ile Ile Met Gln Gln Glu Gln Gln Gln Gly Val Pro Ile
225                 230                 235                 240

Leu Arg Pro Leu Phe Gln Leu Ala Gln Gly Leu Gly Ile Ile Gln Pro
                245                 250                 255

Gln Gln Pro Ala Gln Leu Glu Gly Ile Arg Ser Leu Val Leu Lys Thr
            260                 265                 270

Leu Pro Thr Met Cys Asn Val Tyr Val Pro Pro Asp Cys Ser Thr Ile
        275                 280                 285

Asn Val Pro Tyr Ala Asn Ile Asp Ala Gly Ile Gly Gly Gln
    290                 295                 300

<210> SEQ ID NO 17
<211> LENGTH: 331
<212> TYPE: PRT
<213> ORGANISM: Triticum sp.

<400> SEQUENCE: 17

Met Lys Thr Phe Leu Ile Leu Ser Leu Leu Ala Ile Val Ala Thr Thr
1               5                   10                  15

Ala Thr Thr Ala Val Arg Phe Pro Val Pro Gln Leu Gln Pro Gln Asn
             20                  25                  30

Pro Ser Gln Gln Gln Pro Gln Glu Val Pro Leu Val Gln Gln Leu
         35                  40                  45

Gln Tyr Pro Gly Gln Gln Gln Pro Phe Pro Pro Gln Gln Pro Tyr Pro
     50                  55                  60

Gln Pro Gln Pro Phe Pro Ser Gln Gln Pro Leu Pro Gln Pro Gln Pro
 65                  70                  75                  80

Phe Leu Pro Gln Leu Pro Tyr Pro Gln Pro Gln Pro Phe Pro Pro Gln
```

```
                    85                  90                  95
Gln Pro Tyr Pro Gln Pro Gln Pro Gln Tyr Pro Gln Pro Gln Gln Pro
            100                 105                 110

Ile Ser Gln Gln Gln Ala Gln Ala Gln Gln Gln Gln Gln Gln
            115                 120                 125

Gln Gln Gln Gln Gln Gln Gln Gln Gln Gln Ile Leu Gln Gln Ile
130                 135                 140

Leu Gln Gln Gln Leu Ile Pro Cys Arg Asp Val Val Leu Gln Gln
145                 150                 155                 160

His Asn Ile Ala His Ala Ser Ser Gln Val Leu Gln Gln Ser Ser Tyr
                165                 170                 175

Gln Leu Leu Gln Gln Leu Cys Cys Gln Arg Leu Trp Gln Ile Pro Glu
                180                 185                 190

Gln Ser Arg Cys Gln Ala Ile His Asn Val Val His Ala Ile Ile Leu
                195                 200                 205

Gln Gln Gln Gln Gln Gln Gln Gln Gln Gln Gln Gln Gln Gln
            210                 215                 220

Gln Gln Gln Gln Gln Gln Gln Gln Gln Gln Gln Gln Gln Gln Gln Gln
225                 230                 235                 240

Gln Gln Gln Gln Gln Gln Gln Gln Gln Gln Gln Pro Ser Ser
                245                 250                 255

Gln Val Ser Tyr Gln Gln Pro Gln Gln Tyr Pro Ser Gly Gln Gly
            260                 265                 270

Ser Phe Gln Pro Ser Gln Gln Asn Pro Gln Ala Gln Ala Ser Val Gln
            275                 280                 285

Pro Gln Gln Leu Pro Gln Phe Glu Glu Ile Arg Asn Leu Ala Arg Gln
            290                 295                 300

Thr Leu Pro Ala Met Cys Asn Val Tyr Ile Pro Pro Tyr Cys Ser Thr
305                 310                 315                 320

Thr Ile Ala Pro Ser Gly Ile Phe Gly Thr Asn
                325                 330

<210> SEQ ID NO 18
<211> LENGTH: 439
<212> TYPE: PRT
<213> ORGANISM: Triticum sp.

<400> SEQUENCE: 18

Met Lys Thr Phe Ile Ile Phe Val Leu Leu Ala Met Ala Met Asn Ile
1               5                   10                  15

Ala Ser Ala Ser Arg Leu Leu Ser Pro Arg Gly Lys Glu Leu His Thr
                20                  25                  30

Pro Gln Glu Gln Phe Pro Gln Gln Gln Phe Pro Gln Pro Gln Gln
            35                  40                  45

Phe Pro Gln Gln Gln Ile Pro Gln Gln His Gln Ile Pro Gln Pro
    50                  55                  60

Gln Gln Phe Pro Gln Gln Gln Phe Leu Gln Gln Gln Ile Pro
65                  70                  75                  80

Gln Gln Gln Ile Pro Gln Gln His Gln Ile Pro Gln Gln Pro Gln Gln
                85                  90                  95

Phe Pro Gln Gln Gln Phe Pro Gln Gln His Gln Ser Pro Gln Gln
            100                 105                 110

Gln Phe Pro Gln Gln Gln Phe Pro Gln Gln Lys Leu Pro Gln Gln Glu
            115                 120                 125
```

```
Phe Pro Gln Gln Gln Ile Ser Gln Gln Pro Gln Gln Leu Pro Gln Gln
    130                 135                 140

Gln Gln Ile Pro Gln Gln Pro Gln Gln Phe Leu Gln Gln Gln Gln Phe
145                 150                 155                 160

Pro Gln Gln Gln Pro Pro Gln Gln His Gln Phe Pro Gln Gln Gln Leu
                165                 170                 175

Pro Gln Gln Gln Gln Ile Pro Gln Gln Gln Ile Pro Gln Gln Pro
            180                 185                 190

Gln Gln Ile Pro Gln Gln Gln Ile Pro Gln Gln Pro Gln Gln Phe
            195                 200                 205

Pro Gln Gln Gln Phe Pro Gln Gln Gln Phe Pro Gln Gln Gln Phe Pro
    210                 215                 220

Gln Gln Glu Phe Pro Gln Gln Gln Phe Pro Gln Gln Gln Ile Ala
225                 230                 235                 240

Arg Gln Pro Gln Gln Leu Pro Gln Gln Gln Ile Pro Gln Gln Pro
                245                 250                 255

Gln Gln Phe Pro Gln Gln Gln Phe Pro Gln Gln Ser Pro Gln
                260                 265                 270

Gln Gln Gln Phe Pro Gln Gln Gln Phe Pro Gln Gln Gln Leu Pro
            275                 280                 285

Gln Lys Gln Phe Pro Gln Pro Gln Gln Ile Pro Gln Gln Gln Ile
    290                 295                 300

Pro Gln Gln Pro Gln Gln Phe Pro Gln Gln Gln Phe Pro Gln Gln Gln
305                 310                 315                 320

Gln Phe Pro Gln Gln Gln Glu Phe Pro Gln Gln Phe Pro Gln Gln
                325                 330                 335

Gln Phe His Gln Gln Gln Leu Pro Gln Gln Gln Phe Pro Gln Gln Gln
                340                 345                 350

Phe Pro Gln Gln Gln Phe Pro Gln Gln Gln Phe Pro Gln Gln Gln
                355                 360                 365

Gln Leu Thr Gln Gln Phe Pro Arg Pro Gln Gln Ser Pro Glu Gln
    370                 375                 380

Gln Gln Phe Pro Gln Gln Gln Phe Pro Gln Gln Pro Pro Gln Gln Phe
385                 390                 395                 400

Pro Gln Gln Gln Phe Pro Ile Pro Tyr Pro Pro Gln Ser Glu Glu
                405                 410                 415

Pro Ser Pro Tyr Gln Gln Tyr Pro Gln Gln Pro Ser Gly Ser Asp
                420                 425                 430

Val Ile Ser Ile Ser Gly Leu
            435

<210> SEQ ID NO 19
<211> LENGTH: 1025
<212> TYPE: PRT
<213> ORGANISM: Triticum sp.

<400> SEQUENCE: 19

Met Ala Lys Arg Leu Val Leu Phe Val Ala Val Val Ala Leu Val
1               5                   10                  15

Ala Leu Thr Val Ala Glu Gly Glu Ala Ser Glu Gln Leu Gln Cys Glu
                20                  25                  30

Arg Glu Leu Gln Glu Leu Gln Glu Arg Glu Leu Lys Ala Cys Gln Gln
                35                  40                  45

Val Met Asp Gln Gln Leu Arg Asp Ile Ser Pro Glu Cys His Pro Val
50                  55                  60
```

-continued

```
Val Val Ser Pro Val Ala Gly Gln Tyr Glu Gln Ile Val Val Pro
 65              70                  75                  80

Pro Lys Gly Gly Ser Phe Tyr Pro Gly Glu Thr Thr Pro Pro Gln Gln
                 85                  90                  95

Leu Gln Gln Arg Ile Phe Trp Gly Ile Pro Ala Leu Leu Lys Arg Tyr
                100                 105                 110

Tyr Pro Ser Val Thr Ser Pro Gln Gln Val Ser Tyr Tyr Pro Gly Gln
                115                 120                 125

Ala Ser Pro Gln Arg Pro Gly Gln Gln Gln Pro Gly Gln Gly Gln
130                 135                 140

Gln Ser Gly Gln Gly Gln Gly Tyr Tyr Pro Thr Ser Pro Gln Gln
145                 150                 155                 160

Pro Gly Gln Trp Gln Gln Pro Glu Gln Gly Gln Pro Gly Tyr Tyr Pro
                165                 170                 175

Thr Ser Pro Gln Gln Pro Gly Gln Leu Gln Gln Pro Ala Gln Gly Gln
                180                 185                 190

Gln Pro Gly Gln Gly Gln Gly Arg Gln Pro Gly Gln Gly Gln Pro
                195                 200                 205

Gly Tyr Tyr Pro Thr Ser Ser Gln Leu Gln Pro Gly Gln Leu Gln Gln
210                 215                 220

Pro Ala Gln Gly Gln Gly Gln Gln Pro Gly Gln Gly Gln Gln Gly
225                 230                 235                 240

Gln Gln Pro Gly Gln Gly Gln Pro Gly Gln Gly Gln Gln Gly
                245                 250                 255

Gln Pro Gly Gln Gly Gln Pro Gly Gln Gly Gln Gln Gly Gln Gln
                260                 265                 270

Leu Gly Gln Gly Gln Gly Tyr Tyr Pro Thr Ser Leu Gln Gln Ser
                275                 280                 285

Gly Gln Gly Gln Pro Gly Tyr Tyr Pro Thr Ser Leu Gln Gln Leu Gly
290                 295                 300

Gln Gly Gln Ser Gly Tyr Tyr Pro Thr Ser Pro Gln Gln Pro Gly Gln
305                 310                 315                 320

Gly Gln Gln Pro Gly Gln Leu Gln Gln Pro Ala Gln Gly Gln Gln Pro
                325                 330                 335

Glu Gln Gly Gln Gln Gly Gln Gln Pro Gly Gln Gly Gln Gln Gly Gln
                340                 345                 350

Gln Pro Gly Gln Gly Gln Gln Pro Gly Gln Gly Gln Pro Gly Tyr Tyr
                355                 360                 365

Pro Thr Ser Pro Gln Gln Ser Gly Gln Gly Gln Pro Gly Tyr Tyr Pro
                370                 375                 380

Thr Ser Ser Gln Gln Pro Thr Gln Ser Gln Gln Pro Gly Gln Gly Gln
385                 390                 395                 400

Gln Gly Gln Gln Val Gly Gln Gly Gln Ala Gln Gln Pro Gly Gln
                405                 410                 415

Gly Gln Gln Pro Gly Gln Gly Gln Pro Gly Tyr Tyr Pro Thr Ser Pro
                420                 425                 430

Leu Gln Ser Gly Gln Gln Pro Gly Tyr Tyr Leu Thr Ser Pro Gln
                435                 440                 445

Gln Ser Gly Gln Gly Gln Pro Gly Gln Leu Gln Gln Ser Ala Gln
                450                 455                 460

Gly Gln Lys Gly Gln Gln Pro Gly Gln Gly Gln Pro Gly Gln Gly
465                 470                 475                 480
```

```
Gln Gln Gly Gln Gln Pro Gly Gln Gly Gln Gly Gln Pro Gly
            485                 490                 495

Gln Gly Gln Pro Gly Tyr Tyr Pro Thr Ser Pro Gln Ser Gly Gln
        500                 505                 510

Gly Gln Gln Pro Gly Gln Trp Gln Gln Pro Gly Gln Gly Gln Pro Gly
        515                 520                 525

Tyr Tyr Pro Thr Ser Pro Leu Gln Pro Gly Gln Gly Gln Pro Gly Tyr
        530                 535                 540

Asp Pro Thr Ser Pro Gln Gln Pro Gly Gln Gly Gln Pro Gly Gln
545                 550                 555                 560

Leu Gln Gln Pro Ala Gln Gly Gln Gly Gln Gln Leu Ala Gln Gly
                565                 570                 575

Gln Gln Gly Gln Gln Pro Ala Gln Val Gln Gly Gln Gln Pro Ala
            580                 585                 590

Gln Gly Gln Gln Gly Gln Gln Leu Gly Gln Gln Gln Gly Gln Gln
        595                 600                 605

Pro Gly Gln Gly Gln Gln Pro Ala Gln Gly Gln Gln Gly Gln Gln Pro
    610                 615                 620

Gly Gln Gly Gln Gln Gly Gln Gln Pro Gly Gln Gly Gln Gln Pro Gly
625                 630                 635                 640

Gln Gly Gln Pro Trp Tyr Tyr Pro Thr Ser Pro Gln Glu Ser Gly Gln
            645                 650                 655

Gly Gln Gln Pro Gly Gln Trp Gln Gln Pro Gly Gln Trp Gln Pro
        660                 665                 670

Gly Gln Gly Gln Gln Gly Gln Gln Pro Gly Gln Gly Gln Pro Gly Tyr
        675                 680                 685

Tyr Pro Thr Ser Pro Gln Gln Ser Gly Gln Gly Gln Pro Gly Gln
        690                 695                 700

Trp Gln Gln Pro Gly Gln Gly Gln Pro Gly Tyr Tyr Pro Thr Ser Pro
705                 710                 715                 720

Leu Gln Pro Gly Gln Gly Gln Pro Gly Tyr Asp Pro Thr Ser Pro Gln
                725                 730                 735

Gln Pro Gly Gln Gly Gln Gln Pro Gly Gln Leu Gln Gln Pro Ala Gln
            740                 745                 750

Gly Gln Gln Gly Gln Gln Leu Ala Gln Gly Gln Gly Gln Gln Pro
        755                 760                 765

Ala Gln Val Gln Gly Gln Gln Pro Ala Gln Gly Gln Gln Gly Gln
        770                 775                 780

Gln Leu Gly Gln Gln Gln Gly Gln Gln Pro Gly Gln Gly Gln Gln
785                 790                 795                 800

Pro Ala Gln Gly Gln Gln Gly Gln Gln Pro Gly Gln Gly Gln Gln Gly
                805                 810                 815

Gln Gln Pro Gly Gln Gly Gln Gln Pro Gly Gln Gly Gln Pro Trp Tyr
            820                 825                 830

Tyr Pro Thr Ser Pro Gln Glu Ser Gly Gln Gly Gln Pro Gly Gln
        835                 840                 845

Trp Gln Gln Pro Gly Gln Trp Gln Pro Gly Gln Gly Gln Pro Gly
850                 855                 860

Tyr Tyr Leu Thr Ser Pro Leu Gln Leu Gly Gln Gly Gln Gly Tyr
865                 870                 875                 880

Tyr Pro Thr Ser Leu Gln Gln Pro Gly Gln Gly Gln Pro Gly Gln
        885                 890                 895

Trp Gln Gln Ser Gly Gln Gly Gln His Gly Tyr Tyr Pro Thr Ser Pro
```

```
              900                 905                 910
Gln Leu Ser Gly Gln Gly Gln Arg Pro Gly Gln Trp Leu Gln Pro Gly
            915                 920                 925
Gln Gly Gln Gln Gly Tyr Tyr Pro Thr Ser Pro Gln Gln Ser Gly Gln
            930                 935                 940
Gly Gln Gln Leu Gly Gln Trp Leu Gln Pro Gly Gln Gly Gln Gln Gly
945                 950                 955                 960
Tyr Tyr Pro Thr Ser Leu Gln Gln Thr Gly Gln Gly Gln Gln Ser Gly
                965                 970                 975
Gln Gly Gln Gln Gly Tyr Tyr Ser Ser Tyr His Val Ser Val Glu His
            980                 985                 990
Gln Ala Ala Ser Leu Lys Val Ala Lys Ala Gln Gln Leu Ala Ala Gln
            995                 1000                1005
Leu Pro Ala Met Cys Arg Leu Glu Gly Gly Asp Ala Leu Ser Ala
    1010                1015                1020
Ser Gln
    1025

<210> SEQ ID NO 20
<211> LENGTH: 392
<212> TYPE: PRT
<213> ORGANISM: Triticum sp.

<400> SEQUENCE: 20

Met Lys Thr Phe Leu Ile Phe Ala Leu Leu Ala Val Ala Ala Thr Ser
1               5                   10                  15
Ala Ile Ala Gln Met Glu Asn Ser His Ile Pro Gly Leu Glu Arg Pro
            20                  25                  30
Ser Gln Gln Gln Pro Leu Pro Pro Gln Gln Thr Leu Ser His His Gln
        35                  40                  45
Gln Gln Gln Pro Ile Gln Gln Gln Pro His Gln Phe Pro Gln Gln Gln
    50                  55                  60
Pro Cys Ser Gln Gln Gln Gln Pro Pro Leu Ser Gln Gln Gln Gln Gln
65                  70                  75                  80
Pro Pro Phe Ser Gln Gln Gln Pro Pro Phe Ser Gln Gln Gln Gln Gln
                85                  90                  95
Pro Val Leu Pro Gln Gln Pro Ser Phe Ser Gln Gln Gln Leu Pro Pro
            100                 105                 110
Phe Ser Gln Gln Gln Gln Pro Pro Phe Ser Gln Gln Gln Gln Pro Val
        115                 120                 125
Leu Pro Gln Gln Pro Ser Phe Ser Gln Gln Gln Leu Pro Pro Phe Ser
    130                 135                 140
Gln Gln Leu Pro Pro Phe Leu Gln Gln Gln Pro Val Leu Pro Gln
145                 150                 155                 160
Gln Pro Pro Phe Ser Gln Gln Gln Leu Pro Pro Phe Ser Gln Gln Leu
                165                 170                 175
Pro Pro Phe Ser Gln Gln Gln Pro Val Leu Pro Gln Gln Pro Pro
            180                 185                 190
Phe Ser Gln Gln Gln Gln Pro Ile Leu Pro Gln Gln Pro Pro Phe
        195                 200                 205
Ser Gln Gln Gln Pro Val Leu Leu Gln Gln Gln Ile Pro Phe Val
    210                 215                 220
His Pro Ser Ile Leu Gln Gln Leu Asn Pro Cys Lys Val Phe Leu Gln
225                 230                 235                 240
```

-continued

```
Gln Gln Cys Ser Pro Val Ala Met Pro Gln Ser Leu Ala Arg Ser Gln
                245                 250                 255

Met Leu Gln Gln Arg Ser Cys His Val Met Gln Gln Cys Cys Gln
        260                 265                 270

Gln Leu Pro Gln Ile Pro Gln Gln Ser Arg Tyr Glu Ala Ile Arg Ala
        275                 280                 285

Ile Val Tyr Ser Ile Ile Leu Gln Glu Gln Gln Val Gln Gly Ser
290                 295                 300

Ile Gln Thr Gln Gln Gln Pro Gln Gln Leu Gly Gln Cys Val Ser
305                 310                 315                 320

Gln Pro Gln Gln Leu Gln Gln Leu Gly Gln Gln Pro Gln Gln
        325                 330                 335

Gln Gln Leu Ala Gln Gly Thr Phe Leu Gln Pro His Gln Ile Ala Gln
        340                 345                 350

Leu Glu Val Met Thr Ser Ile Ala Leu Arg Thr Leu Pro Thr Met Cys
        355                 360                 365

Asn Val Asn Val Pro Leu Tyr Arg Thr Thr Arg Val Pro Phe Gly
        370                 375                 380

Val Gly Thr Gly Val Gly Gly Tyr
385                 390

<210> SEQ ID NO 21
<211> LENGTH: 1912
<212> TYPE: PRT
<213> ORGANISM: Gallus gallus

<400> SEQUENCE: 21

Met Arg Gly Leu Ile Ser Ala Leu Val Leu Thr Leu Val Gly Ser Gln
1               5                   10                  15

His Leu Asn Tyr Gln Pro Asp Phe Gly Glu Asn Lys Val Tyr Thr Tyr
            20                  25                  30

Asn Tyr Glu Ser Ile Leu Phe Ser Gly Ile Pro Glu Lys Gly Leu Ala
        35                  40                  45

Arg Thr Gly Ile Arg Ile Arg Ser Glu Val Glu Ile Ser Gly Ile Gly
    50                  55                  60

Pro Lys Leu Cys Leu Ile Arg Ile His Ser Ile Glu Ala Ala Glu Tyr
65                  70                  75                  80

Asn Gly Ile Trp Pro Thr Ser Ser Phe Ser Arg Ser Leu Lys Leu Thr
                85                  90                  95

Gln Ala Leu Thr Gly Gln Leu Ser Ile Pro Ile Lys Phe Glu Tyr Ser
            100                 105                 110

Asn Gly His Val Gly Asn Leu Met Ala Pro Asp Ser Val Ser Asp Asp
        115                 120                 125

Gly Leu Asn Ile Tyr Arg Gly Ile Leu Asn Ile Leu Glu Leu Ser Leu
    130                 135                 140

Lys Lys Met Gln His Ser Tyr Ser Ile Gln Glu Ala Gly Ile Gly Gly
145                 150                 155                 160

Ile Cys Asn Thr Thr Tyr Ala Ile Gln Glu Asn Lys Lys Ala Asn Leu
                165                 170                 175

Val Asp Val Thr Lys Ser Lys Asp Leu Asn Ser Cys Glu Glu Lys Val
            180                 185                 190

Gln Val Val Thr Gly Ser Ala Tyr Thr Gln Pro Cys Gln Thr Cys Gln
        195                 200                 205

Gln Arg Asn Lys Asn Ser Arg Ala Thr Ala Thr Tyr Asn Tyr Lys Ile
    210                 215                 220
```

```
Lys Tyr Thr His Asn Glu Ala Val Ile Thr Gln Ala Glu Val Glu Glu
225                 230                 235                 240

Val His Gln Phe Thr Pro Phe His Glu Ile Thr Gly Gly Asn Ala Ile
                245                 250                 255

Val Glu Ala Arg Gln Lys Leu Ala Leu Ile Glu Val Gln Lys Gln Val
            260                 265                 270

Ala Glu Val Pro Pro Lys Glu Phe Gln Lys Arg Gly Ser Leu Gln Tyr
        275                 280                 285

Gln Phe Gly Ser Glu Leu Leu Gln Leu Pro Val His Leu Phe Lys Ile
290                 295                 300

Lys Asp Val Glu Arg Gln Ile Glu Glu Arg Leu Gln Asp Leu Val Glu
305                 310                 315                 320

Thr Thr Tyr Glu Gln Leu Pro Ser Asp Ala Pro Ala Lys Ala Leu Lys
                325                 330                 335

Leu Met His Leu Leu Arg Ala Ala Asn Glu Glu Asn Tyr Glu Ser Val
                340                 345                 350

Trp Lys Gln Phe Ser Ser Arg Pro Ala Tyr Arg Arg Tyr Leu Leu Asp
            355                 360                 365

Leu Leu Pro Ala Ala Ser His Arg Ser Leu Arg Phe Leu Arg His
370                 375                 380

Lys Met Glu Arg Gln Glu Leu Thr Asn Trp Glu Ile Ala Gln Thr Val
385                 390                 395                 400

Leu Val Ala Leu His Ser Ser Pro Thr Gln Glu Val Met Glu Glu
                405                 410                 415

Ala Thr Leu Ile Val Lys Lys His Cys Pro Arg Ser Ser Ser Val Leu
                420                 425                 430

Arg Lys Val Cys Leu Leu Ser Tyr Ala Ser Leu Cys His Lys Arg Cys
            435                 440                 445

Ser Ser Pro Tyr Ser Cys Ser Glu Cys Leu Gln Val Phe His Val Phe
    450                 455                 460

Ala Gly Glu Ala Leu Gly Lys Ser Asn Ile Glu Glu Val Leu Leu Ala
465                 470                 475                 480

Leu Lys Ala Leu Gly Asn Val Gly His Pro Ala Ser Ile Lys His Ile
                485                 490                 495

Lys Lys Phe Leu Pro Gly Tyr Ala Ala Gly Ala Ser Glu Leu Pro Leu
            500                 505                 510

Lys Val His Glu Thr Ala Val Met Ala Leu Lys Ser Ile Gly Met Arg
    515                 520                 525

Asp Pro Gln Met Val Gln Ala Ile Thr Leu Glu Ile Phe Leu Asn His
    530                 535                 540

Lys Ile His Pro Arg Ile Arg Met Leu Ala Ala Val Val Leu Leu Glu
545                 550                 555                 560

Thr Lys Pro Gly Leu Pro Ile Leu Met Ile Leu Val Asp Ala Val Leu
                565                 570                 575

Lys Glu Pro Ser Met Gln Val Ala Ser Phe Ile Tyr Ser His Leu Arg
                580                 585                 590

Ala Leu Gly Arg Ser Thr Ala Pro Asp Leu Gln Met Met Ala Ser Ala
            595                 600                 605

Cys Arg Met Ala Val Arg Ala Leu Ser Pro Lys Phe Asp Arg Ser Gly
        610                 615                 620

Tyr Gln Phe Ser Lys Val Phe Arg Phe Ser Met Phe Lys Glu Phe Leu
625                 630                 635                 640
```

```
Met Ser Gly Leu Ala Ala Lys Tyr Phe Val Leu Asn Asn Ala Gly Ser
            645                 650                 655
Leu Ile Pro Thr Met Ala Val Ser Gln Leu Arg Thr His Phe Leu Gly
            660                 665                 670
Arg Val Ala Asp Pro Ile Glu Val Gly Ile Ala Ala Glu Gly Leu Gln
            675                 680                 685
Glu Met Phe Val Arg Gly Tyr Ser Pro Asp Lys Asp Trp Glu Thr Asn
            690                 695                 700
Tyr Asp Phe Arg Glu Ile Leu Lys Lys Leu Ser Asp Trp Lys Ala Leu
705                 710                 715                 720
Pro Arg Asp Lys Pro Phe Ala Ser Gly Tyr Leu Lys Met Phe Gly Gln
            725                 730                 735
Glu Leu Leu Phe Gly Arg Leu Asp Lys Asp Thr Leu Gln Asn Val Leu
            740                 745                 750
Gln Val Trp Tyr Gly Pro Asp Glu Lys Ile Pro Ser Ile Arg Arg Leu
            755                 760                 765
Ile Ser Ser Leu Gln Thr Gly Ile Gly Arg Gln Trp Thr Lys Ala Leu
            770                 775                 780
Leu Leu Ser Glu Ile Arg Cys Ile Val Pro Thr Cys Val Gly Phe Pro
785                 790                 795                 800
Met Glu Thr Ser Phe Tyr Tyr Ser Ser Val Thr Lys Val Ala Gly Asn
            805                 810                 815
Val Gln Ala Gln Ile Thr Pro Ser Pro Arg Ser Asp Phe Arg Leu Thr
            820                 825                 830
Glu Leu Leu Asn Ser Asn Val Arg Leu Arg Ser Lys Met Ser Leu Ser
            835                 840                 845
Met Ala Lys His Met Thr Phe Val Ile Gly Ile Asn Thr Asn Met Ile
850                 855                 860
Gln Ala Gly Leu Glu Ala His Thr Lys Val Asn Ala His Val Pro Val
865                 870                 875                 880
Asn Val Val Ala Thr Ile Gln Met Lys Glu Lys Ser Ile Lys Ala Glu
            885                 890                 895
Ile Pro Pro Cys Lys Glu Glu Thr Asn Leu Ile Ile Val Ser Ser Lys
            900                 905                 910
Thr Phe Ala Val Thr Arg Asn Ile Glu Asp Leu Ala Ala Ser Lys Met
            915                 920                 925
Thr Pro Val Leu Leu Pro Glu Ala Val Pro Asp Ile Met Lys Met Ser
            930                 935                 940
Phe Asp Ser Asp Ser Ala Ser Gly Glu Thr Asp Asn Ile Arg Asp Arg
945                 950                 955                 960
Gln Ser Val Glu Asp Val Ser Ser Gly Asn Ser Phe Ser Phe Gly His
            965                 970                 975
Pro Ser Ser Gly Lys Glu Pro Phe Ile Gln Ser Met Cys Ser Asn Ala
            980                 985                 990
Ser Thr Phe Gly Val Gln Val Cys Ile Glu Lys Lys Ser Val His Ala
            995                 1000                1005
Ala Phe Ile Arg Asn Val Pro Leu Tyr Asn Ala Ile Gly Glu His
            1010                1015                1020
Ala Leu Arg Met Ser Phe Lys Pro Val Tyr Ser Asp Val Pro Ile
            1025                1030                1035
Glu Lys Ile Gln Val Thr Ile Gln Ala Gly Asp Gln Ala Pro Thr
            1040                1045                1050
Lys Met Val Arg Leu Val Thr Phe Glu Asp Pro Glu Arg Gln Glu
```

-continued

```
          1055                1060                1065

Ser  Ser  Arg  Lys  Glu  Val  Met  Lys  Arg  Val  Lys  Lys  Ile  Leu  Asp
          1070                1075                1080

Asp  Thr  Asp  Asn  Gln  Ala  Thr  Arg  Asn  Ser  Arg  Ser  Ser  Ser  Ser
          1085                1090                1095

Ser  Ala  Ser  Ser  Ile  Ser  Glu  Ser  Ser  Glu  Ser  Thr  Thr  Ser  Thr
          1100                1105                1110

Pro  Ser  Ser  Ser  Asp  Ser  Asp  Asn  Arg  Ala  Ser  Gln  Gly  Asp  Pro
          1115                1120                1125

Gln  Ile  Asn  Leu  Lys  Ser  Arg  Gln  Ser  Lys  Ala  Asn  Glu  Lys  Lys
          1130                1135                1140

Phe  Tyr  Pro  Phe  Gly  Asp  Ser  Ser  Ser  Gly  Ser  Ser  Ser  Ser
          1145                1150                1155

Ser  Ser  Ser  Ser  Ser  Ser  Ser  Ser  Ser  Asp  Ser  Ser  Ser  Ser
          1160                1165                1170

Arg  Ser  Ser  Ser  Ser  Asp  Ser  Ser  Ser  Ser  Ser  Ser  Ser
          1175                1180                1185

Ser  Ser  Ser  Ser  Ser  Ser  Lys  Ser  Lys  Ser  Ser  Ser  Arg  Ser  Ser
          1190                1195                1200

Lys  Ser  Asn  Arg  Ser  Ser  Ser  Ser  Asn  Ser  Lys  Asp  Ser  Ser
          1205                1210                1215

Ser  Ser  Ser  Ser  Lys  Ser  Asn  Ser  Lys  Gly  Ser  Ser  Ser  Ser  Ser
          1220                1225                1230

Ser  Lys  Ala  Ser  Gly  Thr  Arg  Gln  Lys  Ala  Lys  Lys  Gln  Ser  Lys
          1235                1240                1245

Thr  Thr  Ser  Phe  Pro  His  Ala  Ser  Ala  Ala  Glu  Gly  Glu  Arg  Ser
          1250                1255                1260

Val  His  Glu  Gln  Lys  Gln  Gly  Thr  Gln  Ser  Ser  Ser  Ser  Ser
          1265                1270                1275

Ser  Arg  Ala  Ser  Ser  Asn  Ser  Arg  Ser  Thr  Ser  Ser  Ser  Thr  Ser
          1280                1285                1290

Ser  Ser  Ser  Glu  Ser  Ser  Gly  Val  Ser  His  Arg  Gln  Trp  Lys  Gln
          1295                1300                1305

Asp  Arg  Glu  Ala  Glu  Thr  Lys  Arg  Val  Lys  Ser  Gln  Phe  Asn  Ser
          1310                1315                1320

His  Ser  Ser  Tyr  Asp  Ile  Pro  Asn  Glu  Trp  Glu  Thr  Tyr  Leu  Pro
          1325                1330                1335

Lys  Val  Tyr  Arg  Leu  Arg  Phe  Arg  Ser  Ala  His  Thr  His  Trp  His
          1340                1345                1350

Ser  Gly  His  Arg  Thr  Ser  Ser  Ser  Ser  Ser  Ser  Ser  Ser  Ser  Glu
          1355                1360                1365

Ser  Gly  Ser  Ser  His  Ser  Asn  Ser  Ser  Ser  Ser  Asp  Ser  Ser  Ser
          1370                1375                1380

Arg  Arg  Ser  His  Met  Ser  Asp  Ser  Ser  Ser  Ser  Ser  Ser  Ser  His
          1385                1390                1395

Arg  His  Gly  Glu  Lys  Ala  Ala  His  Ser  Ser  Arg  Arg  Ser  Pro  Thr
          1400                1405                1410

Ser  Arg  Ala  Ala  Ser  Ala  His  His  Arg  Pro  Gly  Ser  Ser  Leu  Thr
          1415                1420                1425

Arg  Glu  Arg  Asn  Phe  Leu  Gly  Asp  Val  Ile  Pro  Pro  Gly  Ile  Thr
          1430                1435                1440

Ile  Val  Ala  Gln  Ala  Val  Arg  Ser  Asp  Asn  Arg  Asn  Gln  Gly  Tyr
          1445                1450                1455
```

-continued

```
Gln Ala Thr Ala Tyr Val Arg Ser Asp Ala Ala Lys Val Asp Val
1460                1465                1470

Gln Leu Val Val Val Gln Leu Ala Glu Thr Asn Trp Lys Ala Cys
1475                1480                1485

Ala Asp Ala Val Ile Leu Pro Leu Lys Ala Gln Ala Arg Met Arg
1490                1495                1500

Trp Gly Lys Glu Cys Arg Asp Tyr Arg Ile Ala Ala Leu Ala Thr
1505                1510                1515

Thr Gly Gln Met Ala Arg Lys Leu Ala Val Gln Leu Lys Val Gln
1520                1525                1530

Trp Gly Ile Ile Pro Ser Trp Ile Lys Lys Thr Ser Thr Ala Leu
1535                1540                1545

Met Arg Tyr Val Pro Gly Val Ala Leu Val Leu Gly Phe Ser Glu
1550                1555                1560

Ala His Gln Arg Asn Pro Ser Arg Glu Leu Ile Val Arg Ala Val
1565                1570                1575

Ala Thr Ser Pro Arg Ser Ile Asp Thr Val Ile Lys Val Pro Gly
1580                1585                1590

Val Thr Leu Tyr Tyr Gln Gly Leu Arg Val Pro Phe Thr Leu Ala
1595                1600                1605

Leu Gly Ala Ser Ser Ser Tyr Glu Thr Arg Asp Ile Thr Ala
1610                1615                1620

Trp Asn Phe Leu Pro Glu Ile Ala Ser Gln Ile Ala Gln Glu Asp
1625                1630                1635

Gln Ser Thr Cys Glu Val Ser Lys Gly Asp Phe Lys Thr Phe Asp
1640                1645                1650

Arg Met Ser Phe Thr Cys Ser Phe Asn Lys Ser Cys Asn Val Val
1655                1660                1665

Val Ala Gln Asp Cys Thr Glu His Pro Lys Phe Ile Ile Thr Thr
1670                1675                1680

Arg Lys Val Asp His Gln Ser Leu Ser Arg Glu Val His Ile Asn
1685                1690                1695

Thr Ser Ser Ala Asn Ile Thr Ile Cys Pro Ala Ala Asp Ser Ser
1700                1705                1710

Leu Leu Val Thr Cys Asn Lys Glu Ser Val Leu Ser Asp Ser Gly
1715                1720                1725

Val Ser Glu Tyr Glu Lys Asp Asn Ile Lys Ile Tyr Lys Asn Gly
1730                1735                1740

Lys Thr Val Ile Val Glu Ala Pro Ile His Gly Leu Lys Asn Val
1745                1750                1755

Asn Phe Asp Gly Glu Ile Leu Lys Val Thr Val Ala Ser Trp Met
1760                1765                1770

Arg Gly Lys Thr Cys Gly Val Cys Gly Asn Asn Asp Arg Glu Lys
1775                1780                1785

His Asn Glu Leu Leu Met Pro Asn His Lys Leu Ala His Ser Cys
1790                1795                1800

Ser Ala Phe Val His Ser Trp Val Leu Leu Glu Glu Thr Cys Ser
1805                1810                1815

Gly Gly Cys Lys Leu Gln Arg Arg Tyr Val Lys Leu Asn Arg Asn
1820                1825                1830

Pro Thr Ile Asp Gly Glu Glu Ser Thr Cys Tyr Ser Val Asp Pro
1835                1840                1845
```

-continued

Val Leu Lys Cys Met Lys Asp Cys Thr Pro Ile Glu Lys Thr Ser
1850              1855                1860

Val Lys Val Gly Phe His Cys Phe Pro Lys Ala Thr Ala Val Ser
1865              1870                1875

Leu Leu Glu Trp Gln Arg Ser Ser Asp Lys Lys Ser Ala Ser Glu
1880              1885                1890

Asp Val Val Glu Ser Val Asp Ala Asp Ile Asp Cys Thr Cys Thr
1895              1900                1905

Gly Asp Cys Ser
1910

<210> SEQ ID NO 22
<211> LENGTH: 1850
<212> TYPE: PRT
<213> ORGANISM: Gallus gallus

<400> SEQUENCE: 22

Met Arg Gly Ile Ile Leu Ala Leu Val Leu Thr Leu Gly Ser Gln
1               5                   10                  15

Lys Phe Asp Ile Asp Pro Gly Phe Asn Ser Arg Arg Ser Tyr Leu Tyr
                20                  25                  30

Asn Tyr Glu Gly Ser Met Leu Asn Gly Leu Gln Asp Arg Ser Leu Gly
            35                  40                  45

Lys Ala Gly Val Arg Leu Ser Ser Lys Leu Glu Ile Ser Gly Leu Pro
50                  55                  60

Glu Asn Ala Tyr Leu Leu Lys Val Arg Ser Pro Gln Val Glu Tyr
65                  70                  75                  80

Asn Gly Val Trp Pro Arg Asp Pro Phe Thr Arg Ser Ser Lys Ile Thr
                85                  90                  95

Gln Val Ile Ser Ser Cys Phe Thr Arg Leu Phe Lys Phe Glu Tyr Ser
                100                 105                 110

Ser Gly Arg Ile Gly Asn Ile Tyr Ala Pro Glu Asp Cys Pro Asp Leu
            115                 120                 125

Cys Val Asn Ile Val Arg Gly Ile Leu Asn Met Phe Gln Met Thr Ile
130                 135                 140

Lys Lys Ser Gln Asn Val Tyr Glu Leu Gln Glu Ala Gly Ile Gly Gly
145                 150                 155                 160

Ile Cys His Ala Arg Tyr Val Ile Gln Glu Asp Arg Lys Asn Ser Arg
                165                 170                 175

Ile Tyr Val Thr Arg Thr Val Asp Leu Asn Asn Cys Gln Glu Lys Val
            180                 185                 190

Gln Lys Ser Ile Gly Met Ala Tyr Ile Tyr Pro Cys Pro Val Asp Val
        195                 200                 205

Met Lys Glu Arg Leu Thr Lys Gly Thr Thr Ala Phe Ser Tyr Lys Leu
210                 215                 220

Lys Gln Ser Asp Ser Gly Thr Leu Ile Thr Asp Val Ser Ser Arg Gln
225                 230                 235                 240

Val Tyr Gln Ile Ser Pro Phe Asn Glu Pro Thr Gly Val Ala Val Met
                245                 250                 255

Glu Ala Arg Gln Gln Leu Thr Leu Val Glu Val Arg Ser Glu Arg Gly
            260                 265                 270

Ser Ala Pro Asp Val Pro Met Gln Asn Tyr Gly Ser Leu Arg Tyr Arg
        275                 280                 285

Phe Pro Ala Val Leu Pro Gln Met Pro Leu Gln Leu Ile Lys Thr Lys
290                 295                 300

```
Asn Pro Glu Gln Arg Ile Val Glu Thr Leu Gln His Ile Val Leu Asn
305                 310                 315                 320

Asn Gln Gln Asp Phe His Asp Val Ser Tyr Arg Phe Leu Glu Val
            325                 330                 335

Val Gln Leu Cys Arg Ile Ala Asn Ala Asp Asn Leu Glu Ser Ile Trp
                340                 345                 350

Arg Gln Val Ser Asp Lys Pro Arg Tyr Arg Arg Trp Leu Leu Ser Ala
            355                 360                 365

Val Ser Ala Ser Gly Thr Thr Glu Thr Leu Lys Phe Leu Lys Asn Arg
370                 375                 380

Ile Arg Asn Asp Asp Leu Asn Tyr Ile Gln Thr Leu Leu Thr Val Ser
385                 390                 395                 400

Leu Thr Leu His Leu Leu Gln Ala Asp Glu His Thr Leu Pro Ile Ala
                405                 410                 415

Ala Asp Leu Met Thr Ser Ser Arg Ile Gln Lys Asn Pro Val Leu Gln
                420                 425                 430

Gln Val Ala Cys Leu Gly Tyr Ser Ser Val Val Asn Arg Tyr Cys Ser
            435                 440                 445

Gln Thr Ser Ala Cys Pro Lys Glu Ala Leu Gln Pro Ile His Asp Leu
450                 455                 460

Ala Asp Glu Ala Ile Ser Arg Gly Arg Glu Asp Lys Met Lys Leu Ala
465                 470                 475                 480

Leu Lys Cys Ile Gly Asn Met Gly Glu Pro Ala Ser Leu Lys Arg Ile
                485                 490                 495

Leu Lys Phe Leu Pro Ile Ser Ser Ser Ala Ala Asp Ile Pro Val
            500                 505                 510

His Ile Gln Ile Asp Ala Ile Thr Ala Leu Lys Lys Ile Ala Trp Lys
515                 520                 525

Asp Pro Lys Thr Val Gln Gly Tyr Leu Ile Gln Ile Leu Ala Asp Gln
            530                 535                 540

Ser Leu Pro Pro Glu Val Arg Met Met Ala Cys Ala Val Ile Phe Glu
545                 550                 555                 560

Thr Arg Pro Ala Leu Ala Leu Ile Thr Thr Ile Ala Asn Val Ala Met
                565                 570                 575

Lys Glu Ser Asn Met Gln Val Ala Ser Phe Val Tyr Ser His Met Lys
            580                 585                 590

Ser Leu Ser Lys Ser Arg Leu Pro Phe Met Tyr Asn Ile Ser Ser Ala
            595                 600                 605

Cys Asn Ile Ala Leu Lys Leu Leu Ser Pro Lys Leu Asp Ser Met Ser
            610                 615                 620

Tyr Arg Tyr Ser Lys Val Ile Arg Ala Asp Thr Tyr Phe Asp Asn Tyr
625                 630                 635                 640

Arg Val Gly Ala Thr Gly Glu Ile Phe Val Val Asn Ser Pro Arg Thr
                645                 650                 655

Met Phe Pro Ser Ala Ile Ile Ser Lys Leu Met Ala Asn Ser Ala Gly
                660                 665                 670

Ser Val Ala Asp Leu Val Glu Val Gly Ile Arg Val Glu Gly Leu Ala
            675                 680                 685

Asp Val Ile Met Lys Arg Asn Ile Pro Phe Ala Glu Tyr Pro Thr Tyr
            690                 695                 700

Lys Gln Ile Lys Glu Leu Gly Lys Ala Leu Gln Gly Trp Lys Glu Leu
705                 710                 715                 720
```

```
Pro Thr Glu Thr Pro Leu Val Ser Ala Tyr Leu Lys Ile Leu Gly Gln
            725                 730                 735

Glu Val Ala Phe Ile Asn Ile Asn Lys Glu Leu Leu Gln Gln Val Met
            740                 745                 750

Lys Thr Val Val Glu Pro Ala Asp Arg Asn Ala Ala Ile Lys Arg Ile
            755                 760                 765

Ala Asn Gln Ile Arg Asn Ser Ile Ala Gly Gln Trp Thr Gln Pro Val
            770                 775                 780

Trp Met Gly Glu Leu Arg Tyr Val Val Pro Ser Cys Leu Gly Leu Pro
785                 790                 795                 800

Leu Glu Tyr Gly Ser Tyr Thr Thr Ala Leu Ala Arg Ala Ala Val Ser
            805                 810                 815

Val Glu Gly Lys Met Thr Pro Pro Leu Thr Gly Asp Phe Arg Leu Ser
            820                 825                 830

Gln Leu Leu Glu Ser Thr Met Gln Ile Arg Ser Asp Leu Lys Pro Ser
            835                 840                 845

Leu Tyr Val His Thr Val Ala Thr Met Gly Val Asn Thr Glu Tyr Phe
            850                 855                 860

Gln His Ala Val Glu Ile Gln Gly Glu Val Gln Thr Arg Met Pro Met
865                 870                 875                 880

Lys Phe Asp Ala Lys Ile Asp Val Lys Leu Lys Asn Leu Lys Ile Glu
            885                 890                 895

Thr Asn Pro Cys Arg Glu Thr Glu Ile Val Val Gly Arg His Lys
            900                 905                 910

Ala Phe Ala Val Ser Arg Asn Ile Gly Glu Leu Gly Val Glu Lys Arg
            915                 920                 925

Thr Ser Ile Leu Pro Glu Asp Ala Pro Leu Asp Val Thr Glu Pro
            930                 935                 940

Phe Gln Thr Ser Glu Arg Ala Ser Arg Glu His Phe Ala Met Gln Gly
945                 950                 955                 960

Pro Asp Ser Met Pro Arg Lys Gln Ser His Ser Arg Glu Asp Leu
                965                 970                 975

Arg Arg Ser Thr Gly Lys Arg Ala His Lys Arg Asp Ile Cys Leu Lys
            980                 985                 990

Met His His Ile Gly Cys Gln Leu  Cys Phe Ser Arg Arg  Ser Arg Asp
            995                 1000                1005

Ala Ser  Phe Ile Gln Asn Thr  Tyr Leu His Lys Leu  Ile Gly Glu
    1010                1015                1020

His Glu  Ala Lys Ile Val Leu  Met Pro Val His Thr  Asp Ala Asp
    1025                1030                1035

Ile Asp  Lys Ile Gln Leu Glu  Ile Gln Ala Gly Ser  Arg Ala Ala
    1040                1045                1050

Ala Arg  Ile Ile Thr Glu Val  Asn Pro Glu Ser Glu  Glu Glu Asp
    1055                1060                1065

Glu Ser  Ser Pro Tyr Glu Asp  Ile Gln Ala Lys Leu  Lys Arg Ile
    1070                1075                1080

Leu Gly  Ile Asp Ser Met Phe  Lys Val Ala Asn Lys  Thr Arg His
    1085                1090                1095

Pro Lys  Asn Arg Pro Ser Lys  Lys Gly Asn Thr Val  Leu Ala Glu
    1100                1105                1110

Phe Gly  Thr Glu Pro Asp Ala  Lys Thr Ser Ser Ser  Ser Ser Ser
    1115                1120                1125

Ala Ser  Ser Thr Ala Thr Ser  Ser Ser Ser Ser Ser  Ala Ser Ser
```

-continued

```
                1130              1135              1140
Pro Asn Arg Lys Lys Pro Met Asp Glu Glu Asn Asp Gln Val
        1145              1150              1155
Lys Gln Ala Arg Asn Lys Asp Ala Ser Ser Ser Arg Ser Ser
        1160              1165              1170
Lys Ser Ser Asn Ser Ser Lys Arg Ser Ser Lys Ser Ser Asn
        1175              1180              1185
Ser Ser Lys Arg Ser Ser Ser Ser Ser Ser Ser Ser Ser Ser
        1190              1195              1200
Ser Arg Ser Ser Ser Ser Ser Ser Ser Ser Asn Ser Lys
        1205              1210              1215
Ser Ser Ser Ser Ser Ser Lys Ser Ser Ser Ser Ser Arg Ser
        1220              1225              1230
Arg Ser Ser Ser Lys Ser Ser Ser Ser Ser Ser Ser Ser Ser
        1235              1240              1245
Ser Ser Ser Ser Lys Ser Ser Ser Ser Arg Ser Ser Ser Ser
        1250              1255              1260
Ser Lys Ser Ser Ser His His Ser His Ser His His Ser Gly His
        1265              1270              1275
Leu Asn Gly Ser Ser Ser Ser Ser Ser Ser Arg Ser Val Ser
        1280              1285              1290
His His Ser His Glu His His Ser Gly His Leu Glu Asp Asp Ser
        1295              1300              1305
Ser Ser Ser Ser Ser Ser Ser Val Leu Ser Lys Ile Trp Gly Arg
        1310              1315              1320
His Glu Ile Tyr Gln Tyr Arg Phe Arg Ser Ala His Arg Gln Glu
        1325              1330              1335
Phe Pro Lys Arg Lys Leu Pro Gly Asp Arg Ala Thr Ser Arg Tyr
        1340              1345              1350
Ser Ser Thr Arg Ser Ser His Asp Thr Ser Arg Ala Ala Ser Trp
        1355              1360              1365
Pro Lys Phe Leu Gly Asp Ile Lys Thr Pro Val Leu Ala Ala Phe
        1370              1375              1380
Leu His Gly Ile Ser Asn Asn Lys Lys Thr Gly Gly Leu Gln Leu
        1385              1390              1395
Val Val Tyr Ala Asp Thr Asp Ser Val Arg Pro Arg Val Gln Val
        1400              1405              1410
Phe Val Thr Asn Leu Thr Asp Ser Ser Lys Trp Lys Leu Cys Ala
        1415              1420              1425
Asp Ala Ser Val Arg Asn Ala His Lys Ala Val Ala Tyr Val Lys
        1430              1435              1440
Trp Gly Trp Asp Cys Arg Asp Tyr Lys Val Ser Thr Glu Leu Val
        1445              1450              1455
Thr Gly Arg Phe Ala Gly His Pro Ala Ala Gln Val Lys Leu Glu
        1460              1465              1470
Trp Pro Lys Val Pro Ser Asn Val Arg Ser Val Val Glu Trp Phe
        1475              1480              1485
Tyr Glu Phe Val Pro Gly Ala Ala Phe Met Leu Gly Phe Ser Glu
        1490              1495              1500
Arg Met Asp Lys Asn Pro Ser Arg Gln Ala Arg Met Val Val Ala
        1505              1510              1515
Leu Thr Ser Pro Arg Thr Cys Asp Val Val Val Lys Leu Pro Asp
        1520              1525              1530
```

```
Ile Ile Leu Tyr Gln Lys Ala Val Arg Leu Pro Leu Ser Leu Pro
    1535                1540                1545

Val Gly Pro Arg Ile Pro Ala Ser Glu Leu Gln Pro Pro Ile Trp
    1550                1555                1560

Asn Val Phe Ala Glu Ala Pro Ser Ala Val Leu Glu Asn Leu Lys
    1565                1570                1575

Ala Arg Cys Ser Val Ser Tyr Asn Lys Ile Lys Thr Phe Asn Glu
    1580                1585                1590

Val Lys Phe Asn Tyr Ser Met Pro Ala Asn Cys Tyr His Ile Leu
    1595                1600                1605

Val Gln Asp Cys Ser Ser Glu Leu Lys Phe Leu Val Met Met Lys
    1610                1615                1620

Ser Ala Gly Glu Ala Thr Asn Leu Lys Ala Ile Asn Ile Lys Ile
    1625                1630                1635

Gly Ser His Glu Ile Asp Met His Pro Val Asn Gly Gln Val Lys
    1640                1645                1650

Leu Leu Val Asp Gly Ala Glu Ser Pro Thr Ala Asn Ile Ser Leu
    1655                1660                1665

Ile Ser Ala Gly Ala Ser Leu Trp Ile His Asn Glu Asn Gln Gly
    1670                1675                1680

Phe Ala Leu Ala Ala Pro Gly His Gly Ile Asp Lys Leu Tyr Phe
    1685                1690                1695

Asp Gly Lys Thr Ile Thr Ile Gln Val Pro Leu Trp Met Ala Gly
    1700                1705                1710

Lys Thr Cys Gly Ile Cys Gly Lys Tyr Asp Ala Glu Cys Glu Gln
    1715                1720                1725

Glu Tyr Arg Met Pro Asn Gly Tyr Leu Ala Lys Asn Ala Val Ser
    1730                1735                1740

Phe Gly His Ser Trp Ile Leu Glu Glu Ala Pro Cys Arg Gly Ala
    1745                1750                1755

Cys Lys Leu His Arg Ser Phe Val Lys Leu Glu Lys Thr Val Gln
    1760                1765                1770

Leu Ala Gly Val Asp Ser Lys Cys Tyr Ser Thr Glu Pro Val Leu
    1775                1780                1785

Arg Cys Ala Lys Gly Cys Ser Ala Thr Lys Thr Thr Pro Val Thr
    1790                1795                1800

Val Gly Phe His Cys Leu Pro Ala Asp Ser Ala Asn Ser Leu Thr
    1805                1810                1815

Asp Lys Gln Met Lys Tyr Asp Gln Lys Ser Glu Asp Met Gln Asp
    1820                1825                1830

Thr Val Asp Ala His Thr Thr Cys Ser Cys Glu Asn Glu Glu Cys
    1835                1840                1845

Ser Thr
    1850

<210> SEQ ID NO 23
<211> LENGTH: 386
<212> TYPE: PRT
<213> ORGANISM: Gallus gallus

<400> SEQUENCE: 23

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
```

```
            20                  25                  30
Ile Ala Ile Met Ser Ala Leu Ala Met Val Tyr Leu Gly Ala Lys Asp
            35                  40                  45

Ser Thr Arg Thr Gln Ile Asn Lys Val Val Arg Phe Asp Lys Leu Pro
 50                  55                  60

Gly Phe Gly Asp Ser Ile Glu Ala Gln Cys Gly Thr Ser Val Asn Val
 65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
                100                 105                 110

Pro Ile Leu Pro Glu Tyr Leu Gln Cys Val Lys Glu Leu Tyr Arg Gly
                115                 120                 125

Gly Leu Glu Pro Ile Asn Phe Gln Thr Ala Ala Asp Gln Ala Arg Glu
                130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
                180                 185                 190

Asp Thr Gln Ala Met Pro Phe Arg Val Thr Glu Gln Glu Ser Lys Pro
                195                 200                 205

Val Gln Met Met Tyr Gln Ile Gly Leu Phe Arg Val Ala Ser Met Ala
                210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
                260                 265                 270

Val Met Glu Glu Arg Lys Ile Lys Val Tyr Leu Pro Arg Met Lys Met
                275                 280                 285

Glu Glu Lys Tyr Asn Leu Thr Ser Val Leu Met Ala Met Gly Ile Thr
                290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
                340                 345                 350

Ala Ser Val Ser Glu Glu Phe Arg Ala Asp His Pro Phe Leu Phe Cys
                355                 360                 365

Ile Lys His Ile Ala Thr Asn Ala Val Leu Phe Phe Gly Arg Cys Val
                370                 375                 380

Ser Pro
385

<210> SEQ ID NO 24
<211> LENGTH: 738
<212> TYPE: PRT
<213> ORGANISM: Gallus gallus

<400> SEQUENCE: 24
```

```
Met Lys Ser Ser Glu Asn Val Leu Tyr Leu Leu Val His Ala Ala
1               5                   10                  15
Leu Ser Leu Glu Arg Val Arg Trp Cys Thr Met Ser Asn Gln Glu Leu
            20                  25                  30
Ser Lys Cys Lys Asp Met Ser Asn Ala Phe Thr Gly Ala Gly Ile Leu
        35                  40                  45
Pro Pro Leu Glu Cys Met Glu Gly Ser Ala Ala Asn Cys Thr Gln
50                  55                  60
Met Ile Lys Asp Tyr Leu Ala Asp Thr Val Thr Leu Asp Gly Arg Trp
65                  70                  75                  80
Ile Tyr Gln Ala Gly Lys Glu Tyr Gly Leu Lys Pro Val Val Gly Glu
                85                  90                  95
Val Tyr Asp Gln Glu Ile Gly Thr Ser Tyr Tyr Ala Val Ala Val Val
            100                 105                 110
Arg Lys Gly Ser Asn Ile Thr Ile Asn Ser Leu Lys Gly Val Arg Ser
        115                 120                 125
Cys His Thr Gly Ile Asn Arg Thr Ala Gly Trp Asn Val Pro Val Gly
    130                 135                 140
Tyr Leu Ile Asp Ser Gly Arg Leu Pro Ala Met Gly Cys Asp Leu Pro
145                 150                 155                 160
Lys Ala Val Ser Asp Tyr Phe Ser Ala Ser Cys Val Pro Gly Thr Asn
                165                 170                 175
Ser Ala Ser Tyr Pro Thr Ser Leu Cys Gln Leu Cys Lys Gly Asp Ser
            180                 185                 190
Ser Gly Gln Asn Lys Cys Gln Gly Asn Ser Gln Glu Gln Tyr Tyr Asp
        195                 200                 205
Tyr Ser Gly Ala Phe Arg Cys Leu Ala Glu Gly Ala Gly Glu Val Ala
    210                 215                 220
Phe Val Lys His Ser Thr Val Pro Glu Asn Thr Asp Gly Arg Thr Leu
225                 230                 235                 240
Ser Thr Trp Ala Gln Gln Phe Arg Ser Lys Asp Phe Gln Leu Leu Cys
                245                 250                 255
Arg Asn Gly Ser Thr Ala Asp Val Thr Glu Trp Arg Thr Cys His Leu
            260                 265                 270
Ala Arg Val Pro Ala Arg Ala Val Val Arg Pro Asp Thr Asp Gly
        275                 280                 285
Thr Ala Val Phe Gln Leu Leu Asn Gln Gly Gln Gln Arg Phe Asn Asp
290                 295                 300
Val Gly Ala Gln Phe Gln Met Phe Asp Ser Thr Ala Tyr Gly Ala Gln
305                 310                 315                 320
Asn Leu Met Phe Arg Asp Ser Thr Thr Lys Leu Val Ala Val Thr Ser
                325                 330                 335
Gln Asn Tyr Gln Ala Trp Leu Gly Asp Glu Tyr Leu His Gly Met Gln
            340                 345                 350
Ala Leu Ser Cys Asp Pro Asn Thr Leu Pro Glu Ser Leu Asn Trp Cys
        355                 360                 365
Val Val Ser Thr Glu Glu Ile Trp Lys Cys Gly Glu Met Gly Thr Ala
    370                 375                 380
Phe Arg Ser Lys Asn Leu Lys Pro Glu Ile Gln Cys Ile Ser Ala Lys
385                 390                 395                 400
Thr Lys Glu Glu Cys Met Glu Met Ile Gln Lys Glu Ile Asp Val
                405                 410                 415
Val Ala Leu Gly Gly Val Asp Ile Tyr Ile Ala Gly Lys Thr Tyr Gly
```

```
                420             425             430
Leu Val Pro Ala Ala Gly Glu Ser Phe Ser Ala Glu Asp Asn Asn
            435             440             445
Ala Tyr Tyr Ala Val Ala Leu Val Lys Arg Asn Pro Ser Asn Ala Phe
        450             455             460
Thr Ile Asn Asp Leu Lys Gly Lys Ser Cys His Thr Gly Leu Gly
465             470             475             480
Arg Thr Ala Gly Trp Asn Ile Pro Ile Gly Met Leu Val Lys Lys Gly
                485             490             495
Phe Ile Asn Pro Arg Asp Cys Asn Ile Pro Gln Ala Val Ser Glu Phe
            500             505             510
Phe Ser Ala Ser Cys Val Pro Ser Ala Glu Gln Gly Asn Tyr Pro Ser
        515             520             525
Thr Leu Cys Gln Leu Cys Ile Gly Asp Asn Asn Gly Asn Asn Lys Cys
        530             535             540
Ser Ala Ser Ser Gln Glu Arg Tyr Tyr Ser Tyr Asn Gly Ala Phe Arg
545             550             555             560
Cys Leu Ala Glu Asp Ala Gly Asp Val Ala Phe Val Lys His Ser Thr
                565             570             575
Val Phe Glu Asn Thr Asp Gly Lys Asn Thr Glu Ser Trp Ala Arg Asp
            580             585             590
Leu Lys Ser Ser Gly Phe Gln Leu Leu Cys Arg Asn Gly Ala Arg Ala
        595             600             605
Glu Val Thr Gln Phe Ala Gln Cys His Leu Ala Arg Val Pro Ala Gln
        610             615             620
Ala Ile Met Val His Pro Asp Thr Asn Ile Phe Ala Leu Tyr Gly Leu
625             630             635             640
Leu Asp Lys Ala Gln Glu Tyr Phe Gly Asn Asn Ser Asn Arg Asn Gly
                645             650             655
Phe Lys Met Phe Asp Ser Ser Ala Phe Gln Gly Lys Asp Leu Ile Phe
            660             665             670
Lys Asp Ser Ala Val Lys Ile Val Pro Val Glu Glu Arg Arg Thr Tyr
        675             680             685
Ala Glu Trp Leu Gly Ser Glu Tyr Val Glu Ser Leu Glu Gly Met Gln
        690             695             700
Thr Pro Gln Cys Ser Gly Ala Gly Asn Lys Leu Ile Gln Gln His Leu
705             710             715             720
Leu Val Ile Thr Phe Val Pro Phe Ile Ile Leu Gly Gln Leu Gln Gly
                725             730             735
Leu Gly

<210> SEQ ID NO 25
<211> LENGTH: 210
<212> TYPE: PRT
<213> ORGANISM: Gallus gallus

<400> SEQUENCE: 25

Met Ala Met Ala Gly Val Phe Val Leu Phe Ser Phe Val Leu Cys Gly
1               5                   10                  15
Phe Leu Pro Asp Ala Ala Phe Gly Ala Glu Val Asp Cys Ser Arg Phe
            20                  25                  30
Pro Asn Ala Thr Asp Lys Glu Gly Lys Asp Val Leu Val Cys Asn Lys
        35                  40                  45
Asp Leu Arg Pro Ile Cys Gly Thr Asp Gly Val Thr Tyr Thr Asn Asp
```

```
            50                  55                  60
Cys Leu Leu Cys Ala Tyr Ser Ile Glu Phe Gly Thr Asn Ile Ser Lys
 65                  70                  75                  80

Glu His Asp Gly Glu Cys Lys Glu Thr Val Pro Met Asn Cys Ser Ser
                     85                  90                  95

Tyr Ala Asn Thr Thr Ser Glu Asp Gly Lys Val Met Val Leu Cys Asn
                100                 105                 110

Arg Ala Phe Asn Pro Val Cys Gly Thr Asp Gly Val Thr Tyr Asp Asn
                115                 120                 125

Glu Cys Leu Leu Cys Ala His Lys Val Glu Gln Gly Ala Ser Val Asp
130                 135                 140

Lys Arg His Asp Gly Gly Cys Arg Lys Glu Leu Ala Ala Val Ser Val
145                 150                 155                 160

Asp Cys Ser Glu Tyr Pro Lys Pro Asp Cys Thr Ala Glu Asp Arg Pro
                165                 170                 175

Leu Cys Gly Ser Asp Asn Lys Thr Tyr Gly Asn Lys Cys Asn Phe Cys
                180                 185                 190

Asn Ala Val Val Glu Ser Asn Gly Thr Leu Thr Leu Ser His Phe Gly
                195                 200                 205

Lys Cys
    210

<210> SEQ ID NO 26
<211> LENGTH: 2108
<212> TYPE: PRT
<213> ORGANISM: Gallus gallus

<400> SEQUENCE: 26

Met Glu Ile Lys Lys Glu Arg Ser Phe Trp Ile Phe Cys Leu Ile Trp
 1               5                  10                  15

Ser Phe Cys Lys Gly Lys Glu Pro Val Gln Ile Val Gln Val Ser Thr
                 20                  25                  30

Val Gly Arg Ser Glu Cys Thr Thr Trp Gly Asn Phe His Phe His Thr
                 35                  40                  45

Phe Asp His Val Lys Phe Thr Phe Pro Gly Thr Cys Thr Tyr Val Phe
     50                  55                  60

Ala Ser His Cys Asn Asp Ser Tyr Gln Asp Phe Asn Ile Lys Ile Arg
 65                  70                  75                  80

Arg Ser Asp Lys Asn Ser His Leu Ile Tyr Phe Thr Val Thr Thr Asp
                 85                  90                  95

Gly Val Ile Leu Glu Val Lys Glu Thr Gly Ile Thr Val Asn Gly Asn
                100                 105                 110

Gln Ile Pro Leu Pro Phe Ser Leu Lys Ser Ile Leu Ile Glu Asp Thr
                115                 120                 125

Cys Ala Tyr Phe Gln Val Thr Ser Lys Leu Gly Leu Thr Leu Lys Trp
130                 135                 140

Asn Trp Ala Asp Thr Leu Leu Leu Asp Leu Glu Thr Tyr Lys Glu
145                 150                 155                 160

Lys Ile Cys Gly Leu Cys Gly Asn Tyr Asp Gly Asn Lys Lys Asn Asp
                165                 170                 175

Leu Ile Leu Asp Gly Tyr Lys Met His Pro Arg Gln Phe Gly Asn Phe
                180                 185                 190

His Lys Val Glu Asp Pro Ser Glu Lys Cys Pro Asp Val Arg Pro Asp
                195                 200                 205
```

```
Asp His Thr Gly Arg His Pro Thr Glu Asp Asp Asn Arg Cys Ser Lys
    210                 215                 220
Tyr Lys Lys Met Cys Lys Lys Leu Leu Ser Arg Phe Gly Asn Cys Pro
225                 230                 235                 240
Lys Val Val Ala Phe Asp Asp Tyr Val Ala Thr Cys Thr Glu Asp Met
                245                 250                 255
Cys Asn Cys Val Val Asn Ser Ser Gln Ser Asp Leu Val Ser Ser Cys
                260                 265                 270
Ile Cys Ser Thr Leu Asn Gln Tyr Ser Arg Asp Cys Val Leu Ser Lys
        275                 280                 285
Gly Asp Pro Gly Glu Trp Arg Thr Lys Glu Leu Cys Tyr Gln Glu Cys
290                 295                 300
Pro Ser Asn Met Glu Tyr Met Glu Cys Gly Asn Ser Cys Ala Asp Thr
305                 310                 315                 320
Cys Ala Asp Pro Glu Arg Ser Lys Ile Cys Lys Ala Pro Cys Thr Asp
                325                 330                 335
Gly Cys Phe Cys Pro Pro Gly Thr Ile Leu Asp Asp Leu Gly Gly Lys
                340                 345                 350
Lys Cys Val Pro Arg Asp Ser Cys Pro Cys Met Phe Gln Gly Lys Val
        355                 360                 365
Tyr Ser Ser Gly Gly Thr Tyr Ser Thr Pro Cys Gln Asn Cys Thr Cys
370                 375                 380
Lys Gly Gly His Trp Ser Cys Ile Ser Leu Pro Cys Ser Gly Ser Cys
385                 390                 395                 400
Ser Ile Asp Gly Gly Phe His Ile Lys Thr Phe Asp Asn Lys Lys Phe
                405                 410                 415
Asn Phe His Gly Asn Cys His Tyr Val Leu Ala Lys Asn Thr Asp Asp
                420                 425                 430
Thr Phe Val Val Ile Gly Glu Ile Ile Gln Cys Gly Thr Ser Lys Thr
        435                 440                 445
Met Thr Cys Leu Lys Asn Val Leu Val Thr Leu Gly Arg Thr Thr Ile
450                 455                 460
Lys Ile Cys Ser Cys Gly Ser Ile Tyr Met Asn Asn Phe Ile Val Lys
465                 470                 475                 480
Leu Pro Val Ser Lys Asp Gly Ile Thr Ile Phe Arg Pro Ser Thr Phe
                485                 490                 495
Phe Ile Lys Ile Leu Ser Ser Ala Gly Val Gln Ile Arg Val Gln Met
                500                 505                 510
Lys Pro Val Met Gln Leu Ser Ile Thr Val Asp His Ser Tyr Gln Asn
        515                 520                 525
Arg Thr Ser Gly Leu Cys Gly Asn Phe Asn Asn Ile Gln Thr Asp Asp
530                 535                 540
Phe Arg Thr Ala Thr Gly Ala Val Glu Asp Ser Ala Ala Ala Phe Gly
545                 550                 555                 560
Asn Ser Trp Lys Thr Arg Ala Ser Cys Phe Asp Val Glu Asp Ser Phe
                565                 570                 575
Glu Asp Pro Cys Ser Asn Ser Val Asp Lys Glu Lys Phe Ala Gln His
                580                 585                 590
Trp Cys Ala Leu Leu Ser Asn Thr Ser Ser Thr Phe Ala Ala Cys His
        595                 600                 605
Ser Val Val Asp Pro Ser Val Tyr Ile Lys Arg Cys Met Tyr Asp Thr
610                 615                 620
Cys Asn Ala Glu Lys Ser Glu Val Ala Leu Cys Ser Val Leu Ser Thr
```

-continued

```
            625                 630                 635                 640
Tyr Ser Arg Asp Cys Ala Ala Gly Met Thr Leu Lys Gly Trp Arg
                645                 650                 655

Gln Gly Ile Cys Asp Pro Ser Glu Glu Cys Pro Glu Thr Met Val Tyr
                660                 665                 670

Asn Tyr Ser Val Lys Tyr Cys Asn Gln Ser Cys Arg Ser Leu Asp Glu
                675                 680                 685

Pro Asp Pro Leu Cys Lys Val Gln Ile Ala Pro Met Glu Gly Cys Gly
            690                 695                 700

Cys Pro Glu Gly Thr Tyr Leu Asn Asp Glu Glu Cys Val Thr Pro
705                 710                 715                 720

Asp Asp Cys Pro Cys Tyr Tyr Lys Gly Lys Ile Val Gln Pro Gly Asn
                725                 730                 735

Ser Phe Gln Glu Asp Lys Leu Leu Cys Lys Cys Ile Gln Gly Arg Leu
                740                 745                 750

Asp Cys Ile Gly Glu Thr Val Leu Val Lys Asp Cys Pro Ala Pro Met
                755                 760                 765

Tyr Tyr Phe Asn Cys Ser Ser Ala Gly Pro Gly Ala Ile Gly Ser Glu
                770                 775                 780

Cys Gln Lys Ser Cys Lys Thr Gln Asp Met His Cys Tyr Val Thr Glu
785                 790                 795                 800

Cys Val Ser Gly Cys Met Cys Pro Asp Gly Leu Val Leu Asp Gly Ser
                805                 810                 815

Gly Gly Cys Ile Pro Lys Asp Gln Cys Pro Cys Val His Gly Gly His
                820                 825                 830

Phe Tyr Lys Pro Gly Glu Thr Ile Arg Val Asp Cys Asn Thr Cys Thr
                835                 840                 845

Cys Asn Lys Arg Gln Trp Asn Cys Thr Asp Asn Pro Cys Lys Gly Thr
                850                 855                 860

Cys Thr Val Tyr Gly Asn Gly His Tyr Met Ser Phe Asp Gly Glu Lys
865                 870                 875                 880

Phe Asp Phe Leu Gly Asp Cys Asp Tyr Ile Leu Ala Gln Asp Phe Cys
                885                 890                 895

Pro Asn Asn Met Asp Ala Gly Thr Phe Arg Ile Val Ile Gln Asn Asn
                900                 905                 910

Ala Cys Gly Lys Ser Leu Ser Ile Cys Ser Leu Lys Ile Thr Leu Ile
                915                 920                 925

Phe Glu Ser Ser Glu Ile Arg Leu Leu Glu Gly Arg Ile Gln Glu Ile
                930                 935                 940

Ala Thr Asp Pro Gly Ala Glu Lys Asn Tyr Lys Val Asp Leu Arg Gly
945                 950                 955                 960

Gly Tyr Ile Val Ile Glu Thr Thr Gln Gly Met Ser Phe Met Trp Asp
                965                 970                 975

Gln Lys Thr Thr Val Val Val His Val Thr Pro Ser Phe Gln Gly Lys
                980                 985                 990

Val Cys Gly Leu Cys Gly Asp Phe Asp Gly Arg Ser Arg Asn Asp Phe
                995                 1000                1005

Thr Thr Arg Gly Gln Ser Val Glu Met Ser Ile Gln Glu Phe Gly
            1010                1015                1020

Asn Ser Trp Lys Ile Thr Ser Thr Cys Ser Asn Ile Asn Met Thr
            1025                1030                1035

Asp Leu Cys Ala Asp Gln Pro Phe Lys Ser Ala Leu Gly Gln Lys
            1040                1045                1050
```

```
His Cys Ser Ile Ile Lys Ser Ser Val Phe Glu Ala Cys His Ser
1055                1060                1065

Lys Val Asn Pro Ile Pro Tyr Tyr Glu Ser Cys Val Ser Asp Phe
1070                1075                1080

Cys Gly Cys Asp Ser Val Gly Asp Cys Glu Cys Phe Cys Thr Ser
1085                1090                1095

Val Ala Ala Tyr Ala Arg Ser Cys Ser Thr Ala Gly Val Cys Ile
1100                1105                1110

Asn Trp Arg Thr Pro Ala Ile Cys Pro Val Phe Cys Asp Tyr Tyr
1115                1120                1125

Asn Pro Pro Asp Lys His Glu Trp Phe Tyr Lys Pro Cys Gly Ala
1130                1135                1140

Pro Cys Leu Lys Thr Cys Arg Asn Pro Gln Gly Lys Cys Gly Asn
1145                1150                1155

Ile Leu Tyr Ser Leu Glu Gly Cys Tyr Pro Glu Cys Ser Pro Asp
1160                1165                1170

Lys Pro Tyr Phe Asp Glu Glu Arg Arg Glu Cys Val Ser Leu Pro
1175                1180                1185

Asp Cys Thr Ser Cys Asn Pro Glu Glu Lys Leu Cys Thr Glu Asp
1190                1195                1200

Ser Lys Asp Cys Leu Cys Cys Tyr Asn Gly Lys Thr Tyr Pro Leu
1205                1210                1215

Asn Glu Thr Ile Tyr Ser Gln Thr Glu Gly Thr Lys Cys Gly Asn
1220                1225                1230

Ala Phe Cys Gly Pro Asn Gly Met Ile Ile Glu Thr Phe Ile Pro
1235                1240                1245

Cys Ser Thr Leu Ser Val Pro Ala Gln Glu Gln Leu Met Gln Pro
1250                1255                1260

Val Thr Ser Ala Pro Leu Leu Ser Thr Glu Ala Thr Pro Cys Phe
1265                1270                1275

Cys Thr Asp Asn Gly Gln Leu Ile Gln Met Gly Glu Asn Val Ser
1280                1285                1290

Leu Pro Met Asn Ile Ser Gly His Cys Ala Tyr Ser Ile Cys Asn
1295                1300                1305

Ala Ser Cys Gln Ile Glu Leu Ile Trp Ala Glu Cys Lys Val Val
1310                1315                1320

Gln Thr Glu Ala Leu Glu Thr Cys Glu Pro Asn Ser Glu Ala Cys
1325                1330                1335

Pro Pro Thr Ala Ala Pro Asn Ala Thr Ser Leu Val Pro Ala Thr
1340                1345                1350

Ala Leu Ala Pro Met Ser Asp Cys Leu Gly Leu Ile Pro Pro Arg
1355                1360                1365

Lys Phe Asn Glu Ser Trp Asp Phe Gly Asn Cys Gln Ile Ala Thr
1370                1375                1380

Cys Leu Gly Glu Glu Asn Asn Ile Lys Leu Ser Ser Ile Thr Cys
1385                1390                1395

Pro Pro Gln Gln Leu Lys Leu Cys Val Asn Gly Phe Pro Phe Met
1400                1405                1410

Lys His His Asp Glu Thr Gly Cys Cys Glu Val Phe Glu Cys Gln
1415                1420                1425

Cys Ile Cys Ser Gly Trp Gly Asn Glu His Tyr Val Thr Phe Asp
1430                1435                1440
```

```
Gly Thr Tyr Tyr His Phe Lys Glu Asn Cys Thr Tyr Val Leu Val
    1445                1450                1455

Glu Leu Ile Gln Pro Ser Ser Glu Lys Phe Trp Ile His Ile Asp
1460                1465                1470

Asn Tyr Tyr Cys Gly Ala Ala Asp Gly Ala Ile Cys Ser Met Ser
    1475                1480                1485

Leu Leu Ile Phe His Ser Asn Ser Leu Val Ile Leu Thr Gln Ala
    1490                1495                1500

Lys Glu His Gly Lys Gly Thr Asn Leu Val Leu Phe Asn Asp Lys
    1505                1510                1515

Lys Val Val Pro Asp Ile Ser Lys Asn Gly Ile Arg Ile Thr Ser
    1520                1525                1530

Ser Gly Leu Tyr Ile Ile Val Glu Ile Pro Glu Leu Glu Val Tyr
    1535                1540                1545

Val Ser Tyr Ser Arg Leu Ala Phe Tyr Ile Lys Leu Pro Phe Gly
    1550                1555                1560

Lys Tyr Tyr Asn Asn Thr Met Gly Leu Cys Gly Thr Cys Thr Asn
    1565                1570                1575

Gln Lys Ser Asp Asp Ala Arg Lys Arg Asn Gly Glu Val Thr Asp
    1580                1585                1590

Ser Phe Lys Glu Met Ala Leu Asp Trp Lys Ala Pro Val Ser Thr
    1595                1600                1605

Asn Arg Tyr Cys Asn Pro Gly Ile Ser Glu Pro Val Lys Ile Glu
    1610                1615                1620

Asn Tyr Gln His Cys Glu Pro Ser Glu Leu Cys Lys Ile Ile Trp
    1625                1630                1635

Asn Leu Thr Glu Cys His Arg Val Val Pro Pro Gln Pro Tyr Tyr
    1640                1645                1650

Glu Ala Cys Val Ala Ser Arg Cys Ser Gln Gln His Pro Ser Thr
    1655                1660                1665

Glu Cys Gln Ser Met Gln Thr Tyr Ala Ala Leu Cys Gly Leu His
    1670                1675                1680

Gly Ile Cys Val Asp Trp Arg Gly Gln Thr Asn Gly Gln Cys Glu
    1685                1690                1695

Ala Thr Cys Ala Arg Asp Gln Val Tyr Lys Pro Cys Gly Glu Ala
    1700                1705                1710

Lys Arg Asn Thr Cys Phe Ser Arg Glu Val Ile Val Asp Thr Leu
    1715                1720                1725

Leu Ser Arg Asn Asn Thr Pro Val Phe Val Glu Gly Cys Tyr Cys
    1730                1735                1740

Pro Asp Gly Asn Ile Leu Leu Asn Glu His Asp Gly Ile Cys Val
    1745                1750                1755

Ser Val Cys Gly Cys Thr Ala Gln Asp Gly Ser Val Lys Lys Pro
    1760                1765                1770

Arg Glu Ala Trp Glu His Asp Cys Gln Tyr Cys Thr Cys Asp Glu
    1775                1780                1785

Glu Thr Leu Asn Ile Ser Cys Phe Pro Arg Pro Cys Ala Lys Ser
    1790                1795                1800

Pro Pro Ile Asn Cys Thr Lys Glu Gly Phe Val Arg Lys Ile Lys
    1805                1810                1815

Pro Arg Leu Asp Asp Pro Cys Cys Thr Glu Thr Val Cys Glu Cys
    1820                1825                1830

Asp Ile Lys Thr Cys Ile Ile Asn Lys Thr Ala Cys Asp Leu Gly
```

```
                1835                1840                1845
Phe Gln Pro Val Val Ala Ile Ser Glu Asp Gly Cys Cys Pro Ile
        1850                1855                1860
Phe Ser Cys Ile Pro Lys Gly Val Cys Val Ser Glu Gly Val Glu
    1865                1870                1875
Phe Lys Pro Gly Ala Val Val Pro Lys Ser Ser Cys Glu Asp Cys
    1880                1885                1890
Val Cys Thr Asp Glu Gln Asp Ala Val Thr Gly Thr Asn Arg Ile
    1895                1900                1905
Gln Cys Val Pro Val Lys Cys Gln Thr Thr Cys Gln Gln Gly Phe
    1910                1915                1920
Arg Tyr Val Glu Lys Glu Gly Gln Cys Cys Ser Gln Cys Gln Gln
    1925                1930                1935
Val Ala Cys Val Ala Asn Phe Pro Phe Gly Ser Val Thr Ile Glu
    1940                1945                1950
Val Gly Lys Ser Tyr Lys Ala Pro Tyr Asp Asn Cys Thr Gln Tyr
    1955                1960                1965
Thr Cys Thr Glu Ser Gly Gly Gln Phe Ser Leu Thr Ser Thr Val
    1970                1975                1980
Lys Val Cys Leu Pro Phe Glu Glu Ser Asn Cys Val Pro Gly Thr
    1985                1990                1995
Val Asp Val Thr Ser Asp Gly Cys Cys Lys Thr Cys Ile Asp Leu
    2000                2005                2010
Pro His Lys Cys Lys Arg Ser Met Lys Glu Gln Tyr Ile Val His
    2015                2020                2025
Lys His Cys Lys Ser Ala Ala Pro Val Pro Val Pro Phe Cys Glu
    2030                2035                2040
Gly Thr Cys Ser Thr Tyr Ser Val Tyr Ser Phe Glu Asn Asn Glu
    2045                2050                2055
Met Glu His Lys Cys Ile Cys His Glu Lys Lys Ser His Val
    2060                2065                2070
Glu Lys Val Glu Leu Val Cys Ser Glu His Lys Thr Leu Lys Phe
    2075                2080                2085
Ser Tyr Val His Val Asp Glu Cys Gly Cys Val Glu Thr Lys Cys
    2090                2095                2100
Pro Met Arg Arg Thr
    2105

<210> SEQ ID NO 27
<211> LENGTH: 1185
<212> TYPE: PRT
<213> ORGANISM: Gallus gallus

<400> SEQUENCE: 27

Cys Ser Thr Trp Gly Gly His Phe Ser Thr Phe Asp Lys Tyr Gln
1               5                   10                  15
Tyr Asp Phe Thr Gly Thr Cys Asn Tyr Ile Phe Ala Thr Val Cys Asp
            20                  25                  30
Glu Ser Ser Pro Asp Phe Asn Ile Gln Phe Arg Arg Gly Leu Asp Lys
        35                  40                  45
Lys Ile Ala Arg Ile Ile Ile Glu Leu Gly Pro Ser Val Ile Val
    50                  55                  60
Glu Lys Asp Ser Ile Ser Val Arg Ser Val Gly Val Ile Lys Leu Pro
65                  70                  75                  80
```

-continued

```
Tyr Ala Ser Asn Gly Ile Gln Ile Ala Pro Tyr Gly Arg Ser Val Arg
                 85                  90                  95
Leu Val Ala Lys Leu Met Glu Met Glu Leu Val Val Met Trp Asn Asn
            100                 105                 110
Glu Asp Tyr Leu Met Val Leu Thr Glu Lys Lys Tyr Met Gly Lys Thr
        115                 120                 125
Cys Gly Met Cys Gly Asn Tyr Asp Gly Tyr Glu Leu Asn Asp Phe Val
    130                 135                 140
Ser Glu Gly Lys Leu Leu Asp Thr Tyr Lys Phe Ala Ala Leu Gln Lys
145                 150                 155                 160
Met Asp Asp Pro Ser Glu Ile Cys Leu Ser Glu Glu Ile Ser Ile Pro
                165                 170                 175
Ala Ile Pro His Lys Lys Tyr Ala Val Ile Cys Ser Gln Leu Leu Asn
            180                 185                 190
Leu Val Ser Pro Thr Cys Ser Val Pro Lys Asp Gly Phe Val Thr Arg
        195                 200                 205
Cys Gln Leu Asp Met Gln Asp Cys Ser Glu Pro Gly Lys Asn Cys
    210                 215                 220
Thr Cys Ser Thr Leu Ser Glu Tyr Ser Arg Gln Cys Ala Met Ser His
225                 230                 235                 240
Gln Val Val Phe Asn Trp Arg Thr Glu Asn Phe Cys Ser Val Gly Lys
                245                 250                 255
Cys Ser Ala Asn Gln Ile Tyr Glu Glu Cys Gly Ser Pro Cys Ile Lys
            260                 265                 270
Thr Cys Ser Asn Pro Glu Tyr Ser Cys Ser Ser His Cys Thr Tyr Gly
        275                 280                 285
Cys Phe Cys Pro Glu Gly Thr Val Leu Asp Asp Ile Ser Lys Asn Arg
    290                 295                 300
Thr Cys Val His Leu Glu Gln Cys Pro Cys Thr Leu Asn Gly Glu Thr
305                 310                 315                 320
Tyr Ala Pro Gly Asp Thr Met Lys Ala Ala Cys Arg Thr Cys Lys Cys
                325                 330                 335
Thr Met Gly Gln Trp Asn Cys Lys Glu Leu Pro Cys Pro Gly Arg Cys
            340                 345                 350
Ser Leu Glu Gly Gly Ser Phe Val Thr Thr Phe Asp Ser Arg Ser Tyr
        355                 360                 365
Arg Phe His Gly Val Cys Thr Tyr Ile Leu Met Lys Ser Ser Ser Leu
    370                 375                 380
Pro His Asn Gly Thr Leu Met Ala Ile Tyr Glu Lys Ser Gly Tyr Ser
385                 390                 395                 400
His Ser Glu Thr Ser Leu Ser Ala Ile Ile Tyr Leu Ser Thr Lys Asp
                405                 410                 415
Lys Ile Val Ile Ser Gln Asn Glu Leu Leu Thr Asp Asp Glu Leu
            420                 425                 430
Lys Arg Leu Pro Tyr Lys Ser Gly Asp Ile Thr Ile Phe Lys Gln Ser
        435                 440                 445
Ser Met Phe Ile Gln Met His Thr Glu Phe Gly Leu Glu Leu Val Val
    450                 455                 460
Gln Thr Ser Pro Val Phe Gln Ala Tyr Val Lys Val Ser Ala Gln Phe
465                 470                 475                 480
Gln Gly Arg Thr Leu Gly Leu Cys Gly Asn Tyr Asn Gly Asp Thr Thr
                485                 490                 495
Asp Asp Phe Met Thr Ser Met Asp Ile Thr Glu Gly Thr Ala Ser Leu
```

-continued

```
                500                 505                 510
Phe Val Asp Ser Trp Arg Ala Gly Asn Cys Leu Pro Ala Met Glu Arg
            515                 520                 525

Glu Thr Asp Pro Cys Ala Leu Ser Gln Leu Asn Lys Ile Ser Ala Glu
            530                 535                 540

Thr His Cys Ser Ile Leu Thr Lys Lys Gly Thr Val Phe Glu Thr Cys
545                 550                 555                 560

His Ala Val Val Asn Pro Thr Pro Phe Tyr Lys Arg Cys Val Tyr Gln
                565                 570                 575

Ala Cys Asn Tyr Glu Glu Thr Phe Pro Tyr Ile Cys Ser Ala Leu Gly
                580                 585                 590

Ser Tyr Ala Arg Thr Cys Ser Ser Met Gly Leu Ile Leu Glu Asn Trp
            595                 600                 605

Arg Asn Ser Met Asp Asn Cys Thr Ile Thr Cys Thr Gly Asn Gln Thr
            610                 615                 620

Phe Ser Tyr Asn Thr Gln Ala Cys Glu Arg Thr Cys Leu Ser Leu Ser
625                 630                 635                 640

Asn Pro Thr Leu Glu Cys His Pro Thr Asp Ile Pro Ile Glu Gly Cys
                645                 650                 655

Asn Cys Pro Lys Gly Met Tyr Leu Asn His Lys Asn Glu Cys Val Arg
            660                 665                 670

Lys Ser His Cys Pro Cys Tyr Leu Glu Asp Arg Lys Tyr Ile Leu Pro
            675                 680                 685

Asp Gln Ser Thr Met Thr Gly Gly Ile Thr Cys Tyr Cys Val Asn Gly
            690                 695                 700

Arg Leu Ser Cys Thr Gly Lys Leu Gln Asn Pro Ala Glu Ser Cys Lys
705                 710                 715                 720

Ala Pro Lys Lys Tyr Ile Ser Cys Ser Asp Ser Leu Glu Asn Lys Tyr
                725                 730                 735

Gly Ala Thr Cys Ala Pro Thr Cys Gln Met Leu Ala Thr Gly Ile Glu
            740                 745                 750

Cys Ile Pro Thr Lys Cys Glu Ser Gly Cys Val Cys Ala Asp Gly Leu
            755                 760                 765

Tyr Glu Asn Leu Asp Gly Arg Cys Val Pro Pro Glu Glu Cys Pro Cys
            770                 775                 780

Glu Tyr Gly Gly Leu Ser Tyr Gly Lys Gly Glu Gln Ile Gln Thr Glu
785                 790                 795                 800

Cys Glu Ile Cys Thr Cys Arg Lys Gly Lys Trp Lys Cys Val Gln Lys
                805                 810                 815

Ser Arg Cys Ser Ser Thr Cys Asn Leu Tyr Gly Glu Gly His Ile Thr
            820                 825                 830

Thr Phe Asp Gly Gln Arg Phe Val Phe Asp Gly Asn Cys Glu Tyr Ile
            835                 840                 845

Leu Ala Met Asp Gly Cys Asn Val Asn Arg Pro Leu Ser Ser Phe Lys
            850                 855                 860

Ile Val Thr Glu Asn Val Ile Cys Gly Lys Ser Gly Val Thr Cys Ser
865                 870                 875                 880

Arg Ser Ile Ser Ile Tyr Leu Gly Asn Leu Thr Ile Ile Leu Arg Asp
                885                 890                 895

Glu Thr Tyr Ser Ile Ser Gly Lys Asn Leu Gln Val Lys Tyr Asn Val
            900                 905                 910

Lys Lys Asn Ala Leu His Leu Met Phe Asp Ile Ile Ile Pro Gly Lys
            915                 920                 925
```

```
Tyr Asn Met Thr Leu Ile Trp Asn Lys His Met Asn Phe Phe Ile Lys
        930                 935                 940

Ile Ser Arg Glu Thr Gln Glu Thr Ile Cys Gly Leu Cys Gly Asn Tyr
945                 950                 955                 960

Asn Gly Asn Met Lys Asp Asp Phe Glu Thr Arg Ser Lys Tyr Val Ala
                965                 970                 975

Ser Asn Glu Leu Glu Phe Val Asn Ser Trp Lys Glu Asn Pro Leu Cys
            980                 985                 990

Gly Asp Val Tyr Phe Val Val Asp Pro Cys Ser Lys Asn Pro Tyr Arg
        995                 1000                1005

Lys Ala Trp Ala Glu Lys Thr Cys Ser Ile Ile Asn Ser Gln Val
    1010                1015                1020

Phe Ser Ala Cys His Asn Lys Val Asn Arg Met Pro Tyr Tyr Glu
    1025                1030                1035

Ala Cys Val Arg Asp Ser Cys Gly Cys Asp Ile Gly Gly Asp Cys
    1040                1045                1050

Glu Cys Met Cys Asp Ala Ile Ala Val Tyr Ala Met Ala Cys Leu
    1055                1060                1065

Asp Lys Gly Ile Cys Ile Asp Trp Arg Thr Pro Glu Phe Cys Pro
    1070                1075                1080

Val Tyr Cys Glu Tyr Tyr Asn Ser His Arg Lys Thr Gly Ser Gly
    1085                1090                1095

Gly Ala Tyr Ser Tyr Gly Ser Ser Val Asn Cys Thr Trp His Tyr
    1100                1105                1110

Arg Pro Cys Asn Cys Pro Asn Gln Tyr Tyr Lys Tyr Val Asn Ile
    1115                1120                1125

Glu Gly Cys Tyr Asn Cys Ser His Asp Glu Tyr Phe Asp Tyr Glu
    1130                1135                1140

Lys Glu Lys Cys Met Pro Cys Ala Met Gln Pro Thr Ser Val Thr
    1145                1150                1155

Leu Pro Thr Ala Thr Gln Pro Thr Ser Pro Ser Thr Ser Ser Ala
    1160                1165                1170

Ser Thr Val Leu Thr Glu Thr Thr Asn Pro Pro Val
    1175                1180                1185

<210> SEQ ID NO 28
<211> LENGTH: 211
<212> TYPE: PRT
<213> ORGANISM: Gallus gallus

<400> SEQUENCE: 28

Met Leu Gly Lys Asn Asp Pro Met Cys Leu Val Leu Val Leu Leu Gly
1               5                   10                  15

Leu Thr Ala Leu Leu Gly Ile Cys Gln Gly Gly Thr Gly Cys Tyr Gly
            20                  25                  30

Ser Val Ser Arg Ile Asp Thr Thr Gly Ala Ser Cys Arg Thr Ala Lys
        35                  40                  45

Pro Glu Gly Leu Ser Tyr Cys Gly Val Arg Ala Ser Arg Thr Ile Ala
    50                  55                  60

Glu Arg Asp Leu Gly Ser Met Asn Lys Tyr Lys Val Leu Ile Lys Arg
65                  70                  75                  80

Val Gly Glu Ala Leu Cys Ile Glu Pro Ala Val Ile Ala Gly Ile Ile
                85                  90                  95

Ser Arg Glu Ser His Ala Gly Lys Ile Leu Lys Asn Gly Trp Gly Asp
```

```
                 100                 105                 110
Arg Gly Asn Gly Phe Gly Leu Met Gln Val Asp Lys Arg Tyr His Lys
            115                 120                 125

Ile Glu Gly Thr Trp Asn Gly Glu Ala His Ile Arg Gln Gly Thr Arg
        130                 135                 140

Ile Leu Ile Asp Met Val Lys Lys Ile Gln Arg Lys Phe Pro Arg Trp
145                 150                 155                 160

Thr Arg Asp Gln Gln Leu Lys Gly Gly Ile Ser Ala Tyr Asn Ala Gly
            165                 170                 175

Val Gly Asn Val Arg Ser Tyr Glu Arg Met Asp Ile Gly Thr Leu His
        180                 185                 190

Asp Asp Tyr Ser Asn Asp Val Val Ala Arg Ala Gln Tyr Phe Lys Gln
            195                 200                 205

His Gly Tyr
    210

<210> SEQ ID NO 29
<211> LENGTH: 147
<212> TYPE: PRT
<213> ORGANISM: Gallus gallus

<400> SEQUENCE: 29

Met Arg Ser Leu Leu Ile Leu Val Leu Cys Phe Leu Pro Leu Ala Ala
1               5                   10                  15

Leu Gly Lys Val Phe Gly Arg Cys Glu Leu Ala Ala Ala Met Lys Arg
            20                  25                  30

His Gly Leu Asp Asn Tyr Arg Gly Tyr Ser Leu Gly Asn Trp Val Cys
        35                  40                  45

Ala Ala Lys Phe Glu Ser Asn Phe Asn Thr Gln Ala Thr Asn Arg Asn
    50                  55                  60

Thr Asp Gly Ser Thr Asp Tyr Gly Ile Leu Gln Ile Asn Ser Arg Trp
65                  70                  75                  80

Trp Cys Asn Asp Gly Arg Thr Pro Gly Ser Arg Asn Leu Cys Asn Ile
                85                  90                  95

Pro Cys Ser Ala Leu Leu Ser Ser Asp Ile Thr Ala Ser Val Asn Cys
            100                 105                 110

Ala Lys Lys Ile Val Ser Asp Gly Asn Gly Met Asn Ala Trp Val Ala
        115                 120                 125

Trp Arg Asn Arg Cys Lys Gly Thr Asp Val Gln Ala Trp Ile Arg Gly
    130                 135                 140

Cys Arg Leu
145

<210> SEQ ID NO 30
<211> LENGTH: 1453
<212> TYPE: PRT
<213> ORGANISM: Gallus gallus

<400> SEQUENCE: 30

Met Phe Ser Phe Val Asp Ser Arg Leu Leu Leu Leu Ile Ala Ala Thr
1               5                   10                  15

Val Leu Leu Thr Arg Gly Glu Gly Glu Asp Ile Gln Thr Gly Ser
            20                  25                  30

Cys Val Gln Asp Gly Leu Thr Tyr Asn Asp Lys Asp Val Trp Lys Pro
        35                  40                  45

Glu Pro Cys Gln Ile Cys Val Cys Asp Ser Gly Asn Ile Leu Cys Asp
```

-continued

```
            50                  55                  60
Glu Val Ile Cys Glu Asp Thr Ser Asp Cys Pro Asn Ala Glu Ile Pro
 65                  70                  75                  80
Phe Gly Glu Cys Cys Pro Ile Cys Pro Asp Val Asp Ala Ser Pro Val
                     85                  90                  95
Tyr Pro Glu Ser Ala Gly Val Glu Gly Pro Lys Gly Asp Thr Gly Pro
                100                 105                 110
Arg Gly Asp Arg Gly Leu Pro Gly Pro Pro Gly Arg Asp Gly Ile Pro
                115                 120                 125
Gly Gln Pro Gly Leu Pro Gly Pro Pro Gly Pro Pro Gly Pro Pro Gly
                130                 135                 140
Leu Gly Gly Asn Phe Ala Pro Gln Met Ser Tyr Gly Tyr Asp Glu Lys
145                 150                 155                 160
Ser Ala Gly Val Ala Val Pro Gly Pro Met Gly Pro Ala Gly Pro Arg
                165                 170                 175
Gly Leu Pro Gly Pro Pro Gly Ala Pro Gly Pro Gln Gly Phe Gln Gly
                180                 185                 190
Pro Pro Gly Glu Pro Gly Glu Pro Gly Ala Ser Gly Pro Met Gly Pro
                195                 200                 205
Arg Gly Pro Ala Gly Pro Pro Gly Lys Asn Gly Asp Asp Gly Glu Ala
                210                 215                 220
Gly Lys Pro Gly Arg Pro Gly Gln Arg Gly Pro Pro Gly Pro Gln Gly
225                 230                 235                 240
Ala Arg Gly Leu Pro Gly Thr Ala Gly Leu Pro Gly Met Lys Gly His
                245                 250                 255
Arg Gly Phe Ser Gly Leu Asp Gly Ala Lys Gly Gln Pro Gly Pro Ala
                260                 265                 270
Gly Pro Lys Gly Glu Pro Gly Ser Pro Gly Glu Asn Gly Ala Pro Gly
                275                 280                 285
Gln Met Gly Pro Arg Gly Leu Pro Gly Glu Arg Gly Arg Pro Gly Pro
                290                 295                 300
Ser Gly Pro Ala Gly Ala Arg Gly Asn Asp Gly Ala Pro Gly Ala Ala
305                 310                 315                 320
Gly Pro Pro Gly Pro Thr Gly Pro Ala Gly Pro Pro Gly Phe Pro Gly
                325                 330                 335
Ala Ala Gly Ala Lys Gly Glu Thr Gly Pro Gln Gly Ala Arg Gly Ser
                340                 345                 350
Glu Gly Pro Gln Gly Ser Arg Gly Glu Pro Gly Pro Pro Gly Pro Ala
                355                 360                 365
Gly Ala Ala Gly Pro Ala Gly Asn Pro Gly Ala Asp Gly Gln Pro Gly
                370                 375                 380
Ala Lys Gly Ala Thr Gly Ala Pro Gly Ile Ala Gly Ala Pro Gly Phe
385                 390                 395                 400
Pro Gly Ala Arg Gly Pro Ser Gly Pro Gln Gly Pro Ser Gly Ala Pro
                405                 410                 415
Gly Pro Lys Gly Asn Ser Gly Glu Pro Gly Ala Pro Gly Asn Lys Gly
                420                 425                 430
Asp Thr Gly Ala Lys Gly Glu Pro Gly Ala Gly Val Gln Gly Pro
                435                 440                 445
Pro Gly Pro Ala Gly Glu Glu Gly Lys Arg Gly Ala Arg Gly Glu Pro
                450                 455                 460
Gly Pro Ala Gly Leu Pro Gly Pro Ala Gly Glu Arg Gly Ala Pro Gly
465                 470                 475                 480
```

```
Ser Arg Gly Phe Pro Gly Ala Asp Gly Ile Ala Gly Pro Lys Gly Pro
            485                 490                 495

Pro Gly Glu Arg Gly Ser Pro Gly Ala Val Gly Pro Lys Gly Ser Pro
            500                 505                 510

Gly Glu Ala Gly Arg Pro Gly Glu Ala Gly Leu Pro Gly Ala Lys Gly
            515                 520                 525

Leu Thr Gly Ser Pro Gly Ser Pro Gly Pro Asp Gly Lys Thr Gly Pro
            530                 535                 540

Pro Gly Pro Ala Gly Gln Asp Gly Arg Pro Gly Pro Ala Gly Pro Pro
545                 550                 555                 560

Gly Ala Arg Gly Gln Ala Gly Val Met Gly Phe Pro Gly Pro Lys Gly
            565                 570                 575

Ala Ala Gly Glu Pro Gly Lys Pro Gly Glu Arg Gly Ala Pro Gly Pro
            580                 585                 590

Pro Gly Ala Val Gly Ala Ala Gly Lys Asp Gly Glu Ala Gly Ala Gln
            595                 600                 605

Gly Pro Pro Gly Pro Thr Gly Pro Ala Gly Glu Arg Gly Glu Gln Gly
            610                 615                 620

Pro Ala Gly Ala Pro Gly Phe Gln Gly Leu Pro Gly Pro Ala Gly Pro
625                 630                 635                 640

Pro Gly Glu Ala Gly Lys Pro Gly Glu Gln Gly Val Pro Gly Asn Ala
            645                 650                 655

Gly Ala Pro Gly Pro Ala Gly Ala Arg Gly Glu Arg Gly Phe Pro Gly
            660                 665                 670

Glu Arg Gly Val Gln Gly Pro Pro Gly Pro Gln Gly Pro Arg Gly Ala
            675                 680                 685

Asn Gly Ala Pro Gly Asn Asp Gly Ala Lys Gly Asp Ala Gly Ala Pro
            690                 695                 700

Gly Ala Pro Gly Asn Glu Gly Pro Pro Gly Leu Glu Gly Met Pro Gly
705                 710                 715                 720

Glu Arg Gly Ala Ala Gly Leu Pro Gly Ala Lys Gly Asp Arg Gly Asp
            725                 730                 735

Pro Gly Pro Lys Gly Ala Asp Gly Ala Pro Gly Lys Asp Gly Leu Arg
            740                 745                 750

Gly Leu Thr Gly Pro Ile Gly Pro Pro Gly Pro Ala Gly Ala Pro Gly
            755                 760                 765

Asp Lys Gly Glu Ala Gly Pro Pro Gly Pro Ala Gly Pro Thr Gly Ala
            770                 775                 780

Arg Gly Ala Pro Gly Asp Arg Gly Glu Pro Gly Pro Pro Gly Pro Ala
785                 790                 795                 800

Gly Phe Ala Gly Pro Pro Gly Ala Asp Gly Gln Pro Gly Ala Lys Gly
            805                 810                 815

Glu Thr Gly Asp Ala Gly Ala Lys Gly Asp Ala Gly Pro Pro Gly Pro
            820                 825                 830

Ala Gly Pro Thr Gly Ala Pro Gly Pro Ala Gly Glx Val Gly Ala Pro
            835                 840                 845

Gly Pro Lys Gly Ala Arg Gly Ser Ala Gly Pro Pro Gly Ala Thr Gly
            850                 855                 860

Phe Pro Gly Ala Ala Gly Arg Val Gly Pro Pro Gly Pro Ser Gly Asn
865                 870                 875                 880

Ile Gly Leu Pro Gly Pro Pro Gly Pro Ala Gly Lys Glx Gly Ser Lys
            885                 890                 895
```

Gly Pro Arg Gly Glu Thr Gly Pro Ala Gly Arg Pro Gly Glu Pro Gly
                900                 905                 910

Pro Ala Gly Pro Pro Gly Pro Pro Gly Glu Lys Gly Ser Pro Gly Ala
        915                 920                 925

Asp Gly Pro Ile Gly Ala Pro Gly Thr Pro Gly Pro Gln Gly Ile Ala
        930                 935                 940

Gly Gln Arg Gly Val Val Gly Leu Pro Gly Gln Arg Gly Glu Arg Gly
945                 950                 955                 960

Phe Pro Gly Leu Pro Gly Pro Ser Gly Glu Pro Gly Lys Gln Gly Pro
                965                 970                 975

Ser Gly Ala Ser Gly Glu Arg Gly Pro Pro Gly Pro Met Gly Pro Pro
        980                 985                 990

Gly Leu Ala Gly Pro Pro Gly Glu Ala Gly Arg Glu Gly Ala Pro Gly
        995                 1000                1005

Ala Glu Gly Ala Pro Gly Arg Asp Gly Ala Ala Gly Pro Lys Gly
        1010                1015                1020

Asp Arg Gly Glu Thr Gly Pro Ala Gly Pro Pro Gly Ala Pro Gly
        1025                1030                1035

Ala Pro Gly Ala Pro Gly Pro Val Gly Pro Ala Gly Lys Asn Gly
        1040                1045                1050

Asp Arg Gly Glu Thr Gly Pro Ala Gly Pro Ala Gly Pro Pro Gly
        1055                1060                1065

Pro Ala Gly Ala Arg Gly Pro Ala Gly Pro Gln Gly Pro Arg Gly
        1070                1075                1080

Asp Lys Gly Glu Thr Gly Glu Gln Gly Asp Arg Gly Met Lys Gly
        1085                1090                1095

His Arg Gly Phe Ser Gly Leu Gln Gly Pro Pro Gly Pro Pro Gly
        1100                1105                1110

Ala Pro Gly Glu Gln Gly Pro Ser Gly Ala Ser Gly Pro Ala Gly
        1115                1120                1125

Pro Arg Gly Pro Pro Gly Ser Ala Gly Ala Ala Gly Lys Asp Gly
        1130                1135                1140

Leu Asn Gly Leu Pro Gly Pro Ile Gly Pro Pro Gly Pro Arg Gly
        1145                1150                1155

Arg Thr Gly Glu Val Gly Pro Val Gly Pro Pro Gly Pro Pro Gly
        1160                1165                1170

Pro Pro Gly Pro Pro Gly Pro Pro Ser Gly Gly Phe Asp Leu Ser
        1175                1180                1185

Phe Leu Pro Gln Pro Pro Gln Glu Lys Ala His Asp Gly Gly Arg
        1190                1195                1200

Tyr Tyr Arg Ala Asp Asp Ala Asn Val Met Arg Asp Arg Asp Leu
        1205                1210                1215

Glu Val Asp Thr Thr Leu Lys Ser Leu Ser Gln Gln Ile Glu Asn
        1220                1225                1230

Ile Arg Ser Pro Glu Gly Thr Arg Lys Asn Pro Ala Arg Thr Cys
        1235                1240                1245

Arg Asp Leu Lys Met Cys His Gly Asp Trp Lys Ser Gly Glu Tyr
        1250                1255                1260

Trp Ile Asp Pro Asn Gln Gly Cys Asn Leu Asp Ala Ile Lys Val
        1265                1270                1275

Tyr Cys Asn Met Glu Thr Gly Glu Thr Cys Val Tyr Pro Thr Gln
        1280                1285                1290

Ala Thr Ile Ala Gln Lys Asn Trp Tyr Leu Ser Lys Asn Pro Lys

```
                    1295                1300                1305

Glu  Lys  Lys  His  Val  Trp  Phe  Gly  Glu  Thr  Met  Ser  Asp  Gly  Phe
         1310                1315                1320

Gln  Phe  Glu  Tyr  Gly  Gly  Glu  Gly  Ser  Asn  Pro  Ala  Asp  Val  Ala
    1325                1330                1335

Ile  Gln  Leu  Thr  Phe  Leu  Arg  Leu  Met  Ser  Thr  Glu  Ala  Thr  Gln
    1340                1345                1350

Asn  Val  Thr  Tyr  His  Cys  Lys  Asn  Ser  Val  Ala  Tyr  Met  Asp  His
    1355                1360                1365

Asp  Thr  Gly  Asn  Leu  Lys  Lys  Ala  Leu  Leu  Leu  Gln  Gly  Ala  Asn
    1370                1375                1380

Glu  Ile  Glu  Ile  Arg  Ala  Glu  Gly  Asn  Ser  Arg  Phe  Thr  Tyr  Gly
    1385                1390                1395

Val  Thr  Glu  Asp  Gly  Cys  Thr  Ser  His  Thr  Gly  Ala  Trp  Gly  Lys
    1400                1405                1410

Thr  Val  Ile  Glu  Tyr  Lys  Thr  Thr  Lys  Thr  Ser  Arg  Leu  Pro  Ile
    1415                1420                1425

Ile  Asp  Leu  Ala  Pro  Met  Asp  Val  Gly  Ala  Pro  Asp  Gln  Glu  Phe
    1430                1435                1440

Gly  Ile  Asp  Ile  Gly  Pro  Val  Cys  Phe  Leu
    1445                1450

<210> SEQ ID NO 31
<211> LENGTH: 369
<212> TYPE: PRT
<213> ORGANISM: Gallus gallus

<400> SEQUENCE: 31

Gly  Glu  Thr  Gly  Glu  Ala  Gly  Glu  Arg  Gly  Leu  Lys  Gly  His  Arg  Gly
1                5                  10                  15

Phe  Thr  Gly  Leu  Gln  Gly  Leu  Pro  Gly  Pro  Pro  Gly  Pro  Ser  Gly  Asp
            20                  25                  30

Gln  Gly  Ala  Ala  Gly  Pro  Ala  Gly  Pro  Ser  Gly  Pro  Arg  Gly  Pro  Pro
        35                  40                  45

Gly  Pro  Val  Gly  Pro  Ser  Gly  Lys  Asp  Gly  Ser  Asn  Gly  Met  Pro  Gly
    50                  55                  60

Pro  Ile  Gly  Pro  Pro  Gly  Pro  Arg  Gly  Arg  Ser  Gly  Glu  Pro  Gly  Pro
65                  70                  75                  80

Ala  Gly  Pro  Pro  Gly  Asn  Pro  Gly  Pro  Pro  Gly  Pro  Pro  Gly  Pro  Pro
                85                  90                  95

Gly  Thr  Gly  Ile  Asp  Met  Ser  Ala  Phe  Ala  Gly  Leu  Gly  Gln  Thr  Glu
            100                 105                 110

Lys  Gly  Pro  Asp  Pro  Ile  Arg  Tyr  Met  Arg  Ala  Asp  Glu  Ala  Ala  Gly
        115                 120                 125

Gly  Leu  Arg  Gln  His  Asp  Val  Glu  Val  Asp  Ala  Thr  Leu  Lys  Ser  Leu
    130                 135                 140

Asn  Asn  Gln  Ile  Glu  Ser  Ile  Arg  Ser  Pro  Glu  Gly  Ser  Lys  Lys  Asn
145                 150                 155                 160

Pro  Ala  Arg  Thr  Cys  Arg  Asp  Ile  Lys  Leu  Cys  His  Pro  Glu  Trp  Lys
                165                 170                 175

Ser  Gly  Asp  Tyr  Trp  Ile  Asp  Pro  Asn  Gln  Gly  Cys  Thr  Leu  Asp  Ala
            180                 185                 190

Ile  Lys  Val  Phe  Cys  Asn  Met  Glu  Thr  Gly  Glu  Thr  Cys  Val  Tyr  Pro
        195                 200                 205
```

-continued

```
Thr Pro Ser Ser Ile Pro Arg Lys Asn Trp Trp Thr Ser Lys Thr Lys
    210                 215                 220

Asp Lys Lys His Val Trp Phe Ala Glu Thr Ile Asn Gly Gly Phe His
225                 230                 235                 240

Phe Ser Tyr Gly Asp Glu Asn Leu Ser Pro Asn Thr Ala Ser Ile Gln
                245                 250                 255

Met Thr Phe Leu Arg Leu Leu Ser Thr Glu Gly Ser Gln Asn Val Thr
            260                 265                 270

Tyr His Cys Lys Asn Ser Ile Ala Tyr Met Asp Glu Thr Gly Asn
            275                 280                 285

Leu Lys Lys Ala Ile Leu Ile Gln Gly Ser Asn Asp Val Glu Ile Arg
    290                 295                 300

Ala Glu Gly Asn Ser Arg Phe Thr Tyr Ser Val Leu Glu Asp Gly Cys
305                 310                 315                 320

Thr Lys His Thr Gly Lys Trp Gly Lys Thr Val Ile Glu Tyr Arg Ser
                325                 330                 335

Gln Lys Thr Ser Arg Leu Pro Ile Val Asp Ile Ala Pro Met Asp Ile
            340                 345                 350

Gly Gly Ala Asp Gln Glu Phe Gly Val Asp Ile Gly Pro Val Cys Phe
            355                 360                 365

Leu

<210> SEQ ID NO 32
<211> LENGTH: 1362
<212> TYPE: PRT
<213> ORGANISM: Gallus gallus
<220> FEATURE:
<221> NAME/KEY: misc_feature
<222> LOCATION: (246)..(262)
<223> OTHER INFORMATION: Xaa can be any naturally occurring amino acid
<220> FEATURE:
<221> NAME/KEY: misc_feature
<222> LOCATION: (449)..(466)
<223> OTHER INFORMATION: Xaa can be any naturally occurring amino acid

<400> SEQUENCE: 32

Met Leu Ser Phe Val Asp Thr Arg Ile Leu Leu Leu Ala Val Thr
1               5                   10                  15

Ser Tyr Leu Ala Thr Ser Gln His Val Ser Glu Ala Ser Ala Gly Arg
            20                  25                  30

Lys Gly Pro Arg Gly Asp Lys Gly Pro Gln Gly Glu Arg Gly Pro Pro
        35                  40                  45

Gly Pro Pro Gly Arg Asp Gly Glu Asp Gly Pro Pro Gly Pro Pro Gly
    50                  55                  60

Pro Pro Gly Pro Pro Gly Leu Gly Gly Asn Phe Ala Ala Gln Tyr Asp
65                  70                  75                  80

Pro Ser Lys Ala Ala Asp Phe Gly Pro Gly Pro Met Gly Leu Met Gly
                85                  90                  95

Pro Arg Gly Pro Pro Gly Ala Ser Gly Pro Gly Pro Gly Pro Gly Phe
            100                 105                 110

Gln Gly Val Pro Gly Glu Pro Gly Glu Pro Gly Gln Thr Gly Pro Gln
        115                 120                 125

Gly Pro Arg Gly Pro Pro Gly Pro Pro Gly Lys Ala Gly Glu Asp Gly
    130                 135                 140

His Pro Gly Lys Pro Gly Arg Pro Gly Glu Arg Gly Val Ala Gly Pro
145                 150                 155                 160

Gln Gly Ala Arg Gly Phe Pro Gly Thr Pro Gly Pro Pro Gly Phe Lys
```

```
              165                 170                 175
Gly Ile Arg Gly His Asn Gly Leu Asp Gly Leu Thr Gly Gln Pro Gly
            180                 185                 190

Ala Pro Gly Thr Lys Gly Glu Pro Gly Ala Pro Gly Glu Asn Gly Thr
            195                 200                 205

Pro Gly Gln Pro Gly Ala Arg Gly Leu Pro Gly Glu Arg Gly Arg Ile
            210                 215                 220

Gly Ala Pro Gly Pro Ala Gly Ala Arg Gly Ser Asp Gly Ser Ala Gly
225                 230                 235                 240

Pro Thr Gly Pro Ala Xaa Xaa Xaa Xaa Xaa Xaa Xaa Xaa Xaa Xaa Xaa
            245                 250                 255

Xaa Xaa Xaa Xaa Xaa Xaa Gly Glu Ile Gly Pro Ala Gly Asn Glu Gly
            260                 265                 270

Pro Thr Gly Pro Ala Gly Pro Arg Gly Glu Ile Gly Leu Pro Gly Ser
            275                 280                 285

Ser Gly Pro Val Gly Pro Pro Gly Asn Pro Gly Ala Asn Gly Leu Pro
            290                 295                 300

Gly Ala Lys Gly Ala Ala Gly Leu Pro Gly Val Ala Gly Ala Pro Gly
305                 310                 315                 320

Leu Pro Gly Pro Arg Gly Ile Pro Gly Pro Pro Gly Pro Ala Gly Pro
            325                 330                 335

Ser Gly Ala Arg Gly Leu Val Gly Glu Pro Gly Pro Ala Gly Ala Lys
            340                 345                 350

Gly Glu Ser Gly Asn Lys Gly Glu Pro Gly Ala Ala Gly Pro Pro Gly
            355                 360                 365

Pro Pro Gly Pro Ser Gly Glu Glu Gly Lys Arg Gly Ser Asn Gly Glu
            370                 375                 380

Pro Gly Ser Ala Gly Pro Pro Gly Pro Ala Gly Leu Arg Gly Glu Pro
385                 390                 395                 400

Gly Ser Arg Gly Leu Pro Gly Ala Asp Gly Arg Ala Gly Val Met Gly
            405                 410                 415

Pro Ala Gly Asn Arg Gly Ala Ser Gly Pro Val Gly Ala Lys Gly Pro
            420                 425                 430

Asn Gly Asp Ala Gly Arg Pro Gly Glu Pro Gly Leu Met Gly Pro Arg
            435                 440                 445

Xaa Xaa Xaa Xaa Xaa Xaa Xaa Xaa Xaa Xaa Xaa Xaa Xaa Xaa Xaa Xaa
            450                 455                 460

Xaa Xaa Gly Phe Pro Gly Ala Asp Gly Arg Val Gly Pro Ile Gly Pro
465                 470                 475                 480

Ala Gly Asn Arg Gly Glu Pro Gly Asn Ile Gly Phe Pro Gly Pro Lys
            485                 490                 495

Gly Pro Thr Gly Glu Pro Gly Lys Pro Gly Glu Lys Gly Asn Val Gly
            500                 505                 510

Leu Ala Gly Pro Arg Gly Ala Pro Gly Pro Glu Gly Asn Asn Gly Ala
            515                 520                 525

Gln Gly Pro Pro Gly Val Thr Gly Asn Gln Gly Ala Lys Gly Glu Thr
            530                 535                 540

Gly Pro Ala Gly Pro Pro Gly Phe Gln Gly Leu Pro Gly Pro Ser Gly
545                 550                 555                 560

Pro Ala Gly Glu Ala Gly Lys Pro Gly Glu Arg Gly Leu His Gly Glu
            565                 570                 575

Phe Gly Val Pro Gly Pro Ala Gly Pro Arg Gly Glu Arg Gly Leu Pro
            580                 585                 590
```

```
Gly Glu Ser Gly Ala Val Gly Pro Ala Gly Pro Ile Gly Ser Arg Gly
            595                 600                 605

Pro Ser Gly Pro Pro Gly Pro Asp Gly Asn Lys Gly Glu Pro Gly Asn
    610                 615                 620

Val Gly Pro Ala Gly Ala Pro Gly Pro Ala Gly Pro Gly Gly Ile Pro
625                 630                 635                 640

Gly Glu Arg Gly Val Ala Gly Val Pro Gly Gly Lys Gly Glu Lys Gly
                645                 650                 655

Ala Pro Gly Leu Arg Gly Asp Thr Gly Ala Thr Gly Arg Asp Gly Ala
            660                 665                 670

Arg Gly Leu Pro Gly Ala Ile Gly Ala Pro Gly Pro Ala Gly Gly Ala
            675                 680                 685

Gly Asp Arg Gly Glu Gly Gly Pro Ala Gly Pro Ala Gly Pro Ala Gly
            690                 695                 700

Ala Arg Gly Ile Pro Gly Glu Arg Gly Glu Pro Gly Pro Val Gly Pro
705                 710                 715                 720

Ser Gly Phe Ala Gly Pro Pro Gly Ala Ala Gly Gln Pro Gly Ala Lys
                725                 730                 735

Gly Glu Arg Gly Pro Lys Gly Pro Lys Gly Glu Thr Gly Pro Thr Gly
            740                 745                 750

Ala Ile Gly Pro Ile Gly Ala Ser Gly Pro Pro Gly Pro Val Gly Ala
            755                 760                 765

Ala Gly Pro Ala Gly Pro Arg Gly Asp Ala Gly Pro Pro Gly Met Thr
770                 775                 780

Gly Phe Pro Gly Ala Ala Gly Arg Val Gly Pro Pro Gly Pro Ala Gly
785                 790                 795                 800

Ile Thr Gly Pro Pro Gly Pro Pro Gly Ala Gly Lys Asp Gly Pro
                805                 810                 815

Arg Gly Leu Arg Gly Asp Val Gly Pro Val Gly Arg Thr Gly Glu Gln
                820                 825                 830

Gly Ile Ala Gly Pro Pro Gly Phe Ala Gly Glu Lys Gly Pro Ser Gly
            835                 840                 845

Glu Ala Gly Ala Ala Gly Pro Pro Gly Thr Pro Gly Pro Gln Gly Ile
    850                 855                 860

Leu Gly Ala Pro Gly Ile Leu Gly Leu Pro Gly Ser Arg Gly Glu Arg
865                 870                 875                 880

Gly Leu Pro Gly Ile Ala Gly Ala Thr Gly Glu Pro Gly Pro Leu Gly
                885                 890                 895

Val Ser Gly Pro Pro Gly Ala Arg Gly Pro Ser Gly Pro Val Gly Ser
            900                 905                 910

Pro Gly Pro Asn Gly Ala Pro Gly Glu Ala Gly Arg Asp Gly Asn Pro
            915                 920                 925

Gly Asn Asp Gly Pro Pro Gly Arg Asp Gly Ala Pro Gly Phe Lys Gly
930                 935                 940

Glu Arg Gly Ala Pro Gly Asn Pro Gly Pro Ser Gly Ala Leu Gly Ala
945                 950                 955                 960

Pro Gly Pro His Gly Gln Val Gly Pro Ser Gly Lys Pro Gly Asn Arg
                965                 970                 975

Gly Asp Pro Gly Pro Val Gly Pro Val Gly Pro Ala Gly Ala Phe Gly
            980                 985                 990

Pro Arg Gly Leu Ala Gly Pro Gln  Gly Pro Arg Gly Glu  Lys Gly Glu
            995                 1000                1005
```

-continued

| | | | | | | | | | |
|---|---|---|---|---|---|---|---|---|---|
| Pro | Gly | Asp | Lys | Gly | His | Arg | Gly | Leu | Pro | Gly | Leu | Lys | Gly | His |
| 1010 | | | | | 1015 | | | | | 1020 | | | | |
| Asn | Gly | Leu | Gln | Gly | Leu | Pro | Gly | Leu | Ala | Gly | Gln | His | Gly | Asp |
| 1025 | | | | | 1030 | | | | | 1035 | | | | |
| Gln | Gly | Pro | Pro | Gly | Asn | Asn | Gly | Pro | Ala | Gly | Pro | Arg | Gly | Pro |
| 1040 | | | | | 1045 | | | | | 1050 | | | | |
| Pro | Gly | Pro | Ser | Gly | Pro | Pro | Gly | Lys | Asp | Gly | Arg | Asn | Gly | Leu |
| 1055 | | | | | 1060 | | | | | 1065 | | | | |
| Pro | Gly | Pro | Ile | Gly | Pro | Ala | Gly | Val | Arg | Gly | Ser | His | Gly | Ser |
| 1070 | | | | | 1075 | | | | | 1080 | | | | |
| Gln | Gly | Pro | Ala | Gly | Pro | Gly | Pro | Pro | Gly | Pro | Pro | Gly | Pro |
| 1085 | | | | | 1090 | | | | | 1095 | | | | |
| Pro | Gly | Pro | Asn | Gly | Gly | Gly | Tyr | Glu | Val | Gly | Phe | Asp | Ala | Glu |
| 1100 | | | | | 1105 | | | | | 1110 | | | | |
| Tyr | Tyr | Arg | Ala | Asp | Gln | Pro | Ser | Leu | Arg | Pro | Lys | Asp | Tyr | Glu |
| 1115 | | | | | 1120 | | | | | 1125 | | | | |
| Val | Asp | Ala | Thr | Leu | Lys | Thr | Leu | Asn | Asn | Gln | Ile | Glu | Thr | Leu |
| 1130 | | | | | 1135 | | | | | 1140 | | | | |
| Leu | Thr | Pro | Glu | Gly | Ser | Lys | Lys | Asn | Pro | Ala | Arg | Thr | Cys | Arg |
| 1145 | | | | | 1150 | | | | | 1155 | | | | |
| Asp | Leu | Arg | Leu | Ser | His | Pro | Glu | Trp | Ser | Ser | Gly | Phe | Tyr | Trp |
| 1160 | | | | | 1165 | | | | | 1170 | | | | |
| Ile | Asp | Pro | Asn | Gln | Gly | Cys | Thr | Ala | Asp | Ala | Ile | Arg | Ala | Tyr |
| 1175 | | | | | 1180 | | | | | 1185 | | | | |
| Cys | Asp | Phe | Ala | Thr | Gly | Glu | Thr | Cys | Ile | His | Ala | Ser | Leu | Glu |
| 1190 | | | | | 1195 | | | | | 1200 | | | | |
| Asp | Ile | Pro | Thr | Lys | Thr | Trp | Tyr | Val | Ser | Lys | Asn | Pro | Lys | Asp |
| 1205 | | | | | 1210 | | | | | 1215 | | | | |
| Lys | Lys | His | Ile | Trp | Phe | Gly | Glu | Thr | Ile | Asn | Gly | Gly | Thr | Gln |
| 1220 | | | | | 1225 | | | | | 1230 | | | | |
| Phe | Glu | Tyr | Asn | Gly | Glu | Gly | Val | Thr | Thr | Lys | Asp | Met | Ala | Thr |
| 1235 | | | | | 1240 | | | | | 1245 | | | | |
| Gln | Leu | Ala | Phe | Met | Arg | Leu | Leu | Ala | Asn | His | Ala | Ser | Gln | Asn |
| 1250 | | | | | 1255 | | | | | 1260 | | | | |
| Ile | Thr | Tyr | His | Cys | Lys | Asn | Ser | Ile | Ala | Tyr | Met | Asp | Glu | Glu |
| 1265 | | | | | 1270 | | | | | 1275 | | | | |
| Thr | Gly | Asn | Leu | Lys | Lys | Ala | Val | Ile | Leu | Gln | Gly | Ser | Asn | Asp |
| 1280 | | | | | 1285 | | | | | 1290 | | | | |
| Val | Glu | Leu | Arg | Ala | Glu | Gly | Asn | Ser | Arg | Phe | Thr | Phe | Ser | Val |
| 1295 | | | | | 1300 | | | | | 1305 | | | | |
| Leu | Val | Asp | Gly | Cys | Ser | Lys | Lys | Asn | Asn | Lys | Trp | Gly | Lys | Thr |
| 1310 | | | | | 1315 | | | | | 1320 | | | | |
| Ile | Ile | Glu | Tyr | Arg | Thr | Asn | Lys | Pro | Ser | Arg | Leu | Pro | Ile | Leu |
| 1325 | | | | | 1330 | | | | | 1335 | | | | |
| Asp | Ile | Ala | Pro | Leu | Asp | Ile | Gly | Gly | Ala | Asp | Gln | Glu | Phe | Gly |
| 1340 | | | | | 1345 | | | | | 1350 | | | | |
| Leu | His | Ile | Gly | Pro | Val | Cys | Phe | Lys | | | | | | |
| 1355 | | | | | 1360 | | | | | | | | | |

<210> SEQ ID NO 33
<211> LENGTH: 216
<212> TYPE: PRT
<213> ORGANISM: Hordeum vulgare subsp. spontaneum

<400> SEQUENCE: 33

```
Met Glu Thr Phe Leu Ile Leu Ser Leu Ile Ala Ile Val Ala Thr Thr
1               5                   10                  15

Ala Thr Thr Ala Val Arg Val Pro Val Pro Gln Leu Gln Leu Gln Asn
            20                  25                  30

Pro Ser Met Gln Gln Pro Gln Glu Gln Val Pro Leu Val Gln Gln Gln
        35                  40                  45

Gln Phe Leu Gly Gln Gln Gln Thr Phe Pro Gln Gln Pro Tyr Pro
    50                  55                  60

Gln Pro Gln Pro Phe Pro Thr Gln Gln Pro Tyr Pro Gln Pro Gln Pro
65                  70                  75                  80

Phe Pro Gln Pro Gln Pro Phe Pro Pro Gln Leu Pro Tyr Pro Gln Pro
                85                  90                  95

Gln Pro Phe Pro Pro Gln Gln Pro Tyr Pro Gln Pro Gln Thr Gln His
            100                 105                 110

Leu Gln Pro Gln Gln Pro Ile Ser Gln Gln Ala Gln Gln Gln
        115                 120                 125

Gln Gln Gln Gln Gln Gln Gln Gln Gln Gln Gln Leu Gln Gln
    130                 135                 140

Gln Ile Leu Gln Gln Ile Leu Gln Gln Tyr Pro Leu Gly Gln Gly Ser
145                 150                 155                 160

Phe Arg Pro Ser Gln Gln Asn Pro Gln Ala Gln Gly Ser Val Gln Pro
                165                 170                 175

Gln Gln Gln Pro Gln Phe Glu Glu Ile Arg Asn Leu Ala Leu Gln Thr
            180                 185                 190

Leu Pro Ala Met Cys Asn Ala Tyr Ile Pro Pro Tyr Cys Thr Ile Ala
        195                 200                 205

Pro Phe Gly Ile Phe Gly Thr Asn
    210                 215

<210> SEQ ID NO 34
<211> LENGTH: 286
<212> TYPE: PRT
<213> ORGANISM: Hordeum vulgare
<220> FEATURE:
<221> NAME/KEY: misc_feature
<222> LOCATION: (4)..(6)
<223> OTHER INFORMATION: Xaa can be any naturally occurring amino acid

<400> SEQUENCE: 34

Thr Thr Met Xaa Xaa Xaa Pro Ser Gly Leu Glu Leu Glu Arg Pro Gln
1               5                   10                  15

Gln Leu Phe Pro Gln Trp Gln Pro Leu Pro Gln Gln Pro Pro Phe Leu
            20                  25                  30

Gln Gln Glu Pro Glu Gln Pro Tyr Pro Gln Gln Pro Leu Pro Gln
        35                  40                  45

Gln Gln Pro Phe Pro Gln Gln Pro Gln Leu Pro His Gln His Gln Phe
    50                  55                  60

Pro Gln Gln Leu Pro Gln Gln Phe Pro Gln Gln Met Pro Leu Gln
65                  70                  75                  80

Pro Gln Gln Gln Phe Pro Gln Gln Met Pro Leu Gln Pro Gln Gln
                85                  90                  95

Pro Gln Phe Pro Gln Gln Lys Pro Phe Gly Gln Tyr Gln Gln Pro Leu
            100                 105                 110

Thr Gln Gln Pro Tyr Pro Gln Gln Pro Leu Ala Gln Gln Pro
        115                 120                 125
```

```
Ser Ile Glu Glu Gln His Gln Leu Asn Leu Cys Lys Glu Phe Leu Leu
    130                 135                 140

Gln Gln Cys Thr Leu Asp Glu Lys Val Pro Leu Leu Gln Ser Val Ile
145                 150                 155                 160

Ser Phe Leu Arg Pro His Ile Ser Gln Gln Asn Ser Cys Gln Leu Lys
                165                 170                 175

Arg Gln Gln Cys Cys Gln Gln Leu Ala Asn Ile Asn Glu Gln Ser Arg
            180                 185                 190

Cys Pro Ala Ile Gln Thr Ile Val His Ala Ile Val Met Gln Gln Gln
        195                 200                 205

Val Gln Gln Gln Val Gly His Gly Phe Val Gln Ser Gln Leu Gln Gln
210                 215                 220

Leu Gly Gln Gly Met Pro Ile Gln Leu Gln Gln Gln Pro Gly Gln Ala
225                 230                 235                 240

Phe Val Leu Pro Gln Gln Gln Ala Gln Phe Lys Val Val Gly Ser Leu
                245                 250                 255

Val Ile Gln Thr Leu Pro Met Leu Cys Asn Val His Val Pro Pro Tyr
            260                 265                 270

Cys Ser Pro Phe Gly Ser Met Ala Thr Gly Ser Gly Gly Gln
        275                 280                 285

<210> SEQ ID NO 35
<211> LENGTH: 571
<212> TYPE: PRT
<213> ORGANISM: Hordeum vulgare subsp. vulgare

<400> SEQUENCE: 35

Met Ala Ala Thr Ser Phe Val Ser Leu Ser Phe Tyr Phe Cys Ile Phe
1               5                   10                  15

Leu Leu Cys His Gly Ser Met Ala Gln Leu Phe Gly Met Ser Ser Asn
            20                  25                  30

Pro Trp Gln Ser Cys Arg Gln Gly Phe Arg Glu Cys Thr Phe Asn
        35                  40                  45

Arg Leu Gln Ala Ser Thr Pro Leu Arg Gln Val Arg Ser His Ala Gly
    50                  55                  60

Leu Thr Glu Tyr Phe Asp Asp Gln Asn Glu Gln Phe Arg Cys Ile Gly
65                  70                  75                  80

Val Ser Val Ile Arg Arg Val Ile Glu Pro Arg Gly Tyr Leu Leu Pro
                85                  90                  95

Arg Tyr His Asn Thr His Gly Leu Val Tyr Ile Ile Gln Gly Ser Gly
                100                 105                 110

Phe Thr Gly Leu Ser Phe Pro Gly Cys Pro Ala Thr Phe Gln Lys Gln
            115                 120                 125

Phe Gln Lys Tyr Gly Gln Ala Gln Ser Val Gly Gln Ser Gln Ser
        130                 135                 140

Gln Lys Phe Lys Asp Glu His Gln Lys Val Gln His Val Arg Gln Gly
145                 150                 155                 160

Asp Val Ile Ala Leu Pro Ala Gly Ile Thr His Trp Leu Tyr Asn Asp
                165                 170                 175

Gly Asp Ala Pro Ile Val Ala Ile Tyr Val Phe Asp Val Asn Asn Asn
            180                 185                 190

Ala Asn Gln Leu Glu Pro Arg His Lys Glu Phe Leu Leu Ala Gly Asn
        195                 200                 205

Tyr Arg Ser Ser Gln Leu His Ser Ser Gln Asn Ile Phe Ser Gly Phe
    210                 215                 220
```

```
Asp Val Arg Leu Leu Arg Glu Ser Leu Gly Ile Ser Gly Lys Ile Ala
225                 230                 235                 240

Gln Arg Leu Gln Ser Lys Asp Asp Glu Ile Gly Asp Ile Ile His Val
            245                 250                 255

Asn His Thr Leu Lys Phe Leu Lys Pro Ile Phe Thr Gln Gln Gln Glu
        260                 265                 270

Gln Glu Ser Cys Pro Tyr Thr Glu Tyr Glu Glu Gly Gln Ser Gln Ala
    275                 280                 285

Arg His Pro Gln Glu Glu Gln Pro Gln Met Gly Gln Pro Gln Ala Lys
        290                 295                 300

His Tyr His Gly Glu Gln Pro Gln Thr Gly Gln Ser Gln Ala Lys His
305                 310                 315                 320

Ser Gln Gly Glu Gln Thr Gln Thr Gly Gln Ser Gln Ala Lys His Leu
            325                 330                 335

His Gly Gly Gln Pro Glu Glu Gly Arg Gly Gly Gln Ser Gln Glu Glu
        340                 345                 350

Gln Ser Glu Ala Gly Pro Tyr Pro Gly Cys Arg Pro His Ala Gly Gln
    355                 360                 365

Ser His Ala Ser Glu Ser Thr Tyr Gly Gly Trp Asn Gly Leu Glu Glu
370                 375                 380

Asn Phe Cys Asp His Lys Leu Thr Ala Asn Ile Asp Asp Pro Ser Arg
385                 390                 395                 400

Ala Glu Ile Tyr Asn Pro Arg Ala Gly Thr Ile Thr His Leu Asn Ser
            405                 410                 415

Gln Thr Phe Pro Ile Leu Asn Ile Val Gln Met Ser Ala Thr Arg Val
        420                 425                 430

His Leu Tyr Gln Asn Ala Ile Ile Ser Pro Leu Trp Asn Ile Asn Ala
    435                 440                 445

His Ser Val Met Tyr Met Ile Gln Gly His Ile Leu Val Gln Val Val
450                 455                 460

Asn Asp His Gly Arg Asn Val Phe Asn Gly Leu Leu Ser Pro Gly Gln
465                 470                 475                 480

Leu Leu Ile Ile Pro Gln Asn Tyr Val Val Leu Lys Lys Ala Gln Arg
            485                 490                 495

Asp Gly Ser Lys Tyr Ile Glu Phe Lys Thr Asn Ala Asn Ser Met Val
        500                 505                 510

Ser His Ile Ala Gly Lys Asn Ser Ile Leu Gly Ala Leu Pro Val Asp
    515                 520                 525

Val Ile Ala Ser Ala Tyr Asp Ile Ser Arg Thr Glu Ala Arg Ser Leu
530                 535                 540

Lys Phe Asn Arg Glu Glu Leu Gly Val Phe Ala Pro Lys Phe Ser
545                 550                 555                 560

Leu Ser Phe Pro Lys Gly Glu Glu Ser Ser
            565                 570

<210> SEQ ID NO 36
<211> LENGTH: 224
<212> TYPE: PRT
<213> ORGANISM: Hordeum vulgare

<400> SEQUENCE: 36

Met Gly Lys Phe Ile Phe Phe Ala Val Phe Leu Thr Thr Leu Val Thr
1               5                   10                  15

Ile Ser Ala Ala Gln Gly Val Leu Glu Gln Ser Leu Ala Asp Ala Gln
```

|                20                    25                    30              |
|----|

Cys Arg Gly Glu Val Gln Ala Lys Pro Leu Leu Ala Cys Arg Gln Ile
                 35                    40                    45

Leu Glu His Gln Leu Thr Gly Arg Ala Val Gly Val Arg Pro Phe Gln
 50                    55                    60

Ala Gln Trp Gly Ala Arg Asp Arg Cys Cys Gln Leu Glu Ser Val
 65                    70                    75                    80

Ser Arg Gly Cys Arg Cys Ser Ala Leu Arg Gly Met Val Arg Asp Tyr
                       85                    90                    95

Glu Gln Ser Met Pro Pro Leu Arg Glu Gly Arg Arg Ser Ser Gly
                 100                   105                   110

Glu Arg Gln Gln Glu Gln Gly Cys Ser Gly Glu Ser Thr Ala Glu Gln
                 115                   120                   125

Gln Gln Glu Val Gln Gly Gly Gln Tyr Gly Ser Glu Thr Gly Glu Ser
                 130                   135                   140

Gln Gln Gln Gln Gly Gly Tyr His Gly Val Thr Val Gly Arg Gly
 145                   150                   155                   160

Gly Gln Gln Gln Gly Gln Met Leu Cys Arg Glu Arg Pro Gln Arg Gln
                       165                   170                   175

Gln Gln Gly Glu Gly Phe Ser Gly Glu Gly Ala Gln Gln Lys Pro Lys
                 180                   185                   190

Val Gly Arg Val Arg Leu Thr Lys Val Arg Leu Pro Thr Ala Cys Arg
                 195                   200                   205

Ile Glu Pro Gln Glu Cys Ser Val Phe Ser Thr Leu Pro Val Leu Gly
                 210                   215                   220

<210> SEQ ID NO 37
<211> LENGTH: 637
<212> TYPE: PRT
<213> ORGANISM: Hordeum vulgare subsp. vulgare

<400> SEQUENCE: 37

Met Ala Thr Arg Ala Lys Ala Thr Ile Pro Leu Leu Phe Leu Leu Gly
 1                 5                    10                    15

Thr Ser Leu Leu Phe Ala Ala Ala Val Ser Ala Ser His Asp Asp Glu
                 20                    25                    30

Asp Asp Arg Arg Gly Gly His Ser Leu Gln Gln Cys Val Gln Arg Cys
                 35                    40                    45

Arg Gln Glu Arg Pro Arg Tyr Ser His Ala Arg Cys Val Gln Glu Cys
 50                    55                    60

Arg Asp Asp Gln Gln Gln His Gly Arg His Glu Gln Glu Glu Glu Gln
 65                    70                    75                    80

Gly Arg Gly Arg Gly Trp His Gly Glu Gly Glu Arg Glu Glu His
                       85                    90                    95

Gly Arg Gly Arg Gly Arg His Gly Glu Gly Glu Arg Glu Glu His
                 100                   105                   110

Gly Arg Gly Arg Gly Arg His Gly Glu Gly Glu Arg Glu Glu Arg
                 115                   120                   125

Gly Arg Gly His Gly Arg His Gly Glu Gly Glu Arg Glu Glu Arg
                 130                   135                   140

Gly Arg Gly Arg Gly Arg His Gly Glu Gly Glu Arg Glu Glu Glu
 145                   150                   155                   160

Gly Arg Gly Arg Gly Arg Arg Gly Glu Gly Glu Arg Asp Glu Glu Gln
                       165                   170                   175

-continued

```
Gly Asp Ser Arg Arg Pro Tyr Val Phe Gly Pro Arg Ser Phe Arg Arg
            180                 185                 190

Ile Ile Gln Ser Asp His Gly Phe Val Arg Ala Leu Arg Pro Phe Asp
        195                 200                 205

Gln Val Ser Arg Leu Leu Arg Gly Ile Arg Asp Tyr Arg Val Ala Ile
    210                 215                 220

Met Glu Val Asn Pro Arg Ala Phe Val Pro Gly Phe Thr Asp Ala
225                 230                 235                 240

Asp Gly Val Gly Tyr Val Ala Gln Gly Glu Gly Val Leu Thr Val Ile
                245                 250                 255

Glu Asn Gly Glu Lys Arg Ser Tyr Thr Val Lys Glu Gly Asp Val Ile
            260                 265                 270

Val Ala Pro Ala Gly Ser Ile Met His Leu Ala Asn Thr Asp Gly Arg
        275                 280                 285

Arg Lys Leu Val Ile Ala Lys Ile Leu His Thr Ile Ser Val Pro Gly
    290                 295                 300

Lys Phe Gln Phe Leu Ser Val Lys Pro Leu Leu Ala Ser Leu Ser Lys
305                 310                 315                 320

Arg Val Leu Arg Ala Ala Phe Lys Thr Ser Asp Glu Arg Leu Glu Arg
                325                 330                 335

Leu Phe Asn Gln Arg Gln Gly Gln Glu Lys Thr Arg Ser Val Ser Ile
            340                 345                 350

Val Arg Ala Ser Glu Glu Gln Leu Arg Glu Leu Arg Glu Ala Ala
        355                 360                 365

Glu Gly Gly Gln Gly His Arg Trp Pro Leu Pro Pro Phe Arg Gly Asp
370                 375                 380

Ser Arg Asp Thr Phe Asn Leu Leu Glu Gln Arg Pro Lys Ile Ala Asn
385                 390                 395                 400

Arg His Gly Arg Leu Tyr Glu Ala Asp Ala Arg Ser Phe His Ala Leu
                405                 410                 415

Ala Asn Gln Asp Val Arg Val Ala Val Ala Asn Ile Thr Pro Gly Ser
            420                 425                 430

Met Thr Ala Pro Tyr Leu Asn Thr Gln Ser Phe Lys Leu Ala Val Val
        435                 440                 445

Leu Glu Gly Glu Gly Glu Val Gln Ile Val Cys Pro His Leu Gly Arg
    450                 455                 460

Glu Ser Glu Ser Glu Arg His Gly Lys Gly Arg Arg Glu Glu
465                 470                 475                 480

Glu Glu Asp Asp Gln Arg Gln Gln Arg Arg Gly Ser Glu Ser Glu
                485                 490                 495

Ser Glu Glu Glu Glu Gln Gln Arg Tyr Glu Thr Val Arg Ala Arg
            500                 505                 510

Val Ser Arg Gly Ser Ala Phe Val Pro Pro Gly His Pro Val Val
        515                 520                 525

Glu Ile Ser Ser Ser Gln Gly Ser Ser Asn Leu Gln Val Val Cys Phe
    530                 535                 540

Glu Ile Asn Ala Glu Arg Asn Glu Arg Val Trp Leu Ala Gly Arg Asn
545                 550                 555                 560

Asn Val Ile Gly Lys Leu Gly Ser Pro Ala Gln Glu Leu Thr Phe Gly
                565                 570                 575

Arg Pro Ala Arg Glu Val Gln Glu Val Phe Arg Ala Gln Asp Gln Asp
            580                 585                 590

Glu Gly Phe Val Ala Gly Pro Glu Gln Gln Ser Arg Glu Gln Glu Gln
```

```
                595                 600                 605
Glu Gln Glu Arg His Arg Arg Gly Asp Arg Gly Arg Gly Asp Glu
    610                 615                 620
Ala Val Glu Thr Phe Leu Arg Met Ala Thr Gly Ala Ile
625                 630                 635

<210> SEQ ID NO 38
<211> LENGTH: 500
<212> TYPE: PRT
<213> ORGANISM: Oryza sativa Japonica Group

<400> SEQUENCE: 38

Met Ala Thr Ile Ala Phe Ser Arg Leu Ser Ile Tyr Phe Cys Val Leu
1               5                   10                  15

Leu Leu Cys His Gly Ser Met Ala Gln Leu Phe Gly Pro Asn Val Asn
                20                  25                  30

Pro Trp His Asn Pro Arg Gln Gly Gly Phe Arg Glu Cys Arg Phe Asp
            35                  40                  45

Arg Leu Gln Ala Phe Glu Pro Leu Arg Arg Val Arg Ser Glu Ala Gly
        50                  55                  60

Val Thr Glu Tyr Phe Asp Glu Lys Asn Glu Gln Phe Gln Cys Thr Gly
65                  70                  75                  80

Thr Phe Val Ile Arg Arg Val Ile Glu Pro Gln Gly Leu Leu Val Pro
                85                  90                  95

Arg Tyr Ser Asn Thr Pro Gly Met Val Tyr Ile Ile Gln Gly Arg Gly
            100                 105                 110

Ser Met Gly Leu Thr Phe Pro Gly Cys Pro Ala Thr Tyr Gln Gln Gln
        115                 120                 125

Phe Gln Gln Phe Leu Pro Glu Gly Gln Ser Gln Ser Gln Lys Phe Arg
130                 135                 140

Asp Glu His Gln Lys Ile His Gln Phe Arg Gln Gly Asp Ile Val Ala
145                 150                 155                 160

Leu Pro Ala Gly Val Ala His Trp Phe Tyr Asn Glu Gly Asp Ala Pro
                165                 170                 175

Val Val Ala Leu Tyr Val Phe Asp Leu Asn Asn Asn Ala Asn Gln Leu
            180                 185                 190

Glu Pro Arg Gln Lys Glu Phe Leu Leu Ala Gly Asn Asn Asn Arg Glu
        195                 200                 205

Gln Gln Met Tyr Gly Arg Ser Ile Glu Gln His Ser Gly Gln Asn Ile
210                 215                 220

Phe Ser Gly Phe Asn Asn Glu Leu Leu Ser Glu Ala Leu Gly Val Asn
225                 230                 235                 240

Ala Leu Val Ala Lys Arg Leu Gln Gly Gln Asn Asp Gln Arg Gly Glu
                245                 250                 255

Ile Ile Arg Val Lys Asn Gly Leu Lys Leu Leu Arg Pro Ala Phe Ala
            260                 265                 270

Gln Gln Gln Glu Gln Ala Gln Gln Glu Gln Ala Gln Ala Gln Tyr
        275                 280                 285

Gln Val Gln Tyr Ser Glu Glu Gln Gln Pro Ser Thr Arg Cys Asn Gly
290                 295                 300

Leu Asp Glu Asn Phe Cys Thr Ile Lys Ala Arg Leu Asn Ile Glu Asn
305                 310                 315                 320

Pro Ser His Ala Asp Thr Tyr Asn Pro Arg Ala Gly Arg Ile Thr Arg
                325                 330                 335
```

```
Leu Asn Ser Gln Lys Phe Pro Ile Leu Asn Leu Val Gln Leu Ser Ala
            340                 345                 350

Thr Arg Val Asn Leu Tyr Gln Asn Ala Ile Leu Ser Pro Phe Trp Asn
        355                 360                 365

Val Asn Ala His Ser Leu Val Tyr Ile Val Gln Gly His Ala Arg Val
    370                 375                 380

Gln Val Val Ser Asn Leu Gly Lys Thr Val Phe Asn Gly Val Leu Arg
385                 390                 395                 400

Pro Gly Gln Leu Leu Ile Ile Pro Gln His Tyr Val Val Leu Lys Lys
                405                 410                 415

Ala Glu His Glu Gly Cys Gln Tyr Ile Ser Phe Lys Thr Asn Ala Asn
            420                 425                 430

Ser Met Val Ser His Leu Ala Gly Lys Asn Ser Ile Phe Arg Ala Met
        435                 440                 445

Pro Val Asp Val Ile Ala Asn Ala Tyr Arg Ile Ser Arg Glu Gln Ala
    450                 455                 460

Arg Ser Leu Lys Asn Asn Arg Gly Glu Leu Gly Ala Phe Thr Pro
465                 470                 475                 480

Arg Tyr Gln Gln Gln Thr Tyr Pro Gly Phe Ser Asn Glu Ser Glu Asn
                485                 490                 495

Glu Ala Leu Glu
            500

<210> SEQ ID NO 39
<211> LENGTH: 468
<212> TYPE: PRT
<213> ORGANISM: Oryza sativa Indica Group

<400> SEQUENCE: 39

Cys Leu Cys Ala Leu Leu Ala Pro Leu Phe Ser Gln Gly Val Asp
1               5                   10                  15

Ala Trp Glu Ser Arg Gln Gly Ala Ser Arg Glu Cys Arg Phe Asp Arg
            20                  25                  30

Leu Gln Ala Phe Glu Pro Leu Arg Lys Ala Arg Ser Glu Ala Gly Val
        35                  40                  45

Thr Glu Tyr Phe Asp Glu Arg Asn Glu Gln Phe Arg Cys Ala Gly Val
    50                  55                  60

Phe Val Ile Arg Arg Val Ile Glu Pro Gln Gly Pro Val Val Pro Arg
65                  70                  75                  80

Tyr Ser Asn Thr Pro Ala Leu Ala Tyr Ile Ile Gln Gly Lys Gly Tyr
                85                  90                  95

Val Gly Leu Thr Phe Pro Gly Cys Pro Ala Thr His Gln Gln Gln Phe
            100                 105                 110

Gln Leu Phe Glu Gln Arg Gln Ser Asp Gln Ala His Lys Phe Arg Asp
        115                 120                 125

Glu His Gln Lys Ile His Glu Phe Arg Gln Gly Asp Val Val Ala Leu
    130                 135                 140

Pro Ala Ser Val Ala His Trp Phe Tyr Asn Gly Gly Asp Thr Pro Ala
145                 150                 155                 160

Ile Val Val Tyr Val Tyr Asp Ile Lys Ser Phe Ala Asn Gln Leu Glu
                165                 170                 175

Pro Arg Gln Lys Glu Phe Leu Leu Ala Gly Asn Asn Gln Arg Gly Gln
            180                 185                 190

Gln Ile Phe Glu His Ser Ile Phe Gln His Ser Gly Gln Asn Ile Phe
        195                 200                 205
```

```
Ser Gly Phe Asn Thr Glu Val Leu Ser Glu Ala Leu Gly Ile Asn Thr
        210                 215                 220

Glu Ala Ala Lys Arg Leu Gln Ser Gln Asn Asp Gln Arg Gly Asp Ile
225                 230                 235                 240

Ile Arg Val Lys His Gly Leu Gln Leu Lys Pro Thr Leu Thr Gln
                245                 250                 255

Arg Gln Glu Glu Pro Arg Gln Tyr Gln Gln Val Gln Tyr Arg Glu Gly
            260                 265                 270

Gln Tyr Asn Gly Leu Asp Glu Asn Phe Cys Thr Ile Lys Ala Arg Val
        275                 280                 285

Asn Ile Glu Asn Pro Asn Arg Ala Asp Tyr Tyr Asn Pro Arg Ala Gly
    290                 295                 300

Arg Ile Thr Leu Leu Asn Asn Gln Lys Phe Pro Ile Leu Asn Leu Ile
305                 310                 315                 320

Gly Met Gly Ala Thr Arg Val Asn Leu Tyr Gln Asn Ala Leu Leu Ser
                325                 330                 335

Pro Phe Trp Asn Ile Asn Ala His Ser Val Val Tyr Ile Ile Gln Gly
            340                 345                 350

Ser Ala Gln Val Gln Val Ala Asn Asn Gln Gly Arg Thr Val Phe Ser
        355                 360                 365

Gly Val Leu His Gln Gly Gln Leu Leu Ile Ile Pro Gln Asn His Ala
    370                 375                 380

Val Ile Lys Lys Ala Glu His Asn Gly Cys Gln Tyr Val Ala Ile Lys
385                 390                 395                 400

Thr Ile Pro Asn Pro Met Val Ser Arg Val Ala Gly Lys Asn Ser Ile
                405                 410                 415

Leu Arg Ala Leu Pro Val Asp Val Ile Ala Asn Ala Tyr Arg Ile Ser
            420                 425                 430

Arg Asp Glu Ala Arg Arg Leu Lys Asn Asn Arg Ala Asp Glu Ile Gly
        435                 440                 445

Ala Phe Thr Pro Arg Phe Pro Gln Lys Ser Gln Arg Gly Tyr Gln Phe
    450                 455                 460

Leu Thr Glu Gly
465

<210> SEQ ID NO 40
<211> LENGTH: 219
<212> TYPE: PRT
<213> ORGANISM: Ipomoea batatas

<400> SEQUENCE: 40

Met Lys Ala Phe Thr Leu Ala Leu Phe Leu Ala Leu Ser Leu Tyr Leu
1               5                   10                  15

Leu Pro Asn Pro Ala His Ser Arg Phe Asn Pro Ile Arg Leu Pro Thr
            20                  25                  30

Thr His Glu Pro Ala Ser Ser Glu Thr Pro Val Leu Asp Ile Asn Gly
        35                  40                  45

Asp Glu Val Arg Ala Gly Gly Asn Tyr Tyr Met Val Ser Ala Ile Trp
    50                  55                  60

Gly Ala Gly Gly Gly Leu Arg Leu Ala His Leu Asp Met Met Ser
65                  70                  75                  80

Lys Cys Ala Ser Asp Val Ile Val Ser Pro Asn Asp Leu Asp Asn Gly
                85                  90                  95

Asp Pro Ile Thr Ile Thr Pro Ala Thr Ala Asp Pro Glu Ser Thr Val
```

```
                          100                 105                 110
Val Met Ala Ser Thr Tyr Gln Thr Phe Arg Phe Asn Ile Ala Thr Asn
            115                 120                 125

Lys Leu Cys Val Asn Asn Val Asn Trp Gly Ile Gln His Asp Ser Ala
130                 135                 140

Ser Gly Gln Tyr Phe Leu Lys Ala Gly Glu Phe Val Ser Asp Asn Ser
145                 150                 155                 160

Asn Gln Phe Lys Ile Glu Val Val Asp Ala Asn Leu Asn Phe Tyr Lys
                165                 170                 175

Leu Thr Tyr Cys Gln Phe Gly Ser Asp Lys Cys Tyr Asn Val Gly Arg
            180                 185                 190

Phe His Asp Pro Met Leu Arg Thr Thr Arg Leu Ala Leu Ser Asn Ser
        195                 200                 205

Pro Phe Val Phe Val Ile Lys Pro Thr Asp Val
    210                 215

<210> SEQ ID NO 41
<211> LENGTH: 171
<212> TYPE: PRT
<213> ORGANISM: Ipomoea batatas

<400> SEQUENCE: 41

Arg Arg Gly Pro Arg Arg Glu Leu Leu His Gly Leu Arg His Met
1               5                   10                  15

Gly Ser Arg Arg Gly Arg Ala Lys Thr Arg Pro Leu Gly His Asp Val
            20                  25                  30

Gln Met Arg Gln Arg Arg His Arg Ile Pro Gln Arg Leu Arg Gln Arg
        35                  40                  45

Arg Pro His His His His Ala Gly Asp Gly Arg Pro Glu Ser Thr Val
    50                  55                  60

Val Met Ala Ser Thr Tyr Gln Thr Phe Arg Phe Asn Ile Ala Thr Asn
65                  70                  75                  80

Lys Leu Cys Val Asn Asn Val Asn Trp Gly Ile Gln Tyr Asp Ser Ala
                85                  90                  95

Ser Val Gln Ser Leu Leu Lys Ala Gly Glu Phe Val Ser Asp Asn Ser
            100                 105                 110

Asn Gln Phe Lys Ile Glu Val Val Asp Ala Asn Leu Asn Phe Tyr Lys
        115                 120                 125

Leu Thr Tyr Cys Leu Phe Gly Ser Asp Lys Cys Tyr Asn Val Gly Arg
    130                 135                 140

Phe Lys Asp Pro Met Leu Arg Thr Thr Arg Leu Ala Leu Ser Ser Tyr
145                 150                 155                 160

Pro Phe Phe Phe Val Ile Lys Pro Thr Val Val
                165                 170

<210> SEQ ID NO 42
<211> LENGTH: 154
<212> TYPE: PRT
<213> ORGANISM: Ipomoea batatas

<400> SEQUENCE: 42

Met Ala Leu Gln Leu Ala Ala His Ser Asp Ala Arg Ser Gly Pro Val
1               5                   10                  15

Gly Ser Asn Gly Gly Gln Phe Trp Ser Phe Arg Pro Val Arg Pro Leu
            20                  25                  30

Asn Lys Ile Val Leu Ser Phe Ser Gly Ser Pro Asp Gln Thr Leu Asn
```

```
                35                  40                  45
Leu Ile Ser Ile Thr Phe Ser Ser Asn Pro Thr Asp Ile Ile Thr Val
 50                  55                  60

Gly Gly Val Gly Pro Glu Pro Leu Thr Tyr Thr Glu Thr Val Asn Ile
65                  70                  75                  80

Asp Gly Asp Ile Ile Glu Ile Ser Gly Met Ile Ala Asn Tyr Lys Gly
                85                  90                  95

Tyr Asn Val Ile Arg Ser Ile Lys Phe Thr Thr Asn Lys Lys Glu Tyr
            100                 105                 110

Gly Pro Tyr Gly Ala Asn Ala Gly Thr Pro Phe Asn Ile Lys Ile Pro
        115                 120                 125

Asp Gly Asn Lys Ile Val Gly Phe Phe Gly Asn Ser Gly Trp Tyr Val
130                 135                 140

Asp Ala Ile Gly Ala Tyr Tyr Thr Ala Lys
145                 150
```

<210> SEQ ID NO 43
<211> LENGTH: 451
<212> TYPE: PRT
<213> ORGANISM: Solanum tuberosum

<400> SEQUENCE: 43

```
Met Ala Val Ser Asp Ser Gln Asn Ser Gln Thr Cys Leu Asp Pro Asp
1               5                   10                  15

Ala Ser Arg Ser Val Leu Gly Ile Ile Leu Gly Gly Ala Gly Thr
            20                  25                  30

Arg Leu Tyr Pro Leu Thr Lys Lys Arg Ala Lys Pro Ala Val Pro Leu
        35                  40                  45

Gly Ala Asn Tyr Arg Leu Ile Asp Ile Pro Val Ser Asn Cys Leu Asn
    50                  55                  60

Ser Asn Ile Ser Lys Ile Tyr Val Leu Thr Gln Phe Asn Ser Ala Ser
65                  70                  75                  80

Leu Asn Arg His Leu Ser Arg Ala Tyr Ala Ser Asn Met Gly Gly Tyr
                85                  90                  95

Lys Asn Glu Gly Phe Val Glu Val Leu Ala Ala Gln Gln Ser Pro Glu
            100                 105                 110

Asn Pro Asp Trp Phe Gln Gly Thr Ala Asp Ala Val Arg Gln Tyr Leu
        115                 120                 125

Trp Leu Phe Glu Glu His Thr Val Leu Glu Tyr Leu Ile Leu Ala Gly
130                 135                 140

Asp His Leu Tyr Arg Met Asp Tyr Glu Lys Phe Ile Gln Ala His Arg
145                 150                 155                 160

Glu Thr Asp Ala Asp Ile Thr Val Ala Ala Leu Pro Met Asp Glu Lys
                165                 170                 175

Arg Ala Thr Ala Phe Gly Leu Met Lys Ile Asp Glu Glu Gly Arg Ile
            180                 185                 190

Ile Glu Phe Ala Glu Lys Pro Gln Gly Glu Gln Leu Gln Ala Met Lys
        195                 200                 205

Val Asp Thr Thr Ile Leu Gly Leu Asp Asp Lys Arg Ala Lys Glu Met
210                 215                 220

Pro Phe Ile Ala Ser Met Gly Ile Tyr Val Ile Ser Lys Asp Val Met
225                 230                 235                 240

Leu Asn Leu Leu Arg Asp Lys Phe Pro Gly Ala Asn Asp Phe Gly Ser
                245                 250                 255
```

-continued

Glu Val Ile Pro Gly Ala Thr Ser Leu Gly Met Arg Val Gln Ala Tyr
            260                 265                 270

Leu Tyr Asp Gly Tyr Trp Glu Asp Ile Gly Thr Ile Glu Ala Phe Tyr
        275                 280                 285

Asn Ala Asn Leu Gly Ile Thr Lys Lys Pro Val Pro Asp Phe Ser Phe
    290                 295                 300

Tyr Asp Arg Ser Ala Pro Ile Tyr Thr Gln Pro Arg Tyr Leu Pro Pro
305                 310                 315                 320

Ser Lys Met Leu Asp Ala Asp Val Thr Asp Ser Val Ile Gly Glu Gly
                325                 330                 335

Cys Val Ile Lys Asn Cys Lys Ile His His Ser Val Val Gly Leu Arg
            340                 345                 350

Ser Cys Ile Ser Glu Gly Ala Ile Ile Glu Asp Ser Leu Leu Met Gly
        355                 360                 365

Ala Asp Tyr Tyr Glu Thr Asp Ala Asp Arg Lys Leu Leu Ala Ala Lys
    370                 375                 380

Gly Ser Val Pro Ile Gly Ile Gly Lys Asn Cys His Ile Lys Arg Ala
385                 390                 395                 400

Ile Ile Asp Lys Asn Ala Arg Ile Gly Asp Asn Val Lys Ile Ile Asn
                405                 410                 415

Lys Asp Asn Val Gln Glu Ala Ala Arg Glu Thr Asp Gly Tyr Phe Ile
            420                 425                 430

Lys Ser Gly Ile Val Thr Val Ile Lys Asp Ala Leu Ile Pro Ser Gly
        435                 440                 445

Ile Ile Ile
    450

<210> SEQ ID NO 44
<211> LENGTH: 543
<212> TYPE: PRT
<213> ORGANISM: Solanum tuberosum

<400> SEQUENCE: 44

Met Lys Ser Ser Pro Thr His Phe Phe Phe Lys His Asn Ser Met Leu
1               5                   10                  15

Leu Arg Leu Leu Ile Phe Ile Leu Gly Ile Cys Ser Ile Asn Arg Ser
            20                  25                  30

Asn Leu Cys Cys Asp Gln Leu Phe Ala Asn Pro Ser Ser Phe Ser Val
        35                  40                  45

Ile Gln Ser Ser Leu Lys Gln Leu Lys Ile Glu Gly Tyr Phe Ser Phe
    50                  55                  60

Lys Asn Phe Asp His Val Ala Lys Asp Phe Gly Asn Arg Tyr His Phe
65                  70                  75                  80

Leu Pro Ser Ala Val Leu Tyr Pro Lys Ser Val Ser Asp Ile Ser Ser
                85                  90                  95

Thr Leu Lys His Ile Phe Asp Met Gly Thr Thr Thr Asp Leu Thr Val
            100                 105                 110

Ala Ala Arg Gly His Gly His Ser Leu Glu Gly Gln Ala Gln Ala Tyr
        115                 120                 125

Arg Gly Val Val Ile Ser Met Glu Ser Leu Arg Ala Pro Ala Met Arg
    130                 135                 140

Phe His His Ala Gly Glu Leu Pro Phe Ile Asp Val Ser Ala Gly Glu
145                 150                 155                 160

Leu Trp Ile Asn Ile Leu His Glu Ser Leu Lys Leu Gly Leu Thr Pro
                165                 170                 175

Lys Ser Trp Thr Asp Tyr Leu His Leu Thr Val Gly Gly Thr Leu Ser
            180                 185                 190

Asn Ala Gly Ile Ser Gly Gln Ala Phe Lys His Gly Pro Gln Ile Asn
            195                 200                 205

Asn Val Tyr Gln Leu Glu Val Val Thr Gly Lys Gly Glu Val Ile Thr
210                 215                 220

Cys Ser Lys Glu Gln Asn Ala Asp Leu Phe Tyr Gly Val Leu Gly Gly
225                 230                 235                 240

Leu Gly Gln Leu Gly Ile Ile Thr Arg Ala Arg Ile Ala Leu Gln Pro
                245                 250                 255

Ala Pro Lys Lys Val Lys Trp Ile Arg Val Leu Tyr Ser Asp Phe Ser
            260                 265                 270

Thr Phe Ser Asn Asp Gln Glu Gln Leu Ile Ser Ser Lys Asp Ser Phe
            275                 280                 285

Asp Tyr Val Glu Gly Phe Val Ile Asn Arg Thr Gly Leu Leu Asn
            290                 295                 300

Asn Trp Arg Ser Thr Phe Asn Pro Lys Asp Pro Leu Leu Ala Arg Lys
305                 310                 315                 320

Phe Ser Glu Gly Lys Val Leu Tyr Cys Leu Glu Val Ala Lys Tyr
                325                 330                 335

Phe Asn Pro Glu Asp Thr Pro Asn Thr Asp Gln Asn Ile Glu Val Leu
            340                 345                 350

Leu Ser Lys Leu Asn Tyr Ile Glu Ser Thr Leu Phe Gln Ser Glu Val
            355                 360                 365

Ser Tyr Val Glu Phe Leu Asp Arg Val His Val Ser Glu Met Lys Leu
            370                 375                 380

Gln Glu Lys Gly Leu Trp Asp Val Pro His Pro Trp Leu Asn Leu Leu
385                 390                 395                 400

Ile Pro Lys Ser Arg Ile His Asp Phe Ala Gln Glu Val Phe Gly Lys
                405                 410                 415

Ile Leu Thr Asp Thr Ser His Gly Pro Ile Leu Ile Tyr Pro Val Asn
            420                 425                 430

Lys Ser Lys Trp Ile Lys Gly Thr Ser Met Val Thr Pro Glu Glu Asp
            435                 440                 445

Val Met Tyr Leu Ile Ala Phe Leu Ser Ser Ala Met Pro Ser Ser Thr
450                 455                 460

Gly Lys Asp Gly Leu Glu His Ile Leu Asn Lys Asn Lys Lys Ile Leu
465                 470                 475                 480

Asn Phe Cys Asn Lys Ala His Ile Gly Met Lys Gln Tyr Leu Pro His
                485                 490                 495

Tyr Thr Thr Gln Glu Asp Trp Lys Val His Phe Gly Arg Trp Glu
            500                 505                 510

Thr Phe Ala Arg Arg Lys Ser Thr Tyr Asp Pro Leu Ser Ile Leu Ala
            515                 520                 525

Pro Gly His Arg Ile Phe Glu Arg Ala Ser Leu Leu Gln Gln Arg
            530                 535                 540

<210> SEQ ID NO 45
<211> LENGTH: 4
<212> TYPE: PRT
<213> ORGANISM: Artificial Sequence
<220> FEATURE:
<223> OTHER INFORMATION: Synthetic peptide

<400> SEQUENCE: 45

```
Thr Asp Val Glu
1

<210> SEQ ID NO 46
<211> LENGTH: 4
<212> TYPE: PRT
<213> ORGANISM: Artificial Sequence
<220> FEATURE:
<223> OTHER INFORMATION: Synthetic peptide

<400> SEQUENCE: 46

Asn Leu His Leu
1
```

INFLAMMATION-SUPPRESSING COMPOSITION INCLUDING PEPTIDE

CROSS REFERENCE TO RELATED APPLICATIONS

This application is a National Stage of International Application No. PCT/JP2016/065627 filed May 26, 2016, claiming priority based on Japanese Patent Application Nos. 2015-107924 filed May 27, 2015 and 2016-091950 filed Apr. 28, 2016, the contents of all of which are incorporated herein by reference in their entirety.

TECHNICAL FIELD

The present invention relates to a composition for suppressing microglial-mediated inflammation and a use thereof in food and drink products.

BACKGROUND ART

Microglia, the only immune cell found in the brain, account for 10% of the brain and are revealed to have essential functions to maintain the homeostasis in the brain such as phagocytic removal of wastes and repair of damaged tissues in the brain. Microglia contribute to maintain, enhance and improve the cognitive functions by maintaining the homeostasis in the brain. However, it is known that the excessive activation of microglia induces inflammation, and thus reactive oxygen species (ROS) and proinflammatory cytokines such as TNF-α and IL-β are chronically produced, thereby causing stress to neurons.

For example, even in patients with a mood disorder such as depression, chronic inflammation is caused and continuous production enhancement of proinflammatory cytokines and reactive oxygen species is recognized. Patients with a mood disorder have elevated blood CRP and proinflammatory cytokines values, and the correlation between these values and symptoms and treatment resistance is recognized. It is also reported that these marker values are normalized after disappearance of symptoms. Proinflammatory cytokines such as INF-γ and TNF-α and reactive oxygen species themselves have tissue disordering properties to nerve cells, neural stem cells and oligodendrocytes. In the brain of mood disorder patients, histological changes such as synaptic pathological changes, neurogenesis suppression, white matter changes are found and the proinflammatory cytokines and reactive oxygen species produced by microglia may be causing these changes (Non Patent Literature 1).

The reactive oxygen species and proinflammatory cytokines such as TNF-α produced by excessively activated microglia are reported to have been closely associated with pains and pathological conditions of chronic fatigue syndrome in addition to mood disorders including depression (Non Patent Literatures 2 to 7). Considering these findings, it is conceived that the suppression of the excessive microglia activation is useful to treat, relieve and further prevent diseases recognized to have been correlated with the excessive microglia activation such as pains, chronic fatigue syndrome, cognitive impairment and multiple sclerosis in addition to depression.

Some peptides have been disclosed as substances effective in suppressing microglial-mediated inflammation or to protect nerves. Patent Literature 1 discloses a peptide that suppresses microglial-mediated inflammation and protects nerves. A polypeptide including in the sequence the peptide consisting of 5 amino acids having a specific characteristic is disclosed as having actions to suppress the activation of microglia and suppress the inflammation. It is also suggested that the above peptide may be effective to various diseases including acute diseases and chronic diseases considered to have been related to microglial-mediated inflammation. Patent Literature 1 further describes the administration by injection or inhalation as the peptide administration method.

Patent Literature 2 discloses that nerves are continuously protected by intravenously administering tripeptide Gly-Pro-Glu (GPE) by an injection. The tripeptide administration particularly targets diseases accompanied by morphologically notable damages such as acute ischemic damage. In addition, it is not disclosed that the target is microglia.

CITATION LIST

Patent Literature

Patent Literature 1: National Publication of International Patent Application No. 2014-509594
Patent Literature 2: National Publication of International Patent Application No. 2007-509169

Non Patent Literature

Non Patent Literature 1: Monji Akira, 2012, Psychiat. Neurol. Jap., Vol. 114, No. 2, pp. 124-133
Non Patent Literature 2: Berta, T., et al., 2014, J. Clin. Invest., Vol. 124 (3), pp. 1173-1186
Non Patent Literature 3: Riazi, K., et al., 2008, Proc. Natl. Acad. Sci. USA, Vol. 105 (44), pp. 17151-17156
Non Patent Literature 4: Grinberg, Y. Y., et al., 2013, J. Neurochem., Vol. 126 (5), pp. 662-672
Non Patent Literature 5: Couch, Y., et al., 2013, Brain Behav. Immun., Vol. 29, pp. 139-146
Non Patent Literature 6: Yasui, M., et al., 2014, Glia, doi: 10.1002/glia.22687
Non Patent Literature 7: Nakatomi, Y., et al., 2014, J. Nucl. Med., Vol. 55, pp. 945-950

SUMMARY OF INVENTION

Technical Problem

The peptides described in Patent Literatures 1 and 2 are assumed to be administered by an injection to diseases accompanied by neurodegeneration. Thus, it is understood that these peptides were intended to be administered to a patient with a comparatively severe symptom.

An object of the present invention is to provide a composition that is effective to a patient with, needless to say, a severe symptom and also with a comparatively mild symptom and can be continuously taken. Diseases caused by microglial-mediated inflammation include pains, chronic fatigue syndrome, cognitive impairment and multiple sclerosis as described above and also mood disorders as noted in depression. An object of the present invention is to provide a composition effective to, needless to say, patients suffering from these diseases and also groups with high risks of onset.

It is indicated that, for example, a sense of social failure, lack of willingness and motivation, instability of willingness and mental condition also lead to mood disorders such as depression. The issues on "moods" and "emotions" such as lack of willingness and vitality appeared as no motivation or vibrant spirit, lack of self-esteem and inquisitiveness and further a depressed feeling that does not recover and a positive attitude thus failed to be developed are often interpreted as an issue of one's personality. However, the cerebral structural pathological condition that has been present even before depression becomes apparent or during a convalescent stage is considered included.

Further, it is well known that a response to stress varies depending on person to person even when exposed to the same mental stress or physical stress. It is thus indicated that the vulnerability to stress also leads to the onset of mood disorders such as depression.

The inflammation in the brain caused by stress chronically exposed in everyday life is maintained at the normal condition by suppressing the excessive microglial-mediated inflammation. It is considered important that microglial-mediated inflammation be suitably controlled to achieve the so-called "tolerant to stress" normal condition.

An object of the present invention is to provide a composition having as an effective component a peptide effective to various diseases and conditions induced by microglial-mediated inflammation or a pharmaceutically acceptable salt or a solvate thereof. An object of the present invention is to provide a composition or food and drink products that can relieve and suppress the inflammatory condition microglia induce in the brain and ameliorate not only diseases such as chronic fatigue syndrome, cognitive impairment and mood disorders but also a condition detected before these diseases develop. An object of the present invention is to particularly provide a composition or food and drink products capable of ameliorating lack of willingness and motivation which have been dealt as an issue of mood or emotion and conditions that have not been diagnosed as a disease such as a decrease in vitality.

Solution to Problems

The first embodiment of the present invention is to provide a composition for suppressing microglial-mediated inflammation comprising a dipeptide having an amino acid sequence represented by LH, DV or MH, or an oligopeptide including the amino acid sequence as a core sequence, or a pharmaceutically acceptable salt or a solvate thereof.

The dipeptide having an amino acid sequence represented by LH, DV or MH or the oligopeptide including the amino acid sequence as a core sequence acts to suppress microglial-mediated inflammation. Thus, the composition containing these can be expected to be effective in suppressing microglial-mediated inflammation.

The second embodiment of the present invention is to provide a composition for relieving, treating or preventing a symptom of chronic fatigue syndrome, cognitive impairment and/or mood disorder, the composition comprising a dipeptide having an amino acid sequence represented by LH, DV or MH, or an oligopeptide including the amino acid sequence as a core sequence, or a pharmaceutically acceptable salt or a solvate thereof.

The dipeptide having an amino acid sequence represented by LH, DV or MH or the oligopeptide including the amino acid sequence as a core sequence acts to suppress microglial-mediated inflammation. Microglial-mediated inflammation is confirmed to have been related with chronic fatigue syndrome, cognitive impairment and further mood disorders such as depression. Thus, the composition containing the above dipeptide or the composition containing the oligopeptide including the amino acid sequence as a core sequence can be expected to be effective in relieving, treating or preventing a symptom of chronic fatigue syndrome, cognitive impairment and/or mood disorder by suppressing the inflammatory action of microglia.

The third embodiment of the present invention is to provide a composition for relieving or preventing a condition caused by stress, the composition comprising a dipeptide having an amino acid sequence represented by LH, DV or MH, or an oligopeptide including the amino acid sequence as a core sequence, or a pharmaceutically acceptable salt or a solvate thereof.

The dipeptide having an amino acid sequence represented by LH, DV or MH or the oligopeptide including the amino acid sequence as a core sequence acts to suppress microglial-mediated inflammation. Microglial-mediated inflammation is confirmed to have been related with a condition caused by stress. Thus, the composition containing the above dipeptide or the composition containing the oligopeptide including the amino acid sequence as a core sequence can be expected to be effective in relieving or preventing a condition caused by stress by suppressing the inflammatory action of microglia. The condition caused by stress includes particularly lack of willingness and motivation and/or a decrease in vitality.

In the present invention, the above composition may be a food or drink composition.

In the present invention, the above composition may be a pharmaceutical composition.

In the present invention, the above composition may be contained in a food or drink composition.

In the present invention, the composition can be produced by allowing the dipeptide having an amino acid sequence represented by LH, DV or MH, or the oligopeptide including the amino acid sequence as a core sequence, or a pharmaceutically acceptable salt or a solvate thereof to be contained in the respective compositions.

The dipeptide or the oligopeptide including the amino acid sequence as a core sequence may be those obtained by hydrolyzing a protein derived from a food product or the like. These peptides may be those particularly contained in sake kasu (sake lees). In this instance, the protein hydrolysate or sake kasu may further be purified and concentrated to increase a concentration of the dipeptide or the oligopeptide including the amino acid sequence as a core sequence in the composition.

When the dipeptide or the oligopeptide including the amino acid sequence as a core sequence derives from a food product or the like, the composition taken without hesitation can be provided.

The first embodiment of the production method of the present invention is a method for producing the above composition and provides the method for producing the compositions comprising a step of obtaining, by hydrolyzing a protein, a dipeptide having an amino acid sequence represented by LH, DV or MH, or an oligopeptide including the amino acid sequence as a core sequence, or a pharmaceutically acceptable salt or a solvate thereof.

The method may further comprise a step of purifying and concentrating the composition obtained by the step of obtaining, by hydrolyzing the protein, the dipeptide having the amino acid sequence represented by LH, DV or MH, or the oligopeptide including the amino acid sequence as the core sequence, or the pharmaceutically acceptable salt or the solvate thereof.

The composition obtained by the step of obtaining, by hydrolyzing the protein, the dipeptide having the amino acid sequence represented by LH, DV or MH, or the oligopeptide including the amino acid sequence as the core sequence, or the pharmaceutically acceptable salt or the solvate thereof may be sake kasu.

The second embodiment of the production method of the present invention is a method for producing a composition for relieving or preventing a condition caused by stress and provides the production method comprising a step of allowing sake kasu containing a dipeptide having an amino acid sequence represented by LH, DV or MH, or an oligopeptide including the amino acid sequence as a core sequence, or a pharmaceutically acceptable salt or a solvate thereof to be contained in the composition.

The method may further comprise a step of purifying and concentrating the sake kasu containing the dipeptide having the amino acid sequence represented by LH, DV or MH, or the oligopeptide including the amino acid sequence as the core sequence, or the pharmaceutically acceptable salt or the solvate thereof.

Advantageous Effects of Invention

According to the present invention, the composition comprising the function of suppressing microglial-mediated inflammation can be provided. Consequently, taking such a composition can achieve not only the relief, treatment and prevention of diseases induced by microglial-mediated inflammation such as chronic fatigue syndrome, cognitive impairment and mood disorders but also the relief, prevention and amelioration of conditions caused by stress but not diagnosed as an illness.

BRIEF DESCRIPTION OF THE DRAWINGS

FIG. 3 is a chart table showing the summary of test schedule in Test Example 4.

FIG. 5A is a test conceptual diagram of the social interaction test in Test Example 5.

FIG. 5B is a chart table showing the summary of test schedule in Test Example 5.

FIG. 5C is drawings showing the summary of test device for exploratory behavior evaluation in Test Example 5.

FIG. 6A is a chart showing the investigation results on time-dependent changes in the Avoidance Zone dwell time in Test Example 5.

FIG. 6B is graphs showing the investigation results on intergroup comparisons in the Avoidance Zone dwell time in Test Example 5.

FIG. 7B is a graph showing the investigation results on the inflammation suppression effect of a water extract (post-ultrafiltration) of shochu kasu against microglia in Test Example 7 (2).

DESCRIPTION OF EMBODIMENTS

Figure 1:
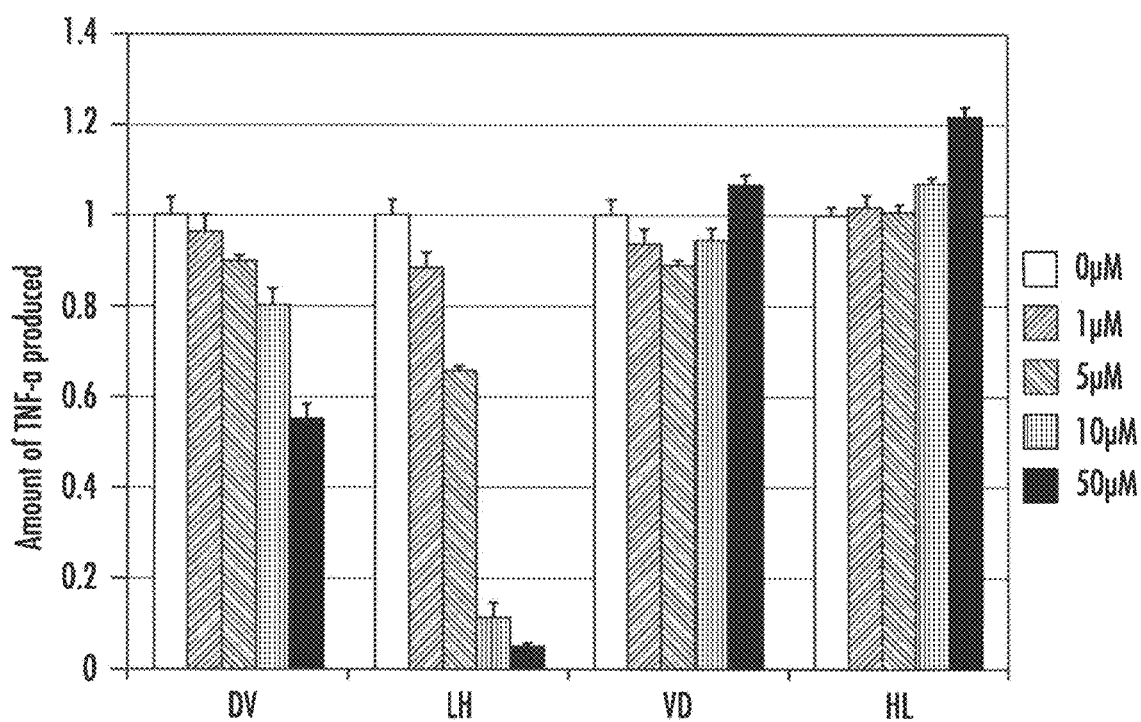
FIG. 1 is a chart showing the investigation results on the inflammation suppression effect of the dipeptides against microglia in Test Example 2.

In the present invention, the dipeptide having an amino acid sequence represented by LH, DV or MH or the oligopeptide including the amino acid sequence as a core sequence is used in the composition for suppressing microglial-mediated inflammation. The oligopeptide refers to specifically tripeptides and tetrapeptides including the above dipeptide as a core sequence. A plurality of kinds of these peptides may be used in combination. Hereinafter, these may be simply referred to as "dipeptide" or "oligopeptide".

The amino acids forming the dipeptide or the oligopeptide used in the present invention may be those consisting of all L-amino acids or all D-amino acids or may be a dipeptide or an oligopeptide having both forms in mixture. Additionally, the amino acids forming the dipeptide or the oligopeptide may be those consisting of all naturally-occurring amino acids or all modified amino acids wherein any functional group is bound to an amino acid or may be a dipeptide or an oligopeptide having both amino acids in mixture. The dipeptide or the oligopeptide, when containing two or more asymmetrical carbons, may be an enantiomer, a diastereomer or a dipeptide or an oligopeptide having both forms in mixture.

The dipeptide or the oligopeptide used in the present invention may be a pharmaceutically acceptable salt or a solvate thereof. Examples of the pharmaceutically acceptable acid addition salt include inorganic acid salts such as hydrochlorides, sulfates and phosphates and organic acid salts such as acetates, maleates, fumarates, citrates and methanesulfonates. Examples of the pharmaceutically acceptable metal salt include alkali metal salts such as sodium salts and potassium salts, alkaline earth metal salts such as magnesium salts and calcium salts, aluminum salts and zinc salts. Examples of the pharmaceutically acceptable ammonium salt include salts of ammonium and tetramethyl ammonium. Examples of the pharmaceutically acceptable organic amine addition salt include addition salts such as morpholine and piperidine.

The dipeptide or the oligopeptide used in the present invention may be those obtained by chemical synthesis or may also be those obtained by chemically or enzymatically decomposing proteins and polypeptide raw materials derived from milk, soybean, wheat, egg, meat of livestock, fish meat, seafood, barley, rice, sweet potato or potato. Specifically, all the sequences of the dipeptide or the oligopeptide used in the present invention are included at least in any of α casein, β casein, κ casein, lactoglobulin, lactalbumin, immunoglobulin, lactoperoxidase, lactoferrin and albumin of milk protein, glycinin and conglycinin of soybean protein, gliadin and glutenin of wheat protein, lipovitellin of egg yolk protein, ovalbumin, ovomucoid, ovotransferrin, mucin, lysozyme of egg white protein, collagen of chicken protein, globulin of barley protein, glutelin of rice protein, sporamin of sweet potato protein and thus the dipeptide or the oligopeptide can be prepared by acid hydrolyzing or enzymatically treating a food product or a food product raw material containing these. For example, a skim milk powder or a defatted soybean protein is dissolved and suitably treated enzymatically to obtain a composition containing about 1% of the above dipeptide or the oligopeptide. In the above decomposition, the fermentation is obviously included and examples of the food product composition obtained by fermenting a protein-containing raw material include alcohols, sake kasus, misos, nare-zushis (fermented sushi), yogurts, cheeses, fermented milks, fermented soybeans, vinegars, kojis (malted rice), soy sauces (including fish sauce), fermented fishes such as shiokara (salted fish guts) and anchovy, fermented meats such as salami and aged meats. These compositions may be used directly or may further be purified and concentrated to any degree and used.

The purification and concentration means to increase a content of the dipeptide or the oligopeptide in the composition using units such as separation, fractionation, extraction, dialysis, salting out, reprecipitation or membrane process, and a plurality of units thereof may be carried out in combination. Extraction (more preferably water extraction) and membrane process are selected as preferable means.

The dipeptide or the oligopeptide used in the present invention can be analyzed and quantitatively determined by a suitable method as necessary by a person skilled in the art. For example, the dipeptide or the oligopeptide in the composition or a food product can be analyzed and quantitatively determined by LC/MSMS illustrated in Example to be described later.

According to International Statistical Classification of Diseases and Related Health Problems by World Health Organization (WHO), the mood disorder is defined as the condition that causes troubles for carrying out daily activities due to continuous mood abnormality for a certain period of time. In the present invention, the mood disorder further includes milder symptoms such as a condition with a decrease in vitality and a condition with a decrease in inquisitiveness. Further, the enhancement of vitality and the enhancement of inquisitiveness in the present invention include the following conditions. The enhancement of vitality means that, for example, a physical activity level is higher after the composition of the present invention is taken than before to be taken, and the enhancement of inquisitiveness means, for example, to show an interest in a new subject. Note that the stress means a pressure in daily life and a sensation when a person perceives the pressure.

The enhancement of vitality and the enhancement of inquisitiveness can be measured as follows using a test animal such as a mouse. The enhancement of vitality can be evaluated, in addition to the method illustrated in Example to be described later, by the comparison of pulley working time such as a rotarod for a certain period of time between before and after the composition is taken in mice models. The enhancement of inquisitiveness can be evaluated between mice models before and after the composition is taken by, for example, comparing, when a new toy is given, the time took before the mouse model starts playing with the toy or the time during which the mouse model plays with the toy, or comparing the sociality when the mouse model meets a new mouse different from itself, how far approaches the mouse model makes to the new mouse.

The form of use of the composition of the present invention is not limited. For example, the composition can be used as a food product composition or as an additive to be added to the food product, or as a pharmaceutical composition or as an additive to be added to the pharmaceutical composition. Additionally, the composition may be used for companion animals (dogs, cats, reptiles, birds, fishes), livestock (including poultry) and farm-raised fishes (preferably animals and livestock which are mammals) in addition to human.

For allowing the dipeptide or the oligopeptide to effectively acts on human and animals, the composition is preferably in the form of containing 0.00001 to 100 mass %, more preferably in the form of containing 0.0001 to 100 mass %, most preferably in the form of containing 0.001 to 100 mass %, of the dipeptide or the oligopeptide (the total conversion when a plurality of kinds are contained).

The dipeptide or the oligopeptide can be used in the method for suppressing microglial-mediated inflammation. These peptides can further be used in the method for relieving, treating or preventing a symptom of chronic fatigue syndrome, cognitive impairment and/or mood disorder. These peptides can further be used in the method for relieving or preventing conditions caused by stress such as, for example, lack of willingness and motivation and/or a decrease in vitality. These can be achieved by taking or administering an effective amount of the dipeptide or the oligopeptide. Note that the method does not include the so-called medical practice for human.

The form of the composition provided by the present invention is not limited and may be in the form of liquid, semi-liquid or solid and also encompasses food product compositions such as drinks. Additionally, the form includes the so-called health food products, functional food products, nutritional food products and supplement, and further encompasses health promoting food products such as food products labelled with reduction of disease risk claim (food for specified health uses, nutritive functional food products, foods with functional claims) and foods for patients.

When the food product composition is vinegars, alcohols or lees thereof, the dipeptide or the oligopeptide is usually contained as a result of the protein in the raw material being decomposed by an enzyme and a microorganism added or being decomposed by an enzyme originally contained in the raw material. Obviously, those produced by newly or further adding the dipeptide or the oligopeptide to vinegars and alcohols or lees thereof may also be acceptable. The raw material of vinegars and alcohols needs to contain a protein, with preferable examples including wheats (including malts), rices (including whole rice), potatoes, corns, beans and buckwheats. Barley, rice and sweet potato are more preferable. Additionally, the lee of alcohols is more preferable form. The lee may or may not contain alcohol but those containing no alcohol is preferable. The removal of alcohol is carried out by a known method such as drying in air.

The production of alcohols herein includes (i) a method in which a raw material is subjected to the primary treatment (decomposition treatment by the addition of an enzyme and a microorganism or decomposition treatment by an enzyme derived from a raw material itself) and, after solid-liquid separation, the liquid is subjected to a fermentation step to obtain an alcohol such as whiskies and fruit wines, and (ii) a method in which a raw material subjected to the primary treatment (decomposition treatment by the addition of an enzyme and a microorganism or decomposition treatment by an enzyme derived from a raw material itself) is subjected to a fermentation step by further adding the raw material, an enzyme and a microorganism and, after fermentation, the solid-liquid separation and distillation are carried out to obtain an alcohol such as Japanese rice wine and shochu. The lees of alcohols of the present invention may be those obtained by either (i) or (ii), but those obtained by (ii) are preferable. The solid obtained in (i) includes whisky lees and grape pomace, and the solid obtained in (ii) includes sake kasu of Japanese rice wine and shochu kasu. In the present Description, the lees of alcohols are collectively termed sake kasu.

Examples of the non-alcohol drink when the food product composition is applied to a non-alcohol drink include, but not limited thereto, mineral waters, near waters, isotonic drinks, tea drinks, milk drinks, coffee drinks, fruit juice-containing drinks, vegetable juice-containing drinks, fruit juice- and vegetable juice-containing drinks, carbonated drinks, alcohol-free beer taste drinks. The non-alcohol drink may be beer drinks having an alcohol content of less than 1% such as non-alcohol beer. The mineral water encompasses both effervescent and non-effervescent mineral waters.

The tea drink in the above non-alcohol drinks refers to a drink extracted from leaves (tea leaves) of the tea plant, an evergreen belonging to Theaceae family, or a drink extracted from leaves of plants other than the tea plant or grains, and encompasses fermented teas, semi-fermented teas and non-fermented teas. Specific examples of the tea drink include Japanese teas (e.g., green tea, barley teas), English teas, herb teas (e.g., Jasmine tea), Chinese teas (e.g., Chinese green tea, oolong tea) and roasted green tea. The milk drink refers to a drink mainly made from raw milk, cow's milk or a food product produced using these milks as a raw material, and also encompasses, for example, those having a processed milk as a raw material such as nutrition enriched milks, flavored milks and sweetened decomposition milks, in addition to those directly using a cow's milk or the like as the ingredient.

Examples of the fruit used in the fruit juice-containing drinks and the fruit juice- and vegetable juice-containing drinks include apples, oranges, grapes, bananas, pears, peaches, mangos, acai and blueberries. Examples of the vegetable used in the vegetable juice-containing drinks and the fruit juice- and vegetable juice-containing drinks include tomatoes, carrots, celeries, pumpkins and cucumbers.

When the composition provided by the present invention is used as a food product composition, an amount to be taken daily by an adult is typically 0.0001 to 40 g, preferably 0.001 to 20 g, further preferably 0.001 to 2 g, of the dipeptide or the oligopeptide (the total conversion when a plurality of kinds are contained). For allowing the oligopeptide to effectively act, the composition is preferably in the form of containing 0.00001 to 100 mass %, more preferably in the form of containing 0.0001 to 100 mass %, further preferably in the form of containing 0.001 to 100 mass %, even further preferably in the form of containing 0.01 to 90 mass %, most preferably in the form of containing 0.1 to 80 mass %, of the dipeptide or the oligopeptide (the total conversion when a plurality of kinds are contained). Additionally, the composition, in 1 meal or in a container subdivided as 1 meal, is preferably in the form of containing 0.0001 to 40 g, more preferably in the form of containing 0.001 to 20 g, further preferably in the form of containing 0.001 to 2 g, of the dipeptide or the oligopeptide (the total conversion when a plurality of kinds are contained). When used as a drink, the composition is preferably in the form of containing 0.000001 to 10 mass %, more preferably in the form of containing 0.00001 to 5 mass %, further preferably in the form of containing 0.0001 to 5 mass %, even further preferably in the form of containing 0.001 to 5 mass %, most preferably in the form of containing 0.01 to 1 mass %, of the dipeptide or the oligopeptide (the total conversion when a plurality of kinds are contained).

The dipeptide or the oligopeptide has an inflammation suppression action and a stress relief action of microglia and thus can be provided as contained in food products taken daily or in food products taken as supplement.

These peptides can also be contained in health food products and functional food products, or preferably in food products containing the component intended to demonstrate the inflammation suppression action on microglia, mood disorder suppression action or stress relief effect. The component intended to demonstrate the inflammation suppression action on microglia, mood disorder suppression action or stress relief effect includes theanine, polyphenols, rosemary hydrolysate, ubidecarenone, Siberian *ginseng*, actin, *lactobacillus* fermented sour milk and B-eudesmol.

Further, in recent years the treatment for long-term mood disorder is said to possibly prevent to a certain extent the transition to cognitive dysfunction and it is thus considered useful to take the component capable of relieving and ameliorating the condition with a decreased resistance against mood disorder and stress when taking a food product intended to prevent and treat cognitive dysfunction. The composition provided by the present invention has the microglia inflammation suppression action and thus can also be contained in a food product containing the component intended to prevent and treat cognitive dysfunction. The component intended to prevent cognitive dysfunction includes ω-3 fatty acids such as eicosapentaenoic acid (EPA) and docosahexaenoic acid (DHA), polyphenols such as gingko leaf extract, resveratrol and curcumine, lecithin, isohumulone and vitamins that prevent the metabolic disorder of homocysteine, a risk factor of Alzheimer's disease.

The dipeptide or the oligopeptide provides the effect when taken single time but when taken continuously in the form of a food or drink product, the excessive inflammatory action of microglia is suppressed and, when adjusted suitably, the vulnerability to environmental factors such as stress is reduced, namely a condition with the resistance against stress can be achieved.

The pharmaceutical composition contains at least one of the above dipeptide and the oligopeptide as the effective component and can be produced by mixing a carrier, an excipient, a binder and a diluent therewith. The pharmaceutical composition can be orally and parenterally administered, and when orally administered, the pharmaceutical composition may be in any form such as a granular, a powder, a tablet, a pill, a capsule or a syrup. Examples of the parenteral administration form include external preparations such as an injection, an intravenous drip, a transnasal administration preparation, but not limited thereto.

When used as a pharmaceutical drug, the dose thereof varies depending on the administration form, age and body weight of a patient, nature or severity of a symptom to be treated, but a dose for the oral administration by an adult daily is typically 0.0001 to 40 g, preferably 0.001 to 20 g, further preferably 0.001 to 2 g, of the dipeptide or the oligopeptide (the total conversion when a plurality of kinds are contained). When parenterally administered, a dose for, for example, intravenous administration by an adult daily is 0.00001 to 4 g, preferably 0.0001 to 2 g, further preferably 0.0001 to 0.2 g, of the dipeptide or the oligopeptide (the total conversion when a plurality of kinds are contained). Note that, for these doses, the most suitable form is obviously selected as necessary depending on various conditions.

The dipeptide or the oligopeptide has a comparatively low molecular weight and thus easily permeates the brain bather after taken into the body and likely to demonstrate the effect in the brain. In addition, when a protein contained in a food product is used as a raw material, a very safe composition can be provided.

EXAMPLE

Hereinafter, the details of the present invention are described with reference to Examples, but are not limited thereto.

Test Example 1

A dipeptide was first synthesized and the following test was carried out to comprehensively investigate the impact of the oligopeptide to the proinflammatory cytokine production of microglia.

[Dipeptide]

Of 361 combinations of dipeptides that can be formed by 19 amino acids of the 20 proteinogenic amino acids except for cysteine (C), 336 combinations of dipeptides, excluding 25 dipeptides, were prepared as combinations of the N-terminal amino acid (First amino acid) and the C-terminal amino acid (Second amino acid) thereof as shown in the following Table 1. Note that when stereoisomers were present, L-form was used.

[Microglia]

Microglia were isolated from the mouse brain by the magnetic cell sorting method. Specifically, the brain removed from a mouse was treated with papain to obtain a brain tissue dispersion and the enzyme reaction was stopped. Subsequently, the dispersion was reacted to CD11b antibody (manufactured by Miltenyi Biotec), a common microglia marker magnetically labelled with superparamagnetic microbeads, to carry out magnetic separation whereby microglia were isolated.

[Evaluation of Anti-Inflammatory Activity]

The isolated microglia cell was cultured for 12 hours in medium to which the above 336 dipeptides were added in a concentration of 50 μM each. Subsequently, 5 ng/ml of lipopolysaccharide (LPS, manufactured by SIGMA-ALDRICH) and 0.5 ng/ml of IFN-γ (manufactured by R&D system) were added thereto, the cell was further cultured for 12 hours and TNF-α contained in the culture supernatant was quantitatively determined using an ELISA kit (manufactured by eBioscience). Using wells to which the peptides were not added as controls, the production rate of TNF-α when the control has a rate of 1 was calculated. The results are shown in Table 1. Note that the results are average values of three consecutive data. Additionally, hereinafter the amino acids are shown in one-letter abbreviations.

TABLE 1

| | | | First amino acid | | | | | | | | | |
|---|---|---|---|---|---|---|---|---|---|---|---|---|
| | | | A | D | E | F | G | H | I | K | L |
| | | Molecular | | | | | Amount of residue | | | | |
| | | weight | 89.09 | 133.1 | 147.13 | 165.19 | 75.07 | 155.16 | 131.17 | 146.19 | 131.17 |
| Second amino acid | A | 71.07 | 1.03 | 0.74 | 0.72 | 0.8 | 0.87 | 1.23 | 0.82 | 0.99 | 0.76 |
| | D | 115.08 | 0.9 | 0.74 | 0.83 | 0.77 | 1.02 | 0.91 | 0.88 | 0.79 | 0.76 |
| | E | 129.11 | 0.85 | | 0.82 | 0.86 | 0.89 | 1.15 | 0.71 | 0.77 | 0.84 |
| | F | 147.17 | 0.86 | 0.8 | | 0.92 | 0.98 | 0.85 | 0.79 | 0.84 | 0.77 |
| | G | 57.05 | 0.72 | 0.78 | 0.79 | 0.92 | 0.91 | | | 0.79 | 0.63 |
| | H | 137.14 | 0.75 | 0.72 | 0.85 | 0.93 | 0.66 | 0.9 | 0.81 | 0.97 | 0.06 |
| | I | 113.15 | 0.67 | | 0.84 | 0.8 | 0.92 | 0.95 | 0.84 | 0.68 | 0.69 |
| | K | 128.17 | 0.82 | 0.81 | 0.89 | 0.81 | | 0.93 | 0.81 | 0.8 | |
| | L | 113.15 | 1.07 | 0.91 | 0.91 | 0.79 | | 1.2 | 0.97 | 0.67 | 0.78 |
| | M | 131.19 | 1.06 | 0.98 | 0.79 | 0.8 | 1.01 | 0.99 | 0.89 | 0.69 | 0.82 |
| | N | 114.1 | | 0.82 | 0.78 | 0.86 | 1.27 | 0.85 | 0.85 | 0.76 | 0.82 |
| | P | 97.11 | 1.11 | 0.84 | 0.88 | | 0.96 | 0.98 | 0.81 | 0.81 | |
| | Q | 128.13 | 0.87 | 0.83 | 0.83 | 1.03 | 0.94 | | 0.74 | 0.72 | |
| | R | 156.18 | 0.89 | 0.98 | 0.95 | 1.04 | 0.81 | 0.85 | 0.76 | 0.79 | |
| | S | 87.07 | 0.89 | 0.93 | 0.89 | 1 | 0.79 | 0.78 | 0.79 | 0.84 | |
| | T | 101.1 | 0.84 | 0.78 | 0.91 | 0.85 | 0.78 | 0.91 | 0.87 | 0.74 | 0.86 |
| | V | 99.13 | 0.97 | 0.2 | 0.86 | 0.81 | 0.85 | 0.78 | 0.9 | 0.61 | 0.75 |
| | W | 186.2 | 0.89 | 0.83 | 0.79 | 0.79 | 0.86 | 0.87 | 0.89 | 0.79 | 0.83 |
| | Y | 163.17 | 0.9 | 0.8 | 0.75 | 0.76 | 0.92 | 0.87 | | 0.75 | 0.71 |

| | | First amino acid | | | | | | | | | |
|---|---|---|---|---|---|---|---|---|---|---|
| | | M | N | P | Q | R | S | T | V | W | Y |
| | | | | | | Amount of residue | | | | | |
| | | 149.21 | 132.12 | 115.13 | 146.15 | 174.2 | 105.09 | 119.12 | 117.15 | 204.22 | 181.19 |
| Second amino acid | A | 0.69 | 0.7 | 1.02 | 0.93 | 0.83 | 0.84 | 0.97 | 0.9 | 0.83 | 0.91 |
| | D | 0.68 | 0.75 | 0.83 | 0.83 | 0.79 | 0.79 | 1 | 0.78 | 0.83 | 0.89 |
| | E | 0.73 | 0.8 | 0.89 | 0.76 | 0.8 | 0.87 | 0.97 | 0.87 | 0.88 | 0.94 |
| | F | 0.71 | 0.75 | 0.81 | 0.72 | 0.75 | 0.84 | 0.87 | 0.81 | 0.95 | 1.02 |
| | G | 0.84 | 0.72 | 0.77 | 0.86 | 0.79 | | 0.81 | 0.84 | 0.91 | 0.95 |
| | H | 0.44 | 0.73 | 0.83 | 0.73 | 0.83 | 0.93 | 0.87 | 0.93 | 1 | 1.02 |
| | I | 0.93 | 0.76 | 0.84 | 0.74 | 0.81 | 0.84 | 0.92 | 0.93 | 0.88 | 0.95 |
| | K | 1.09 | 0.76 | 0.8 | 0.74 | 0.73 | 0.81 | 0.89 | 1.03 | 0.85 | 0.96 |
| | L | 1.3 | 0.75 | | 0.81 | 0.77 | 0.73 | 0.91 | 0.9 | 0.84 | 1.01 |
| | M | 0.77 | 0.74 | 0.84 | 0.84 | 0.83 | 0.77 | 0.89 | 0.91 | 0.85 | 0.88 |
| | N | 0.75 | 0.84 | 0.86 | 0.9 | 0.8 | 0.76 | 0.97 | 0.91 | 0.85 | 0.93 |
| | P | | 0.83 | 0.81 | 0.8 | 0.85 | 0.83 | 0.92 | 0.91 | 0.87 | 0.81 |
| | Q | 0.77 | 0.76 | 0.83 | 0.73 | | 0.91 | 0.85 | 0.99 | 0.9 | 0.83 |
| | R | 1.01 | 0.79 | | | 0.88 | 1.06 | 0.86 | 0.99 | 0.99 | 0.89 |
| | S | 0.8 | | 0.74 | 0.85 | 0.92 | 1 | 0.82 | 0.95 | 0.95 | 0.89 |
| | T | 0.75 | 0.84 | 0.83 | 0.82 | 0.88 | 0.78 | 0.85 | 1.03 | 0.82 | 0.81 |
| | V | 0.77 | 0.81 | 0.76 | 0.91 | 0.78 | 0.77 | 1.04 | | 0.81 | 0.95 |
| | W | 0.71 | 0.88 | 0.72 | 0.82 | 0.8 | 0.84 | 0.94 | 0.91 | 0.87 | 0.82 |
| | Y | 0.74 | 0.91 | 0.8 | 0.77 | | 0.91 | 1.02 | 0.87 | 0.86 | 0.91 |

Of the 336 dipeptides, the 112 dipeptides AG, AH, AI, DA, DD, DF, DG, DH, DT, DV, DY, EA, EG, EM, EN, EW, EY, FA, FD, FI, FL, FM, FW, FY, GH, GS, GT, HS, HV, IE, IF, IQ, IR, IS, KD, KE, KG, KI, KK, KL, KM, KN, KQ, KR, KT, KV, KW, KY, LA, LD, LF, LG, LH, LI, LL, LV, LY, MA, MD, ME, MF, MH, MM, MN, MQ, MS, MT, MV, MW, MY, NA, ND, NE, NF, NG, NH, NI, NK, NL, NM, NQ, NR, PG, PK, PS, PV, PW, PY, QE, QF, QH, QI, QK, QP, QQ, QY, RD, RE, RF, RG, RK, RL, RN, RV, RW, SD, SL, SM, SN, ST, SV and VD were found to have the activity for suppressing the TNF-α production to 0.80 or less relative to the control.

Additionally, the peptides having the activity for suppressing the TNF-α production with a degree of ¼, that is, 0.75 or less relative to the control, were the 50 dipeptides AG, AH, AI, DA, DD, DH, DV, EA, EY, GH, IE, IQ, KI, KL, KM, KQ, KT, KV, KY, LG, LH, LI, LV, LY, MA, MD, ME, MF, MH, MN, MT, MW, MY, NA, ND, NF, NG, NH, NL, NM, PS, PW, QF, QH, QI, QK, QQ, RF, RK and SL.

Further, the peptides having the activity for suppressing the TNF-α production to 0.70 or less were the 14 dipeptides AI, DV, GH, KI, KL, KM, KV, LG, LH, LI, MA, MD, MH and NA. Of these, it was revealed that the 3 dipeptides LH, DV and MH, suppressing the TNF-α production to 0.5 or less have a very good inflammation suppression effect as found in 0.06, 0.20 and 0.44, respectively.

Test Example 2

Of the dipeptides confirmed to have a good anti-inflammation effect in Test Example 1, further analysis was carried out on LH and DV. First, the analysis was carried out to see if the anti-inflammatory effects of these dipeptides are concentration-dependent.

The TNF-α productions were measured using ELISA in the same manner as in Test Example 1 except that the dipeptides were cultured with microglia at different concentrations from 1 µM to 50 µM. Note that, for the control, those cultured with no addition of the peptides were used as in Test Example 1. For comparison, the dipeptides having the same amino acid composition with different sequences, that it, VD and HL were also measured for the TNF-α production at different concentrations. The results are shown in FIG. 1.

As shown in FIG. 1, the anti-inflammatory actions of the dipeptides DV and LH are concentration-dependent. On the other hand, neither of the dipeptides VD nor HL, having the same amino acid composition but the sequence with the N terminus and the C terminus replaced, demonstrated anti-inflammatory activity.

Test Example 3

Figure 2:
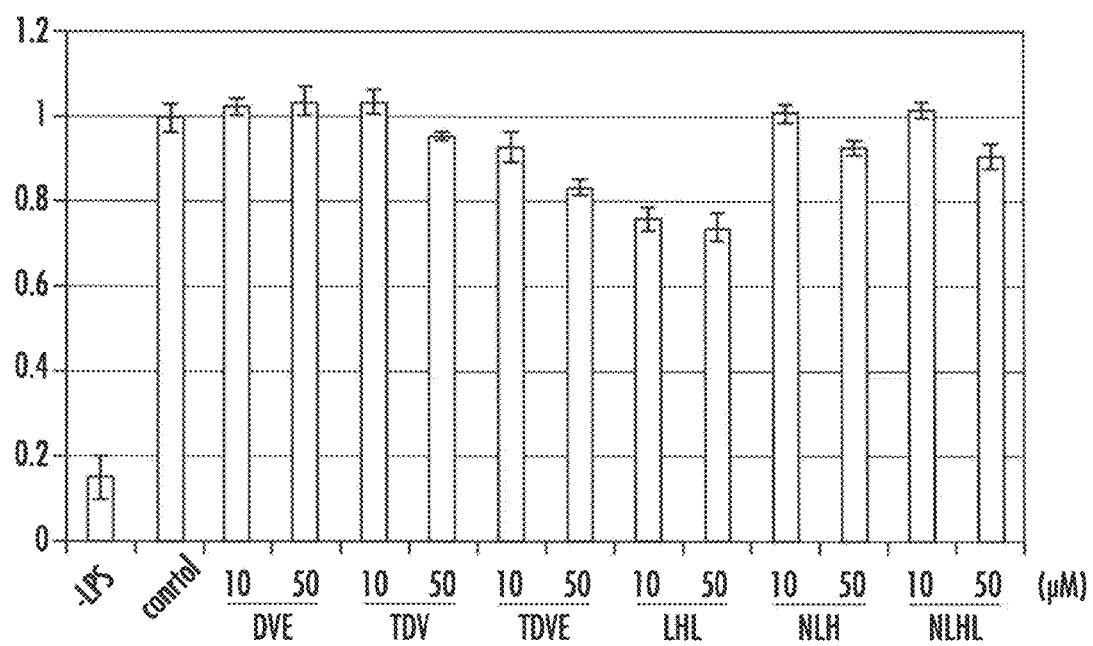
FIG. 2 is a chart showing the investigation results on the inflammation suppression effect of the tripeptides DVE, TDV, LHL and NLH and the tetrapeptides TDVE (SEQ ID NO: 45) and NLHL (SEQ ID NO: 46) having the dipeptide as a core sequence against microglia in Test Example 3.

Next, the inflammation suppression effects of tripeptides and tetrapeptides having DV and LH as the core sequences against microglia were analyzed to see if these dipeptides can function as the core sequences. The results are shown in FIG. 2. Tripeptides DVE, TDV, LHL and NLH and tetrapeptides TDVE (SEQ ID NO: 45) and NLHL (SEQ ID NO: 46) having the 2 peptides DV and LH as the core sequences were analyzed for the anti-inflammatory action.

The TNF-α was measured using ELISA in the same manner as in Test Example 1 except that microglia were cultured using the above peptides at concentrations of 10 µM and 50 µM. The results are shown in FIG. 2.

The oligopeptides used in the analysis, except DVE, demonstrated the effect of suppressing the inflammatory action of microglia. There is no regularity found at present between the inflammation suppression effect on microglia and the amino acid sequence. For example, when the anti-inflammatory actions of DVE, TDV and TDVE (SEQ ID NO: 45) containing DV as the core sequence are compared, the inflammation suppression effect of TDVE (SEQ ID NO: 45) is the most intense whereby the presence or absence of T does not determine the inflammatory action. Additionally, there is no correlation found between the chain length of the peptides and the activity thereof.

Considering the above analysis results, the dipeptide sequences disclosed in the present invention as the core sequences may have the inflammation suppression action even when used as a tripeptide or a tetrapeptide.

Test Example 4

It was investigated whether the inflammation in the brain was relieved by LH administration.

Six-week-old ICR (CD-1) male mice (manufactured by Charles River Laboratories Japan, Inc.) were divided into 4 groups. LH (manufactured by Kokusan Chemical Co., Ltd.) prepared to make 0, 10, 50 mg/kg per body weight was forcefully orally administered into the stomach of four mice in LH 0 mg group, three mice in LH 10 mg group and five mice in LH 50 mg group, respectively once daily for 7 consecutive days.

For the purpose of inducing intracerebral inflammation, on Day 7 of the LH administration, LPS (manufactured by SIGMA-ALDRICH) dissolved in distilled water to make 1.5 mg/mL was intraventricularly administered to make 0.5 mg/kg per body weight in terms of LPS thirty minutes after the LH administration. Three hours after the LPS administration, the mice were euthanized to collect the cerebral cortex and the hippocampus for sampling. Three mice in LPS non-administered group, wherein LH and LPS were not administered, were intraventricularly administered with 10 µL of distilled water in place of LPS and the tissues were collected for sampling in the same manner as in the above 3 groups.

Subsequently, the amounts of TNF-α in the sample tissues were evaluated. More specifically, the collected cerebral cortex and hippocampus were bead-crushed in RIM buffer (manufactured by WAKO) and a TNF-α was quantitatively determined using an ELISA kit ("Mouse TNF alpha ELISA Ready-SET-Go!", manufactured by eBioscience). The obtained TNF-α quantitatively determined value was divided by the total protein concentration in the lysate quantitatively determined by the BCA method to be used as the TNF-α content per unit protein mass.

Figure 4:
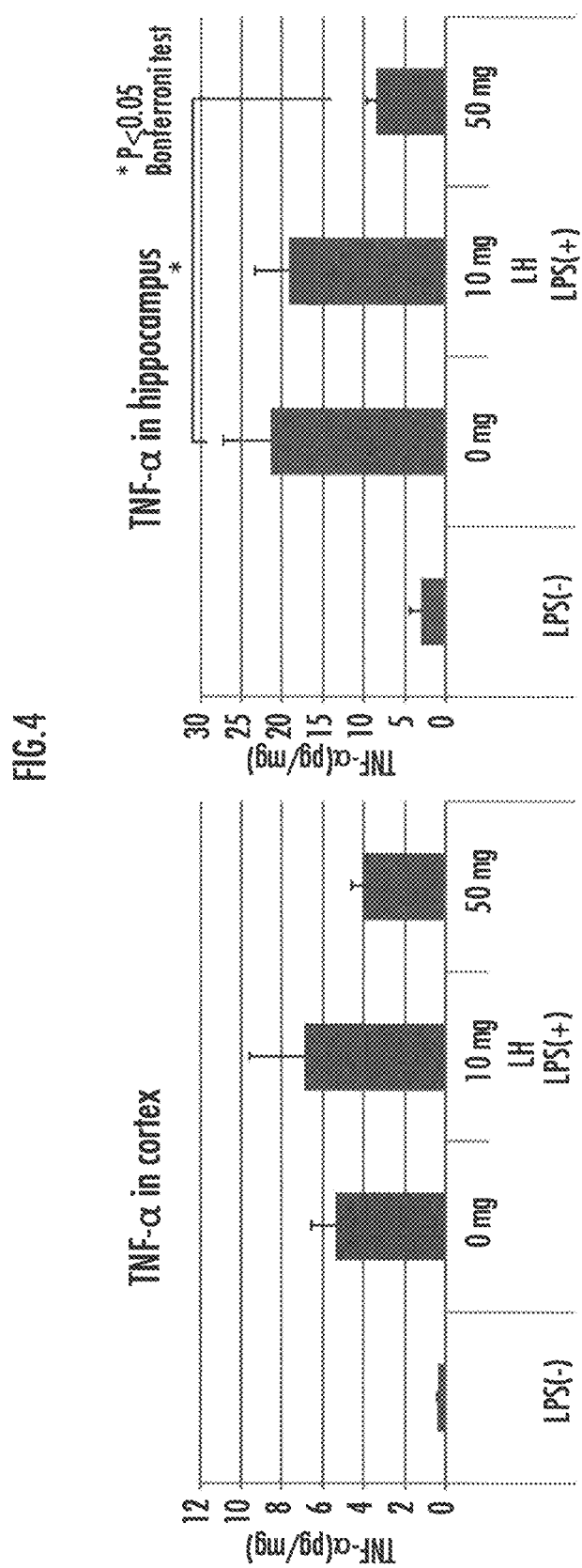
FIG. 4 is graphs showing the investigation results on the intracerebral inflammation suppression effect of the dipeptide administration into the stomach of mice in Test Example 4.

The summary of test schedule is shown in FIG. 3 and the results are shown in FIG. 4. The results are presented in the average value±standard error of the measured values in each group.

As a result, the LH 50 mg group tended to have smaller amounts of TNF-α in the cerebral cortex and hippocampus than the LH 0 mg group, whereby the difference between the LH 0 mg group and the 50 mg group was significant in the hippocampus. From the above results, it was revealed that the orally administered LH suppressed the inflammatory action in the brain.

Test Example 5

(1) Social Interaction Test
When exposed to stress, chronic fatigue, decreased willingness and depressive conditions may appear along therewith, and studies conducted in recent years revealed that the inflammation in the brain is associated as the mechanism therewith (Tomoyuki Furuyashiki, "Role of inflammation-related molecules and involvement with microglia activation in psychological stress", Experimental Medicine Vol. 30-No. 13 2012, 65-71).

Then, LH confirmed to demonstrate the inflammation suppression action in the brain in Test Example 4 was evaluated to see if the relief and suppression effects to stress are rendered using an animal. Specifically, the relief of stress condition and willingness improvement and vitality enhancement effects by the LH administration were investigated by the social interaction test using a stress-imposed model.

Mouse originally has the nature of social exploratory behavior and thus, when placed in a chamber in which a new individual exists, becomes to stay near the place (cage for the new individual) at which the new individual (Aggressor) is mainly present and stays away most of the time from the area (Avoidance Zone) farthest from the new individual (Aggressor) (Vaishnav Krishanan., et al Cell, 2007, Vol. 131(2), p 391-404). However, the stress-imposed mouse has growing anxiety to the new individual (Aggressor) and decreased willingness and thus avoids staying near the new individual (Aggressor) thereby increasing dwell time in Avoidance Zone. Accordingly, the condition of the mouse against stress can be evaluated by introducing a social defeat model mouse to a chamber in which a new individual (Aggressor) exists and measuring Avoidance Zone dwell time. In this case, if the model mouse who took LH has the relief of stress, willingness improvement and vitality enhancement, the mouse has reduced dwell time in Avoidance Zone compared with an LH non-taken mouse.

(2) Method

The test summary is shown in FIGS. 5A to 5C.

Eight-week-old male C57BL/6N mice (manufactured by Charles River Laboratories Japan, Inc. Hereinafter, also referred to as "test animal") as Repeated Social Defeat Stress model (Social defeat model) were divided into 3 groups of a stress free group (ND group), a group to which stress was imposed and who took 0.1% (W/W) LH-containing feed (LH diet group) and a group to which stress was imposed and who took LH free diet (control diet group). Each group has ten mice and each mouse was kept in a separate cage.

The LH diet group was allowed to take freely AIN93-G (manufactured by Oriental Yeast Co., Ltd.) feed (hereinafter referred to as "test diet") prepared by adding LH to make the final concentration of 0.1% (W/W) for 7 days before the day the stress imposition started and the feeding was continued until the following day the stress imposition was completed (the day the exploratory behavior evaluation was completed). The ND group and the control diet group were allowed to freely take AIN93-G feed to which LH was not added from the same day the LH diet group started taking the test diet (For the ND group, "Day 1" was similarly defined as the day the stress imposition started as in the LH group and the control diet group).

Stress was imposed to the LH diet group and the control diet group by allowing an ICR (CD-1) mouse (manufactured by Charles River Laboratories Japan, Inc.) as Aggressor to cohabitate therewith once daily, for 10 minutes, from the day the stress imposition started.

The exploratory behavior evaluation was carried out on Days −1, 2, 4, 8 and 11 of the stress imposition in each group. The exploratory behavior evaluation is the test for evaluating the exploratory behavior of a test animal against a new individual (Aggressor). The summary of test device was shown in FIG. 5C. An ICR (CD-1) mouse, a new individual (Aggressor), in a cage was placed by the wall of a chamber sized length 40 cm, width 30 cm, height 30 cm, into which a test animal was placed and allowed to freely explore for 5 minutes (for 300 seconds) and dwell time in Avoidance Zone was measured. Note that the exploratory behavior evaluation on Day −1 is the evaluation of the exploratory behavior of the test animal in the absence of the new individual (Aggressor).

(3) Result

The time-dependent changes in dwell time in Avoidance Zone of each group are shown in FIG. 6A. The dwell times are presented in the average value±standard error of the measured values of each group. In each group, the Avoidance Zone dwell time was found to likely increase over time. When compared with the ND group, the degree of time-dependent increase tended to be higher in the groups on which stress was imposed (Defeated group; LH group and control diet group). Further, when compared with the control diet group, the degree of time-dependent increase in the LH diet group tended to be suppressed.

The Avoidance Zone dwell times on Days 2, 4, 8 and 11 of the stress imposition are shown in FIG. 6B. The dwell times are presented in the average value±standard error of the measured values of each group. At any point of the time, the dwell time in Avoidance Zone in the LH diet group tended to be shorter than the control diet group. On Day 8, the difference in the Avoidance Zone dwell time between the control diet group and the LH diet group was significant.

From the above, it was suggested that the vitality decreases by the stress imposition when LH was not taken but the vitality decrease was suppressed by taking LH. More specifically, it was revealed that the chronic stress is relieved and the lack of willingness and motivation and a decrease in vitality are suppressed by LH.

Test Example 6

The dipeptides and the oligopeptides containing the dipeptides found effective in having high inflammation suppression activity against microglia in Test Example 1 were examined to see if included in the sequences of proteins used in food products. Specifically, it was examined whether the sequences of LH, DV, MH, LHL, NLH, TDVE (SEQ ID NO: 45) and NLHL (SEQ ID NO: 46) appeared in the 34 proteins shown in the following Table 2.

TABLE 2

| Source protein | | Protein name | SEQ ID NO. |
|---|---|---|---|
| Milk | Casein | α-S-1Casein (214 aa protein) | SEQ ID NO: 1 |
| | | β-Casein (224 aa protein) | SEQ ID NO: 2 |
| | | κ-Casein (190 aa protein) | SEQ ID NO: 3 |
| | | γ-Casein → decomposition product of β-Casein | |
| | | protease peptane → decomposition product of β-Casein | |

TABLE 2-continued

| Source protein | | Protein name | SEQ ID NO. |
|---|---|---|---|
| | Whey | β-Lactoglobulin (178 aa protein) | SEQ ID NO: 4 |
| | | α-Lactalbumin (142 aa protein) | SEQ ID NO: 5 |
| | | LP: Lactoperoxidase (712 aa protein) | SEQ ID NO: 6 |
| | | LF: Lactoferrin 708 aa protein) | SEQ ID NO: 7 |
| | | Immunoglobulin H chain → only a part of the sequence (Ig: Immunoglobulin) (164 aa protein) | SEQ ID NO: 8 |
| | | Immunoglobulin L chain only a part of the sequence (Ig: Immunoglobulin) (101 aa protein) | SEQ ID NO: 9 |
| | BSA | BOVIN Serum albumin (607 aa protein) | SEQ ID NO: 10 |
| Soybean | Glycinin | SOYBN Glycinin (563 aa protein) | SEQ ID NO: 11 |
| | β-Conglycinin | Beta-conglycinin, alpha' chain (639 aa protein) | SEQ ID NO: 12 |
| | | SOYBN Beta-conglycinin alpha-subunit (623 aa protein) | SEQ ID NO: 13 |
| | | SOYBN Beta-conglycinin, beta chain (439 aa protein) | SEQ ID NO: 14 |
| Wheat | Gliadin | WHEAT Alpha-gliadin (Fragment) (288 aa protein) | SEQ ID NO: 15 |
| | | WHEAT Gamma-gliadin (302 aa protein) | SEQ ID NO: 16 |
| | | WHEAT Alpha/beta-gliadin (331 aa protein) | SEQ ID NO: 17 |
| | | WHEAT Omega-5 gliadin (439 aa protein) | SEQ ID NO: 18 |
| | Glutenin | WHEAT High-molecular-weight glutenin subunit 2.6 OS (1025 aa protein) | SEQ ID NO: 19 |
| | | WHEAT Low molecular weight glutenin subunit OS (392 aa protein) | SEQ ID NO: 20 |
| Egg yolk | Lipovitellin | Vitellogenin-1 (Minor vitollogenin) (Vitellogenin I) (1,912 aa protein) | SEQ ID NO: 21 |
| | | Vitellogenin-2 (Major vitollogenin) (1850 aa protein) | SEQ ID NO: 22 |
| Egg white | Ovalbumin | Ovalbumin (Allergen Gal d II) (Egg albumin) (386 aa protein) | SEQ ID NO: 23 |
| | Ovotransferrin | Ovotransferrin(*Gallus gallus*, Chicken) (738 aa protein) | SEQ ID NO: 24 |
| | Ovomucoid | Ovomucoid (Allergen Gal d I) (allergen Gal d I) (210 aa protein) | SEQ ID NO: 25 |
| | Ovomucin | Mucin-5B (Ovomucin, alpha-subunit) (2108 aa protein) | SEQ ID NO: 26 |
| | Ovomucin | Mucin-6 (Ovomucin, beta-subunit) *Gallus gallus* (Chicken) (1185 aa protein) | SEQ ID NO: 27 |
| | Lysozyme | Lysozyme g *Gallus gallus* (Chicken) (211 aa protein) | SEQ ID NO: 28 |
| | | Lysozyme C (147 aa protein) | SEQ ID NO: 29 |
| Chicken | Collagen | Collagen alpha-1(I) chain (Alpha-1 type I collagen) chicken (1453 aa protein) | SEQ ID NO: 30 |
| | | CHICK Collagen alpha-1(II) chain (Fragment) (369 aa protein) | SEQ ID NO: 31 |
| | | CHICK Collagen alpha-2(I) chain (Fragments) (1362 aa protein) | SEQ ID NO: 32 |

Table 3 shows the results on appearance of dipeptide sequences, tripeptides and tetrapeptides in each of casein proteins, whey proteins and BSA. Note that as γ-Casein and proteose peptone are β-Casein decomposition products, it is considered that the oligopeptides confirmed to have appeared in β-Casein may also appear in γ-Casein and proteose peptone.

TABLE 3

| | Milk | | | | | | |
|---|---|---|---|---|---|---|---|
| | Casein | | | | | Whey | |
| | | | | | protease | | |
| | α-S-1Casein | β-Casein | κ-Casein | γ-Casein → decomposition product of β-Casein | peptone → decomposition product of β-Casein | β-Lactoglobulin | α-Lactalbumin |
| Oligopeptides | 214 aa protein | 224 aa protein | 190 aa protein | | | 178 aa protein | 142 aa protein |
| LH | ○ | ○ | — | — | — | — | — |
| DV | ○ | ○ | — | — | — | — | — |
| MH | — | ○ | — | — | — | ○ | — |
| LHL | — | ○ | — | — | — | — | — |
| NLH | — | ○ | — | — | — | — | — |
| TDVE | — | ○ | — | — | — | — | — |
| NLHL | — | ○ | — | — | — | — | — |

TABLE 3-continued

| | | | Milk | | |
| --- | --- | --- | --- | --- | --- |
| | | | Whey | | |
| Oligopeptides | I.P: Lactoperoxidase 711 aa protein | I.F: Lactoferrin 708 aa protein | Immuno-globulin H chain → only a part of the sequence (Ig: Immuno globulin) 164 aa protein | Immuno-globulin L chain only a part of the sequence (Ig: Immuno globulin) 101 aa protein | BSA BOVIN Serum albumin 607 aa protein |
| LH | ○ | ○ | — | — | ○ |
| DV | — | ○ | — | — | ○ |
| MH | — | — | — | — | — |
| LHL | — | — | — | — | — |
| NLH | — | — | — | — | — |
| TDVE | — | — | — | — | — |
| NLHL | — | — | — | — | — |

Table 4 shows the results on appearance of dipeptides, tripeptides and tetrapeptides in each of glycinin, β-conglycinin, gliadin, glutenin and lipovitellin.

TABLE 4

| | Soybean | | | | Wheat | |
| --- | --- | --- | --- | --- | --- | --- |
| | | β-Conglycinin | | | Gliadin | |
| | | SOYBN | SOYBN | | | |
| Oligopeptide | Glycinin SOYBN Glycinin 563 aa protein | Beta-conglycinin, alpha' chain 639 aa protein | Beta-conglycinin alpha-subunit 623 aa protein | Beta-conglycinin, beta chain 439 aa protein | WHEAT Alpha-glindin (Fragment) 288 aa protein | WHEAT Gamma-glindin 302 aa protein |
| LH | ○ | — | — | ○ | ○ | — |
| DV | ○ | ○ | — | ○ | ○ | — |
| MH | — | — | — | — | — | — |
| LHL | ○ | — | — | — | — | — |
| NLH | — | — | — | ○ | — | — |
| TDVE | — | — | — | — | — | — |
| NLHL | — | — | — | — | — | — |

| | Wheat | | | | Egg yolk | |
| --- | --- | --- | --- | --- | --- | --- |
| | Gliadin | | Glutenin | | Lipovitellin | |
| | | | WHEAT High-molecular weight | WHEAT Low molecular weight | (Vitellogenin-1 (Minor vitellogenin) | |
| Oligopeptide | WHEAT Alpha/beta-glindin 331 aa protein | WHEAT Omega-5 glindin 439 aa protein | glutonin subunit 2.6 OS 1025 aa protein | glutonin subunit OS 392 aa protein | (Vitellogenin I) 1,912 aa protein | (Vitellogenin-2 (Major vitellogenin) 1850 aa protein |
| LH | — | ○ | — | — | ○ | ○ |
| DV | ○ | ○ | — | — | ○ | ○ |
| MH | — | — | — | — | ○ | ○ |
| LHL | — | — | — | — | — | ○ |
| NLH | — | — | — | — | — | — |
| TDVE | — | — | — | — | — | — |
| NLHL | — | — | — | — | — | — |

Table 5 shows the results on appearance of dipeptides, tripeptides and tetrapeptides in each of ovalbumin, ovotransferrin, ovomucoid, ovomucin (mucin 5B), ovomucin (mucin 6), lysozyme and collagen.

TABLE 5

| | Egg white | | | | | | | Chicken Collagen | |
|---|---|---|---|---|---|---|---|---|---|
| | Ovalbumin | Ovotransferrin | Ovomucoid Ovomucoid | Ovomucin | Ovomucin Mucin-6 (Ovomucin, | Lysozyme | | Collagen alpha-1(I) | CHICK | CHICK |
| Oligo-peptide | Ovalbumin (Allergen Gal d II) (Egg albumin) 386 aa protein | Ovotransferrin (*Gallus gallus*, Chicken) 738 aa protein | (Allergen Gal d I) (allergen Gal d 1) 210 aa protein | Mucin-5B (Ovomucin, alpha-subunit) 2108 aa protein | beta, subunit) *Gallus gallus* (Chicken) 1185 aa protein | Lysozyme g *Gallus gallus* (Chicken) 211 aa protein | Lysozyme C 147 aa protein | chain (Alpha-1 type I collagen) chicken 1453 aa protein | Collagen alpha-1(II) chain (Fragment) 369 aa protein | Collagen alpha-2(I) chain (Fragment) 1362 aa protein |
| LH | — | ○ | — | ○ | ○ | ○ | — | — | — | ○ |
| DV | ○ | ○ | ○ | ○ | ○ | ○ | ○ | ○ | ○ | ○ |
| MH | — | — | — | ○ | ○ | ○ | — | — | — | — |
| LHL | — | — | — | — | ○ | — | — | — | — | — |
| NLH | — | — | — | — | — | — | — | — | — | — |
| TDVE | — | — | — | — | — | — | — | — | — | — |
| NLHL | — | — | — | — | — | — | — | — | — | — |

As a result, the sequences of dipeptides found effective in having anti-inflammatory activities against microglia in Test Example 1 and the tripeptides and the tetrapeptides confirmed to have anti-inflammatory activities in Test Example 3 are revealed to have been included in any of the above 34 proteins and confirmed to be preparable from raw materials containing these proteins by acid hydrolysis or enzyme treatment.

The above oligopeptides were further analyzed to see how much is contained in proteins derived from foods. The results are shown in Tables 6 and 7.

TABLE 6

| Source food | Source protein | LH (Number of sequence) | DV (Number of sequence) | MH (Number of sequence) |
|---|---|---|---|---|
| Milk | αS1 Casein | 1 | 1 | 0 |
| Milk | β Casein | 1 | 1 | 1 |

TABLE 6-continued

| Source food | Source protein | LH (Number of sequence) | DV (Number of sequence) | MH (Number of sequence) |
|---|---|---|---|---|
| Milk | Lactoperoxidase | 2 | 0 | 0 |
| Milk | β-Lactoglobulin | 0 | 0 | 1 |
| Milk | Lactoferrin | 1 | 3 | 0 |
| Milk | BSA | 2 | 1 | 0 |
| Soybean | Glycinin | 2 | 2 | 0 |
| Soybean | Conglycinin | 1 | 3 | 0 |
| Wheat | Gliadin | 2 | 3 | 0 |
| Egg yolk | Lipovitellin | 5 | 15 | 3 |
| Egg white | ovalbumin | 0 | 3 | 0 |
| Egg white | Ovotransferrin | 1 | 4 | 0 |
| Egg white | Ovomucoid | 0 | 1 | 0 |
| Egg white | Mucin | 1 | 4 | 3 |
| Egg white | Lysozyme | 1 | 2 | 0 |
| Chicken | Collagen | 2 | 8 | 0 |

TABLE 7

| Source food | Source protein | LHL (Number of sequence) | NLH (Number of sequence) | TDVE (Number of sequence) | NLHL (Number of sequence) |
|---|---|---|---|---|---|
| Milk | αS1 Casein | 0 | 0 | 0 | 0 |
| Milk | β Casein | 1 | 1 | 1 | 1 |
| Milk | Lactoperoxidase | 0 | 0 | 0 | 0 |
| Milk | β-Lactoglobulin | 0 | 0 | 0 | 0 |
| Milk | Lactoferrin | 0 | 0 | 0 | 0 |
| Milk | BSA | 0 | 0 | 0 | 0 |
| Soybean | Glycinin | 1 | 0 | 0 | 0 |
| Soybean | Conglycinin | 0 | 1 | 0 | 0 |
| Wheat | Gliadin | 0 | 0 | 0 | 0 |
| Egg yolk | Lipovitellin | 1 | 0 | 0 | 0 |
| Egg white | ovalbumin | 0 | 0 | 0 | 0 |
| Egg white | Ovotransferrin | 0 | 0 | 0 | 0 |
| Egg white | Ovomucoid | 0 | 0 | 0 | 0 |
| Egg white | Mucin | 1 | 0 | 0 | 0 |
| Egg white | Lysozyme | 0 | 0 | 0 | 0 |
| Chicken | Collagen | 0 | 0 | 0 | 0 |

It was confirmed that at least any of the dipeptides to be the core is included in the proteins derived from foods shown in the above. The tripeptides and the tetrapeptides confirmed to have the inflammation suppression activity in Test Example 3 are contained in 3 casein. The peptide composition having a high microglia inflammation suppression effect can be produced by using the oligopeptide contained in proteins contained in these food products.

Test Example 7

(1) Microglia Inflammation Suppression Effect by Water Extract of Shochu Kasu

In accordance with a conventional method, koji (rice malt) was produced by simmering and cooling a koji raw material (white rice (non-glutinous rice) to which a seed koji (white koji or black koji) was added. Yeast was added thereto and fermented. The main raw material simmered and then cooled (white rice (non-glutinous rice), barley or sweet potato) was further added and fermented. The moromi (unrefined mash) obtained by the fermentation was distilled to produce unprocessed shochu.

The present test was carried out intending on the distillation residue of moromi at the time of shochu production. More specifically, 5-fold weight (W/W) of water to the moromi distillation residue (hereinafter also referred to as "moromi residue" "shouchukasu") was added and sonicated for 15 minutes (water extraction). The water extraction was carried out at 25° C. The supernatant of centrifuged (using Himac CR20GII, manufactured by HITACHI, 5,000 rpm× 10 min.) extract was collected and lyophilized to use as the lyophilized sample.

The sample is shown in Table 8.

TABLE 8

| Sample No. | Main raw material | Koji raw material/Koji mold |
|---|---|---|
| #1 | White rice (non-glutinous rice) | White rice (non-glutinous rice)/white koji |
| #2 | Barley | Barley/Black koji |
| #3 | Sweet potato | Sweet potato/White koji |
| #4 | Sweet potato | Sweet potato/Black koji |
| #5 | Barley | Barley/White koji |

The primary cultured microglia collected and purified from the mouse brain by the method described in Test Example 1 were evaluated for the inflammation suppression action when the lyophilized sample was added. Specifically, the lyophilized sample was added to make the final concentrations of 0.1, 0.3, 1, 3 mg/mL, respectively to culture plates in which the purified primary cultured microglia were inoculated and the culture was carried out for 24 hours, and LPS and IFN-γ were added to make the final concentrations of 5 ng/mL, 0.5 ng/mL, respectively to carry out the culture (0.1 mg group, 0.3 mg group, 1 mg group, 3 mg group). The amount of TNF-α in the culture supernatant after 12 hours of culture was quantitatively determined by ELISA. Note that the system to which the lyophilized sample was not added but LPS and INF-γ were added is called a control (+) and the system to which neither LPS nor IFN-γ was added is called a control (−).

Figure 7A:
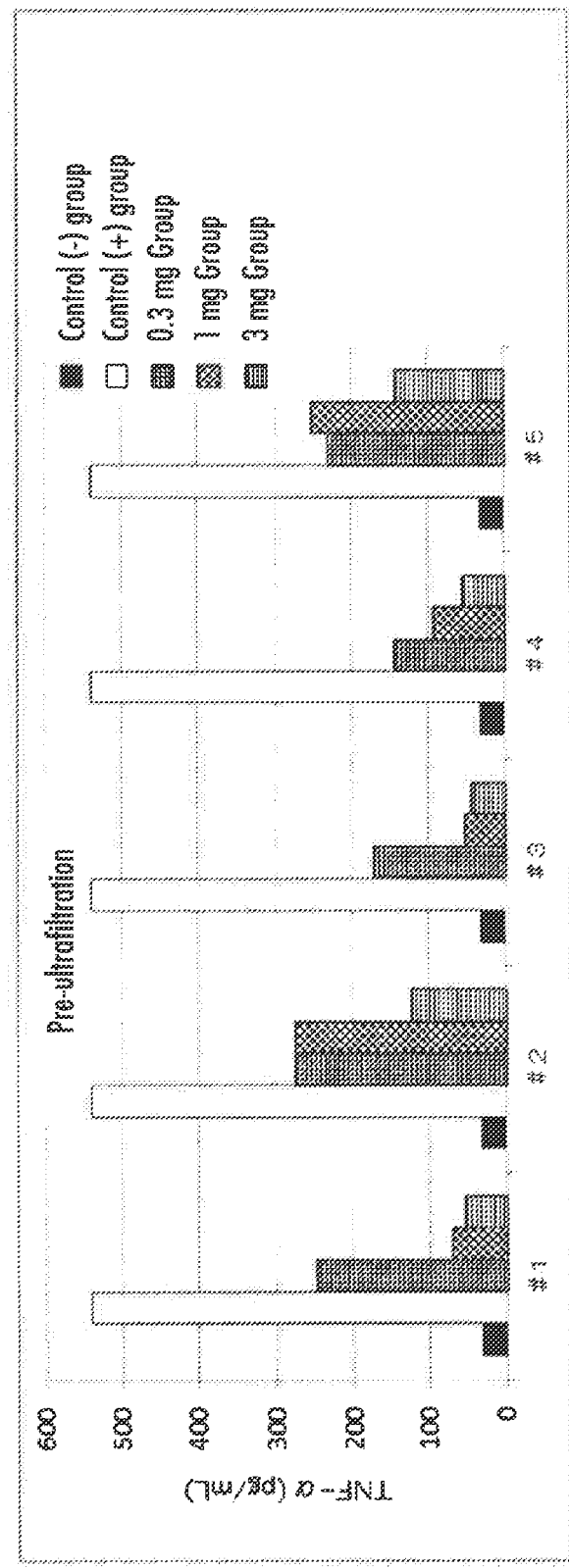
FIG. 7A is a graph showing the investigation results on the inflammation suppression effect of a water extract (pre-ultrafiltration) of shochu kasu (distilled spirit lees) against microglia in Test Example 7 (1).

The results are shown in FIG. 7A. Note that the results are represented in the average values of two consecutive data.

As a result, it was found that the amounts of TNF-α produced tended to be smaller in all the systems to which the lyophilized sample was added than the system to which the lyophilized sample was not added, and the higher the final concentration of the lyophilized sample was, the amount of TNF-α produced tended to be smaller. From these findings, it was revealed that components suppressing the microglia inflammatory condition are contained in the lyophilized samples.

(2) Membrane Process Impact on Microglia Inflammation Suppression Effect by Shochu Kasu Water Extract The culture broth prepared by adding the lyophilized sample obtained in (1) to make the final concentrations of 0.3, 1, 3 mg/mL was filtered using a 2 kDa ultrafiltration membrane to evaluate the microglia inflammation suppression effect by the same method as in (1).

The results are shown in FIG. 7B. It was found that the filtered lyophilized sample tended to have a smaller TNF-α amount than before filtration (FIG. 7A), revealing the inflammation suppression effect equivalent to or more than before filtration. This finding revealed that the component involved is contained in the fraction of 2 kDa or less.

(3) LH Concentration in Lyophilized Sample

The LH concentration was quantitatively determined by the LC/MSMS method. More specifically, an analysis sample obtained by ultrafiltering (10 kDa) the supernatant of the product obtained by dissolving the above lyophilized sample in water and centrifuging was suitably diluted and measured by LC/MSMS under the following analysis conditions. Concentration conversion was carried out by the calibration curve method.

(Analysis Conditions)

Mass spectrometer: 4000Q TRAP (manufactured by AB Sciex)
Pump: Agilent 1200 Binary Pump (manufactured by Agilent Technologies)
Autosampler: Agilent 1200 High Performance Autosampler (manufactured by Agilent Technologies)
Software version: Analyst 1.6.2
Column: TSK gel ODS-100V 3 μm 2.0 mm I.D.×150 mm (manufactured by TOSOH CORP)
Column temperature: 70° C.
Mobile phase A: 0.1 vol % formic acid
Mobile phase B: 0.1 vol % formic acid/acetonitrile

TABLE 9

| [Step Table] | | | |
|---|---|---|---|
| Total time (min.) | Flow rate (μL) | A (%) | B (%) |
| 0 | 200 | 95 | 5 |
| 30 | 200 | 20 | 80 |
| 30.01 | 200 | 95 | 5 |
| 40 | 200 | 95 | 5 |

Injection volume: 2 μL
Scan type: MRM (MRM)
Polarity: Positive
Scan mode: N/A
Ion source: Turbo spray
Resolution Q1: Unit
Resolution Q3: Unit
Intensity threshold: 0.00 cps
Settling time: 0.0000 msec
MR pose: 5.0000 msec
MCA: None
Step size: 0.00 Da

TABLE 10

[Parameter Table]

| | |
|---|---|
| CUR: | 40 |
| IS: | 5000 |
| TEM: | 600 |
| GS1: | 50 |
| GS2: | 80 |
| ihe: | ON |
| CAD: | 4 |
| EP | 10 |
| Monitor ion | LH |
| Q1 Mass: | 269.226 Da |
| Q3 Mass: | 156.1 Da |
| Time | 150 msec |
| DB | 58 V |
| EP | 25 V |
| CE | 25 V |
| CXP | 8 V |

The results are shown in Table 11. The concentration of LH is calculated as per dry mass of the shochu kasu water extract. In all the cases where non-glutinous rice, barley and sweet potato were used as the main raw materials, the production of LH by the fermentation was confirmed, suggesting that LH is involved with the microglia inflammation suppression action. Additionally, in all the cases where non-glutinous rice, barley and sweet potato were used as the koji raw materials and in the cases where white koji or black koji was used as the koji mold, the production of LH by the fermentation was confirmed, suggesting that LH is involved with the action of microglia.

TABLE 11

| Sample No. | LH Concentration (μg/g shochu kasu water extract) |
|---|---|
| #1 | 29.39 |
| #2 | 84.83 |
| #3 | 23.58 |
| #4 | 29.39 |
| #5 | 102.60 |

(4) Literature Searching

The inclusion of the amino acid sequence LH in the above main raw materials and in the protein of potato commonly used as a shochu raw material was predicted from the website information. The results are as shown in Table 12. The presence of the protein including the LH sequence was confirmed in all of barley, rice, sweet potato and potato used as the main raw materials, literally suggesting the possibility of LH production by the fermentation of these materials.

TABLE 12

| Grain name | Source | Protein name, Number of amino acids | Sequence | Number of LHs |
|---|---|---|---|---|
| Barley | http://www.ncbi.nlm.nih.gov/protein/AEW46726.1 | alpha prolamin (216 aa protein) | SEQ ID NO: 33 | 0 |
| Barley | http://www.ncbi.nlm.nih.gov/protein/CAA51204.1 | gamma 3 hordein, partial (286 aa protein) | SEQ ID NO: 34 | 0 |
| Barley | http://www.ncbi.nlm.nih.gov/protein/326521848 | predicted protein (571 aa protein) | SEQ ID NO: 35 | 2 |
| Barley | http://www.ncbi.nlm.nih.gov/protein/AAP31050.1 | globulin (224 aa protein) | SEQ ID NO: 36 | 0 |
| Barley | http://www.ncbi.nlm.nih.gov/protein/AAA32936.1 | embryo globulin (637 aa protein) | SEQ ID NO: 37 | 1 |
| Rice | http://www.ncbi.nlm.nih.gov/protein/BAC77348.1 | glutelin (500 aa protein) | SEQ ID NO: 38 | 0 |
| Rice | http://www.ncbi.nlm.nih.gov/protein/AGT59179.1 | glutelin, partial (468 aa protein) | SEQ ID NO: 39 | 1 |
| Sweet potato | http://www.ncbi.nlm.nih.gov/protein/AAB52548.1 | sporamin precursor (219 aa protein) | SEQ ID NO: 40 | 0 |
| Sweet potato | http://www.ncbi.nlm.nih.gov/protein/AAB52550.1 | sporamin, partial (171 aa protein) | SEQ ID NO: 41 | 1 |
| Sweet potato | http://www.ncbi.nlm.nih.gov/protein/BAA14024.1 | ipomoelin (154 aa protein) | SEQ ID NO: 42 | 0 |
| Potato | http://www.ncbi.nlm.nih.gov/protein/1YP4_D | Chain D, Crystal Structure Of Potato Tuber Adp-glucose Pyrophosphorylase In Complex With Adp-glucose (451 aa protein) | SEQ ID NO: 43 | 0 |
| Potato | http://www.ncbi.nlm.nih.gov/protein/ACN65408.1 | cytokinin oxidase/dehydrogenese 1 (543 aa protein) | SEQ ID NO: 44 | 2 |

(5) Conclusion

It was revealed that shochu kasu (preferably shochu kasu water extract) has the effect of suppressing microglial-mediated inflammation. Considering the results of Test Examples 4 and 5 all together, it is supposed that shochu kasu contains the component which has the effects of relieving stress, suppressing a vitality decrease and maintaining willingness and motivation. Shochu kasu is known to have been taken by human evidently and also by animals as feed. For this reason, it was learned that stress on human, livestock and pets is expected to be relieved by utilizing shochu kasu.

Preparation Example 1

A skim milk powder or a defatted soybean protein is dissolved in water and treated enzymatically to produce a peptide extract containing about 1% of LH, DV or MH. Using the peptide extract, a LH-, DV- or MH-containing lemon flavored carbonated drink having the composition shown in Table 13 was prepared. Note that LH, DV and MH in the peptide extract and the drink can each be quantitatively determined by the LC/MSMS method described in Test Example 7.

TABLE 13

| Lemon flavored carbonated drink | Per 100 g |
|---|---|
| Peptide extract (containing about 1% of LH, DV or MH) | 100 mg |
| High fructose corn syrup | 10.5 g |
| Sugar | 2 g |
| Citric acid | 0.12 g |
| Lemon flavor | 0.15 g |
| Carbon dioxide gas | Add to make a gas inner pressure after filling at 0.3 MPa |
| Ion exchange water | q.s. |

LH, DV or MH can be effectively taken by taking this lemon flavored carbonated drink.

Preparation Example 2

A peptide extract containing about 1% of LH, DV or MH was produced in the same manner as in Preparation Example 1. Using the peptide extract, a LH-, DV- or MH-containing coffee preparation liquid having the composition shown in Table 14 was prepared and sterilized at 121° C. for 10 minutes to obtain a canned coffee drink. Note that LH, DV and MH in the peptide extract and the drink can each be quantitatively determined by the LC/MSMS method described in Test Example 7.

TABLE 14

| Coffee drink | Per 100 g |
|---|---|
| Peptide extract (containing about 1% of LH, DV or MH) | 100 mg |
| Coffee liquid (obtained by extracting 100 g of medium ground coffee beans with 1 L of hot water at 95° C.) | 80 mL |
| Sugar | 10 g |
| Sodium hydrogen carbonate | 100 mg |
| Ion exchange water | q.s. |

LH, DV or MH can be effectively taken by taking this coffee drink.

Preparation Example 3

A peptide extract containing about 1% of LH, DV or MH was produced in the same manner as in Preparation Example 1. Using the peptide extract, a LH-, DV- or MH-containing milk tea preparation liquid having the composition shown in Table 15 was prepared and sterilized at 121° C. for 10 minutes to obtain a canned milk tea drink. Note that LH, DV and MH in the peptide extract and the drink can each be quantitatively determined by the LC/MSMS method described in Test Example 7.

TABLE 15

| Milk tea drink | Per 100 g |
|---|---|
| Peptide extract (containing about 1% of LH, DV or MH) | 400 mg |
| English tea liquid (obtained by extracting 100 g of English tea leaves in 3000 g of ion exchanged water at 98° C. for 14 minutes and adding ion exchange water to the supernatant obtained by filtering and centrifuging at room temperature to make 3000 g) | 80 mL |
| Sugar | 5 g |
| Cow's milk | 5 g |
| Stabilizer | 0.4 g |
| Ion exchange water | q.s. |

LH, DV or MH can be effectively taken by taking this milk tea drink.

Preparation Example 4

A peptide extract containing about 1% of LH, DV or MH was produced in the same manner as in Preparation Example 1. Using the peptide extract, a LH-, DV- or MH-containing fruit juice drink having the composition shown in Table 16 was prepared. Note that LH, DV and MH in the peptide extract and the drink can each be quantitatively determined by the LC/MSMS method described in Test Example 7.

TABLE 16

| Fruit juice drink | Per 100 g |
|---|---|
| Peptide extract (containing about 1% of LH, DV or MH) | 100 mg |
| 5-fold concentrated orange juice | 20 g |
| Ion exchange water | q.s. |

LH, DV or MH can be effectively taken by taking this fruit juice drink.

Preparation Example 5

A peptide extract containing about 1% of LH, DV or MH was produced in the same manner as in Preparation Example 1. Using the peptide extract, a LH-, DV- or MH-containing isotonic drink having the composition shown in Table 17 was prepared. Note that LH, DV and MH in the peptide extract and the drink can each be quantitatively determined by the LC/MSMS method described in Test Example 7.

TABLE 17

| Isotonic drink | Per 100 g |
|---|---|
| Peptide extract (containing about 1% of LH, DV or MH) | 300 mg |
| Sugar | 1 g |
| Fructose | 1 g |
| Glucose | 1 g |
| Citric acid | 0.5 g |
| Sodium chloride | 0.12 g |
| Potassium chloride | 0.15 g |
| Calcium Lactate | 0.03 g |
| Magnesium chloride | 0.03 g |
| Ion exchange water | q.s. |

LH, DV or MH can be effectively taken by taking this isotonic drink.

Preparation Example 6

A peptide extract containing about 1% of LH, DV or MH was produced in the same manner as in Preparation Example 1. Using the peptide extract, a LH-, DV- or MH-containing yogurt flavored drink having the composition shown in Table 18 was prepared. The preparation was carried out by homogenizing the raw materials other than the starter at about 70° C. (15 MPa), heat sterilizing (95° C. for 15 minutes), subsequently adding the starter to ferment at 30° C. for 10 hours. The preparation was stirred at the time pH reached 4.60 and cooled to about 25° C. and emulsified (15 MPa). Note that LH, DV and MH in the peptide extract and the drink can each be quantitatively determined by the LC/MSMS method described in Test Example 7.

TABLE 18

| Yogurt flavored drink | Per 100 g |
|---|---|
| Peptide extract (containing about 1% of LH, DV or MH) | 500 mg |
| Cow's milk | 7 g |

TABLE 18-continued

| Yogurt flavored drink | Per 100 g |
|---|---|
| Skim milk powder | 7 g |
| Sugar | 100 mg |
| Pectin | 30 mg |
| Starter (*L. Lactis* JCM5805) | 0.2 g |
| Ion exchange water | q.s. |

LH, DV or MH can be effectively taken by taking this yogurt flavored drink.

Preparation Example 7

A peptide extract containing LH, DV or MH or a synthetic dipeptide of LH, DV or MH was produced. Using the peptide extract or the synthetic dipeptide, a LH-, DV- or MH-containing tablet was prepared. Cellulose, cyclic oligosaccharide, sucrose ester, a paste (pullulan) or calcium phosphate may be added to the raw material. LH, DV or MH can be effectively taken by taking this tablet.

The invention claimed is:

1. A method of suppressing microglial-mediated inflammation, comprising administering, to a subject in need of such suppression, a peptide, or a pharmaceutically acceptable salt or a solvate thereof, wherein the amino acid sequence of said peptide consists of the amino acid sequence Leu-His.

2. A method of relieving or treating a symptom of chronic fatigue syndrome, cognitive impairment, or mood disorder, comprising administering, to a subject in need of such relief or treatment, a peptide, or a pharmaceutically acceptable salt or a solvate thereof, wherein the amino acid sequence of said peptide consists of the amino acid sequence Leu-His.

3. A method of relieving a condition caused by stress, comprising administering, to a subject in need of such relief, a peptide, or a pharmaceutically acceptable salt or a solvate thereof, wherein the amino acid sequence of said peptide consists of the amino acid sequence Leu-His.

4. The method according to claim 3, wherein the condition caused by stress is accompanied by a lack or decrease of willingness, motivation, or vitality to make a voluntary action.

5. The method according to claim 1, wherein the administration of said peptide, pharmaceutically acceptable salt, or solvate thereof, is performed orally.

6. The method according to claim 2, wherein the administration of said peptide, pharmaceutically acceptable salt, or solvate thereof, is performed orally.

7. The method according to claim 3, wherein the administration of said peptide, pharmaceutically acceptable salt, or solvate thereof, is performed orally.

8. The method according to claim 4, wherein the administration of said peptide, pharmaceutically acceptable salt, or solvate thereof, is performed orally.

9. The method according to claim 1, wherein said peptide, pharmaceutically acceptable salt, or solvate thereof, is administered in a form of a food or drink.

10. The method according to claim 2, wherein said peptide, pharmaceutically acceptable salt, or solvate thereof, is administered in a form of a food or drink.

11. The method according to claim 3, wherein said peptide, pharmaceutically acceptable salt, or solvate thereof, is administered in a form of a food or drink.

12. The method according to claim 4, wherein said peptide, pharmaceutically acceptable salt, or solvate thereof, is administered in a form of a food or drink.

13. The method according to claim 1, wherein said peptide, pharmaceutically acceptable salt, or solvate thereof, is administered in a form of a pharmaceutical.

14. The method according to claim 2, wherein said peptide, pharmaceutically acceptable salt, or solvate thereof, is administered in a form of a pharmaceutical.

15. The method according to claim 3, wherein said peptide, pharmaceutically acceptable salt, or solvate thereof, is administered in a form of a pharmaceutical.

16. The method according to claim 4, wherein said peptide, pharmaceutically acceptable salt, or solvate thereof, is administered in a form of a pharmaceutical.

* * * * *